(12) United States Patent
Ryan et al.

(10) Patent No.: US 12,734,351 B2
(45) Date of Patent: Sep. 15, 2026

(54) CATHETER BLOOD PUMP DELIVERY, GUIDING SYSTEMS AND METHODS OF USE

(71) Applicant: Supira Medical, Inc., Los Gatos, CA (US)

(72) Inventors: Ari Ryan, Sunnyvale, CA (US); Michael Calomeni, San Jose, CA (US)

(73) Assignee: Supira Medical, Inc., Los Gatos, CA (US)

( * ) Notice: Subject to any disclaimer, the term of this patent is extended or adjusted under 35 U.S.C. 154(b) by 1111 days.

(21) Appl. No.: 17/632,554

(22) PCT Filed: Aug. 7, 2020

(86) PCT No.: PCT/US2020/045441
§ 371 (c)(1),
(2) Date: Feb. 3, 2022

(87) PCT Pub. No.: WO2021/026472
PCT Pub. Date: Feb. 11, 2021

(65) Prior Publication Data

US 2022/0273933 A1 Sep. 1, 2022

Related U.S. Application Data

(60) Provisional application No. 62/883,735, filed on Aug. 7, 2019.

(51) Int. Cl.
*A61M 60/13* (2021.01)
*A61M 60/174* (2021.01)
(Continued)

(52) U.S. Cl.
CPC .......... *A61M 60/13* (2021.01); *A61M 60/174* (2021.01); *A61M 60/237* (2021.01);
(Continued)

(58) Field of Classification Search
CPC .... A61M 60/13; A61M 60/237; A61M 60/81; A61M 60/827; A61M 60/867;
(Continued)

(56) References Cited

U.S. PATENT DOCUMENTS 1,061,107 A 5/1913 Nordmark
1,596,933 A 8/1926 Kister
(Continued)

FOREIGN PATENT DOCUMENTS

CA 2352234 A1 6/2000
CA 2739899 C 5/2017
(Continued)

OTHER PUBLICATIONS

Varghai et al.; U.S. Appl. No. 17/794,002 entitled "Intravascular blood pumps, motors, and fluid control," filed Jul. 20, 2022.
(Continued)

*Primary Examiner* — Courtney D Heinle
*Assistant Examiner* — Andrew Thanh Bui
(74) *Attorney, Agent, or Firm* — Shay Glenn LLP

(57) ABSTRACT

Catheter blood pumps that include a pump portion with an impeller. The blood pumps include an axially extendable member with a distal end that is disposed further distally than the distal end of the impeller, and a guide member extending through the pump portion and axially moveable relative to the pump portion, the guide member inoperable axial communication with the extendable member such that axial movement of the guide member causes axial movement of the extendable member relative to the pump portion.

9 Claims, 20 Drawing Sheets

(51) Int. Cl.
*A61M 60/237* (2021.01)
*A61M 60/414* (2021.01)
*A61M 60/808* (2021.01)
*A61M 60/81* (2021.01)
*A61M 60/825* (2021.01)
*A61M 60/827* (2021.01)
*A61M 60/867* (2021.01)

(52) U.S. Cl.
CPC ........ *A61M 60/414* (2021.01); *A61M 60/808* (2021.01); *A61M 60/81* (2021.01); *A61M 60/825* (2021.01); *A61M 60/827* (2021.01); *A61M 60/867* (2021.01)

(58) Field of Classification Search
CPC .............. A61M 60/414; A61M 60/825; A61M 60/808; A61M 60/174; A61M 60/148; A61M 60/205; A61M 60/216; A61M 60/422; F04D 3/00
See application file for complete search history.

(56) References Cited

U.S. PATENT DOCUMENTS 3,152,618 A 10/1964 Rothermel et al.
3,175,555 A 3/1965 Ling
3,178,833 A 4/1965 Gulbransen, Jr.
3,208,448 A 9/1965 Woodward
3,233,609 A 2/1966 Leucci
3,421,497 A 1/1969 Chesnut
3,502,412 A 3/1970 Burns
3,504,662 A 4/1970 Jones
3,505,987 A 4/1970 Heilman
3,568,659 A 3/1971 Karnegis
3,693,612 A 9/1972 Donahoe et al.
3,734,648 A 5/1973 Nielson
3,774,243 A 11/1973 Ng et al.
3,837,922 A 9/1974 Ng et al.
3,841,837 A 10/1974 Kitrilakis et al.
3,860,968 A 1/1975 Shapiro
3,919,722 A 11/1975 Harmison
4,015,590 A 4/1977 Normann
4,037,984 A 7/1977 Rafferty et al.
4,046,137 A 9/1977 Curless et al.
4,058,857 A 11/1977 Runge et al.
4,093,726 A 6/1978 Winn et al.
4,135,253 A 1/1979 Reich et al.
4,142,845 A 3/1979 Lepp et al.
4,173,796 A 11/1979 Jarvik
4,190,047 A 2/1980 Jacobsen et al.
4,255,821 A 3/1981 Carol et al.
4,289,141 A 9/1981 Cormier
4,310,930 A 1/1982 Goldowsky
4,311,133 A 1/1982 Robinson
4,328,806 A 5/1982 Cooper
4,370,983 A 2/1983 Lichtenstein
4,381,005 A 4/1983 Bujan
4,381,567 A 5/1983 Robinson et al.
4,382,199 A 5/1983 Isaacson
4,389,737 A 6/1983 Robinson et al.
4,397,049 A 8/1983 Robinson et al.
4,407,304 A 10/1983 Lieber et al.
4,506,658 A 3/1985 Casile
4,515,589 A 5/1985 Austin et al.
4,522,195 A 6/1985 Schiff
4,524,466 A 6/1985 Hall et al.
4,551,073 A 11/1985 Schwab
4,576,606 A 3/1986 Pol et al.
4,585,004 A 4/1986 Brownlee
4,585,007 A 4/1986 Uchigaki et al.
4,599,081 A 7/1986 Cohen
4,600,405 A 7/1986 Zibelin
4,623,350 A 11/1986 Lapeyre et al.
4,625,712 A 12/1986 Wampler
4,652,265 A 3/1987 McDougall
4,662,358 A 5/1987 Farrar et al.
4,666,598 A 5/1987 Heath et al.
4,675,361 A 6/1987 Ward
4,685,910 A 8/1987 Schweizer
4,726,379 A 2/1988 Altman et al.
4,753,221 A 6/1988 Kensey et al.
4,767,289 A 8/1988 Parrott et al.
4,771,777 A 9/1988 Horzewski et al.
4,779,614 A 10/1988 Moise
4,782,817 A 11/1988 Singh et al.
4,785,795 A 11/1988 Singh
4,802,650 A 2/1989 Stricker
4,818,186 A 4/1989 Pastrone et al.
4,826,481 A 5/1989 Sacks et al.
4,846,152 A 7/1989 Wampler et al.
4,846,831 A 7/1989 Skillin
4,850,957 A 7/1989 Summers
4,888,009 A 12/1989 Lederman et al.
4,888,011 A 12/1989 Kung et al.
4,902,272 A 2/1990 Milder et al.
4,907,592 A 3/1990 Harper
4,908,012 A 3/1990 Moise et al.
4,919,647 A 4/1990 Nash
4,936,759 A 6/1990 Clausen et al.
4,961,738 A 10/1990 Mackin
4,976,683 A 12/1990 Gauthier et al.
4,995,857 A 2/1991 Arnold
5,026,367 A 6/1991 Leckrone et al.
D318,113 S 7/1991 Moutafis et al.
5,045,051 A 9/1991 Milder et al.
5,046,503 A 9/1991 Schneiderman
5,047,147 A 9/1991 Chevallet et al.
5,049,134 A 9/1991 Golding et al.
5,061,256 A 10/1991 Wampler
5,084,064 A 1/1992 Barak et al.
5,089,016 A 2/1992 Millner et al.
5,090,957 A 2/1992 Moutafis et al.
5,092,844 A 3/1992 Schwartz et al.
5,092,879 A 3/1992 Jarvik
5,112,200 A 5/1992 Isaacson et al.
5,112,292 A 5/1992 Hwang et al.
5,114,399 A 5/1992 Kovalcheck
5,116,305 A 5/1992 Milder et al.
5,139,517 A 8/1992 Corral
5,145,333 A 9/1992 Smith
5,147,281 A 9/1992 Thornton et al.
5,171,264 A 12/1992 Merrill
5,180,378 A 1/1993 Kung et al.
5,192,314 A 3/1993 Daskalakis
5,200,050 A 4/1993 Ivory et al.
5,205,721 A 4/1993 Isaacson
5,211,546 A 5/1993 Isaacson et al.
5,261,411 A 11/1993 Hughes
5,270,005 A 12/1993 Raible
5,287,858 A 2/1994 Hammerslag et al.
5,300,111 A 4/1994 Panton et al.
5,300,112 A 4/1994 Barr
5,314,418 A 5/1994 Takano et al.
5,322,413 A 6/1994 Vescovini et al.
5,326,344 A 7/1994 Bramm et al.
5,363,856 A 11/1994 Hughes et al.
5,397,349 A 3/1995 Kolff et al.
5,399,074 A 3/1995 Nose et al.
5,405,251 A 4/1995 Sipin
5,441,636 A 8/1995 Chevallet et al.
5,443,504 A 8/1995 Hill
5,486,192 A 1/1996 Walinsky et al.
5,487,727 A 1/1996 Snider et al.
5,507,629 A 4/1996 Jarvik
5,507,795 A 4/1996 Chiang et al.
5,510,267 A 4/1996 Marshall
5,512,042 A 4/1996 Montoya et al.
5,531,789 A 7/1996 Yamazaki et al.
5,628,731 A 5/1997 Dodge et al.
5,630,835 A 5/1997 Brownlee
5,643,172 A 7/1997 Kung et al.
5,643,215 A 7/1997 Fuhrman et al.
5,653,696 A 8/1997 Shiber
5,662,643 A 9/1997 Kung et al.

(56) References Cited

U.S. PATENT DOCUMENTS 5,676,526 A 10/1997 Kuwana et al.
5,683,231 A 11/1997 Nakazawa et al.
5,702,365 A 12/1997 King
5,713,730 A 2/1998 Nose et al.
5,735,892 A 4/1998 Myers et al.
5,749,839 A 5/1998 Kovacs
5,749,855 A 5/1998 Reitan
5,751,125 A 5/1998 Weiss
5,759,148 A 6/1998 Sipin
5,766,207 A 6/1998 Potter et al.
5,776,096 A 7/1998 Fields
5,800,138 A 9/1998 Merce Vives
5,800,457 A 9/1998 Gelbfish
5,803,720 A 9/1998 Ohara et al.
5,814,076 A 9/1998 Brownlee
5,814,102 A 9/1998 Guldner et al.
5,851,174 A 12/1998 Jarvik et al.
5,888,241 A 3/1999 Jarvik
5,906,579 A 5/1999 Vander Salm et al.
5,910,124 A 6/1999 Rubin
5,919,369 A 7/1999 Ash
5,941,813 A 8/1999 Sievers et al.
5,957,672 A 9/1999 Aber
5,964,694 A 10/1999 Siess et al.
5,984,893 A 11/1999 Ward
6,007,478 A 12/1999 Siess et al.
6,013,058 A 1/2000 Prosl et al.
6,022,363 A 2/2000 Walker et al.
6,030,336 A 2/2000 Franchi
6,042,347 A 3/2000 Scholl et al.
6,053,943 A 4/2000 Edwin et al.
6,066,085 A 5/2000 Heilman et al.
6,066,152 A 5/2000 Strauss et al.
6,068,588 A 5/2000 Goldowsky
6,071,093 A 6/2000 Hart
6,071,258 A 6/2000 Dalke et al.
6,082,105 A 7/2000 Miyata
6,101,406 A 8/2000 Hacker et al.
6,106,509 A 8/2000 Loubser
6,113,536 A 9/2000 Hosn et al.
6,117,130 A 9/2000 Kung
6,117,390 A 9/2000 Corey
6,120,537 A 9/2000 Wampler
6,123,659 A 9/2000 Le Blanc et al.
6,123,726 A 9/2000 Mori et al.
6,129,660 A 10/2000 Nakazeki et al.
6,136,025 A 10/2000 Barbut et al.
6,139,487 A 10/2000 Siess
6,142,752 A 11/2000 Akamatsu et al.
6,146,771 A 11/2000 Wirt et al.
6,149,683 A 11/2000 Lancisi et al.
6,152,704 A 11/2000 Hosn et al.
6,155,969 A 12/2000 Schima et al.
6,176,848 B1 1/2001 Rau et al.
6,180,058 B1 1/2001 Lindsay
6,197,055 B1 3/2001 Matthews
6,197,289 B1 3/2001 Wirt et al.
6,210,133 B1 4/2001 Hosn et al.
6,210,318 B1 4/2001 Lederman
6,228,023 B1 5/2001 Zaslavsky et al.
6,236,883 B1 5/2001 Ciaccio et al.
6,254,359 B1 7/2001 Aber
6,270,831 B2 8/2001 Kumar et al.
6,273,861 B1 8/2001 Bates et al.
6,283,949 B1 9/2001 Roorda
6,287,319 B1 9/2001 Hosn et al.
6,290,685 B1 9/2001 Insley et al.
6,312,462 B1 11/2001 McDermott et al.
6,314,322 B1 11/2001 Rosenberg
6,319,231 B1 11/2001 Andrulitis
6,361,292 B1 3/2002 Chang et al.
6,361,501 B1 3/2002 Amano et al.
6,364,833 B1 4/2002 Valerio et al.
6,398,715 B1 6/2002 Magovern et al.
6,400,991 B1 6/2002 Kung
6,406,267 B1 6/2002 Mondiere
6,406,422 B1 6/2002 Landesberg
6,419,657 B1 7/2002 Pacetti
6,422,990 B1 7/2002 Prem
6,432,136 B1 8/2002 Weiss et al.
6,443,944 B1 9/2002 Doshi et al.
6,443,983 B1 9/2002 Nagyszalanczy et al.
6,445,956 B1 9/2002 Laird et al.
6,447,265 B1 9/2002 Antaki et al.
6,447,266 B2 9/2002 Antaki et al.
6,447,441 B1 9/2002 Yu et al.
6,497,680 B1 12/2002 Holst et al.
6,503,224 B1 1/2003 Forman et al.
6,503,450 B1 1/2003 Afzal et al.
6,508,787 B2 1/2003 Erbel et al.
6,508,806 B1 1/2003 Hoste
6,527,699 B1 3/2003 Goldowsky
6,533,716 B1 3/2003 Schmitz-Rode et al.
6,533,724 B2 3/2003 McNair
6,537,315 B2 3/2003 Yamazaki et al.
6,540,658 B1 4/2003 Fasciano et al.
6,540,659 B1 4/2003 Milbocker
6,544,543 B1 4/2003 Mandrusov et al.
6,547,716 B1 4/2003 Milbocker
6,562,022 B2 5/2003 Hoste et al.
6,572,529 B2 6/2003 Wilk
6,572,534 B1 6/2003 Milbocker et al.
6,595,943 B1 7/2003 Burbank
6,602,182 B1 8/2003 Milbocker
6,616,596 B1 9/2003 Milbocker
6,620,120 B2 9/2003 Landry et al.
6,623,420 B2 9/2003 Reich et al.
6,626,821 B1 9/2003 Kung et al.
6,626,889 B1 9/2003 Simpson et al.
6,626,935 B1 9/2003 Ainsworth et al.
6,632,215 B1 10/2003 Lemelson
6,635,083 B1 10/2003 Cheng et al.
6,656,220 B1 12/2003 Gomez et al.
6,669,624 B2 12/2003 Frazier
6,669,662 B1 12/2003 Webler
6,676,679 B1 1/2004 Mueller et al.
6,685,696 B2 2/2004 Fleischhacker et al.
6,688,869 B1 2/2004 Simonds
6,699,231 B1 3/2004 Sterman et al.
6,709,382 B1 3/2004 Horner
6,712,844 B2 3/2004 Pacetti
6,730,102 B1 5/2004 Burdulis et al.
6,746,416 B2 6/2004 Hubbard et al.
6,749,615 B2 6/2004 Burdulis et al.
6,769,871 B2 8/2004 Yamazaki
6,790,171 B1 9/2004 Gründeman et al.
6,811,749 B2 11/2004 Lindsay
6,821,295 B1 11/2004 Farrar
6,837,890 B1 1/2005 Chludzinski et al.
6,846,296 B1 1/2005 Milbocker et al.
6,866,650 B2 3/2005 Stevens et al.
6,879,126 B2 4/2005 Paden et al.
6,884,210 B2 4/2005 Nose et al.
6,908,280 B2 6/2005 Yamazaki
6,908,435 B1 6/2005 Mueller et al.
6,929,632 B2 8/2005 Nita et al.
6,929,660 B1 8/2005 Ainsworth et al.
6,942,672 B2 9/2005 Heilman et al.
6,945,978 B1 9/2005 Hyde
6,949,066 B2 9/2005 Bearson et al.
6,969,345 B2 11/2005 Jassawalla et al.
6,981,942 B2 1/2006 Khaw et al.
7,022,100 B1 4/2006 Hosn et al.
7,025,742 B2 4/2006 Rubenstein et al.
7,027,875 B2 4/2006 Siess et al.
7,029,483 B2 4/2006 Schwartz
7,037,253 B2 5/2006 French et al.
7,048,747 B2 5/2006 Arcia et al.
7,074,018 B2 7/2006 Chang
7,108,652 B2 9/2006 Stenberg et al.
7,118,525 B2 10/2006 Coleman et al.
7,122,151 B2 10/2006 Reeder et al.
7,125,376 B2 10/2006 Viole et al.
7,126,310 B1 10/2006 Barron

(56) References Cited

U.S. PATENT DOCUMENTS 7,150,711 B2 12/2006 Nüsser et al.
7,155,291 B2 12/2006 Zarinetchi et al.
7,172,551 B2 2/2007 Leasure
7,189,260 B2 3/2007 Horvath et al.
7,220,275 B2 5/2007 Davidson et al.
7,229,258 B2 6/2007 Wood et al.
7,229,402 B2 6/2007 Diaz et al.
7,238,151 B2 7/2007 Frazier
7,244,224 B2 7/2007 Tsukahara et al.
7,247,166 B2 7/2007 Pienknagura
7,303,581 B2 12/2007 Peralta
7,331,972 B1 2/2008 Cox
7,331,987 B1 2/2008 Cox
7,361,726 B2 4/2008 Pacetti et al.
7,377,927 B2 5/2008 Burdulis et al.
7,392,077 B2 6/2008 Mueller et al.
7,393,181 B2 7/2008 McBride et al.
7,396,327 B2 7/2008 Morello
7,479,102 B2 1/2009 Jarvik
7,520,850 B2 4/2009 Brockway
7,524,277 B1 4/2009 Wang et al.
7,541,000 B2 6/2009 Stringer et al.
7,544,160 B2 6/2009 Gross
7,547,391 B2 6/2009 Petrie
7,585,322 B2 9/2009 Azzolina
7,588,530 B2 9/2009 Heilman et al.
7,588,549 B2 9/2009 Eccleston
7,591,199 B2 9/2009 Weldon et al.
7,611,478 B2 11/2009 Lucke et al.
7,628,756 B2 12/2009 Hacker et al.
7,713,259 B2 5/2010 Gosiengfiao et al.
RE41,394 E 6/2010 Bugge et al.
7,731,664 B1 6/2010 Millar
7,736,296 B2 6/2010 Siess et al.
7,736,375 B2 6/2010 Crow
7,758,492 B2 7/2010 Weatherbee
7,776,991 B2 8/2010 Pacetti et al.
7,780,628 B1 8/2010 Keren et al.
7,794,419 B2 9/2010 Paolini et al.
7,794,743 B2 9/2010 Simhambhatla et al.
7,819,834 B2 10/2010 Paul
7,828,710 B2 11/2010 Shifflette
7,833,239 B2 11/2010 Nash
7,841,976 B2 11/2010 McBride et al.
7,850,594 B2 12/2010 Sutton et al.
7,862,501 B2 1/2011 Woodard
7,878,967 B1 2/2011 Khanal
7,914,436 B1 3/2011 Kung
7,922,657 B2 4/2011 Gillinov et al.
7,942,804 B2 5/2011 Khaw
7,963,905 B2 6/2011 Salmonsen et al.
7,972,122 B2 7/2011 LaRose et al.
7,972,291 B2 7/2011 Ibragimov
7,985,442 B2 7/2011 Gong
7,988,728 B2 8/2011 Ayre
7,993,259 B2 8/2011 Kang et al.
7,993,260 B2 8/2011 Bolling
7,993,358 B2 8/2011 O'Brien
7,998,054 B2 8/2011 Bolling
7,998,190 B2 8/2011 Gharib et al.
8,012,079 B2 9/2011 Delgado
8,012,194 B2 9/2011 Edwin et al.
8,012,508 B2 9/2011 Ludwig
8,029,728 B2 10/2011 Lindsay
8,034,098 B1 10/2011 Callas et al.
8,048,442 B1 11/2011 Hossainy et al.
8,052,749 B2 11/2011 Salahieh et al.
8,070,742 B2 12/2011 Woo
8,070,804 B2 12/2011 Hyde et al.
8,075,472 B2 12/2011 Zilbershlag et al.
8,079,948 B2 12/2011 Shifflette
8,083,726 B1 12/2011 Wang
8,123,669 B2 2/2012 Siess et al.
8,123,674 B2 2/2012 Kuyava
8,133,272 B2 3/2012 Hyde
RE43,299 E 4/2012 Siess
8,152,035 B2 4/2012 Earl
8,152,845 B2 4/2012 Bourque
8,153,083 B2 4/2012 Briggs
8,157,719 B1 4/2012 Ainsworth et al.
8,157,721 B2 4/2012 Sugiura
8,157,758 B2 4/2012 Pecor et al.
8,158,062 B2 4/2012 Dykes et al.
8,162,021 B2 4/2012 Tomasetti et al.
8,167,589 B2 5/2012 Hidaka et al.
8,172,783 B1 5/2012 Ray
8,177,750 B2 5/2012 Steinbach et al.
8,187,324 B2 5/2012 Webler et al.
8,197,463 B2 6/2012 Intoccia
8,210,829 B2 7/2012 Horvath et al.
8,241,199 B2 8/2012 Maschke
8,257,258 B2 9/2012 Zocchi
8,257,375 B2 9/2012 Maschke
8,266,943 B2 9/2012 Miyakoshi et al.
D669,585 S 10/2012 Bourque
8,277,476 B2 10/2012 Taylor et al.
8,282,359 B2 10/2012 Ayre et al.
8,292,908 B2 10/2012 Nieman et al.
D671,646 S 11/2012 Bourque et al.
8,303,482 B2 11/2012 Schima et al.
8,323,173 B2 12/2012 Benkowski et al.
8,323,203 B2 12/2012 Thornton
8,328,750 B2 12/2012 Peters et al.
8,329,114 B2 12/2012 Temple
8,329,158 B2 12/2012 Hossainy et al.
8,366,599 B2 2/2013 Tansley et al.
8,372,137 B2 2/2013 Pienknagura
8,377,033 B2 2/2013 Basu et al.
8,377,083 B2 2/2013 Mauch et al.
8,382,695 B1 2/2013 Patel
8,388,565 B2 3/2013 Shifflette
8,388,649 B2 3/2013 Woodard et al.
8,419,609 B2 4/2013 Shambaugh et al.
8,419,944 B2 4/2013 Alkanhal
8,439,909 B2 5/2013 Wang et al.
8,449,444 B2 5/2013 Poirier
8,454,683 B2 6/2013 Rafiee et al.
8,485,961 B2 7/2013 Campbell et al.
8,496,874 B2 7/2013 Gellman et al.
8,500,620 B2 8/2013 Lu et al.
8,506,471 B2 8/2013 Bourque
8,535,211 B2 9/2013 Campbell et al.
8,535,212 B2 9/2013 Robert
8,538,515 B2 9/2013 Atanasoska et al.
8,545,382 B2 10/2013 Suzuki et al.
8,545,447 B2 10/2013 Demarais et al.
8,562,509 B2 10/2013 Bates
8,568,289 B2 10/2013 Mazur
8,579,858 B2 11/2013 Reitan et al.
8,579,967 B2 11/2013 Webler et al.
8,585,572 B2 11/2013 Mehmanesh
8,586,527 B2 11/2013 Singh
8,591,393 B2 11/2013 Walters et al.
8,591,394 B2 11/2013 Peters et al.
8,591,449 B2 11/2013 Hudson
8,591,538 B2 11/2013 Gellman
8,591,539 B2 11/2013 Gellman
D696,769 S 12/2013 Schenck et al.
8,597,170 B2 12/2013 Walters et al.
8,608,661 B1 12/2013 Mandrusov et al.
8,613,777 B2 12/2013 Siess et al.
8,613,892 B2 12/2013 Stafford
8,617,239 B2 12/2013 Reitan
8,631,680 B2 1/2014 Fleischli et al.
8,632,449 B2 1/2014 Masuzawa et al.
8,641,594 B2 2/2014 LaRose et al.
8,657,871 B2 2/2014 Limon
8,657,875 B2 2/2014 Kung et al.
8,668,473 B2 3/2014 LaRose et al.
8,684,903 B2 4/2014 Nour
8,690,749 B1 4/2014 Nunez
8,690,823 B2 4/2014 Yribarren et al.
8,697,058 B2 4/2014 Basu et al.
8,708,948 B2 4/2014 Consigny et al.

(56) References Cited

U.S. PATENT DOCUMENTS 8,715,151 B2 5/2014 Poirier
8,715,156 B2 5/2014 Jayaraman
8,715,707 B2 5/2014 Hossainy et al.
8,721,516 B2 5/2014 Scheckel
8,721,517 B2 5/2014 Zeng et al.
8,734,331 B2 5/2014 Evans et al.
8,734,508 B2 5/2014 Hastings et al.
8,739,727 B2 6/2014 Austin et al.
8,740,920 B2 6/2014 Goldfarb et al.
8,741,287 B2 6/2014 Brophy et al.
8,758,388 B2 6/2014 Pah
8,766,788 B2 7/2014 D'Ambrosio
8,777,832 B1 7/2014 Wang et al.
8,790,399 B2 7/2014 Frazier et al.
8,795,576 B2 8/2014 Tao et al.
8,814,543 B2 8/2014 Liebing
8,814,776 B2 8/2014 Hastie et al.
8,814,933 B2 8/2014 Siess
8,815,274 B2 8/2014 DesNoyer et al.
8,821,366 B2 9/2014 Faman et al.
8,837,096 B2 9/2014 Seebruch
8,840,539 B2 9/2014 Zilbershlag
8,840,566 B2 9/2014 Seibel et al.
8,849,398 B2 9/2014 Evans
8,862,232 B2 10/2014 Zarinetchi et al.
8,864,642 B2 10/2014 Scheckel
8,876,685 B2 11/2014 Crosby et al.
8,882,744 B2 11/2014 Dormanen et al.
8,888,675 B2 11/2014 Stankus et al.
8,894,387 B2 11/2014 White
8,894,561 B2 11/2014 Callaway et al.
8,897,873 B2 11/2014 Schima et al.
8,900,060 B2 12/2014 Liebing
8,905,910 B2 12/2014 Reichenbach et al.
8,927,700 B2 1/2015 McCauley et al.
8,932,141 B2 1/2015 Liebing
8,932,197 B2 1/2015 Gregoric et al.
8,934,956 B2 1/2015 Glenn et al.
8,942,828 B1 1/2015 Schecter
8,944,748 B2 2/2015 Liebing
8,945,159 B2 2/2015 Nussbaum
8,956,402 B2 2/2015 Cohn
8,961,387 B2 2/2015 Duncan
8,961,466 B2 2/2015 Steinbach
8,971,980 B2 3/2015 Mace et al.
8,974,519 B2 3/2015 Gennrich et al.
8,992,406 B2 3/2015 Corbett
8,997,349 B2 4/2015 Mori et al.
9,002,468 B2 4/2015 Shea et al.
9,023,010 B2 5/2015 Chiu et al.
9,028,216 B2 5/2015 Schumacher et al.
9,028,392 B2 5/2015 Shifflette
9,028,859 B2 5/2015 Hossainy et al.
9,033,863 B2 5/2015 Jarvik
9,033,909 B2 5/2015 Aihara
9,039,595 B2 5/2015 Ayre et al.
9,044,236 B2 6/2015 Nguyen et al.
9,056,159 B2 6/2015 Medvedev et al.
9,066,992 B2 6/2015 Stankus et al.
9,067,005 B2 6/2015 Ozaki et al.
9,067,006 B2 6/2015 Toellner
9,072,825 B2 7/2015 Pfeffer et al.
9,078,692 B2 7/2015 Shturman et al.
9,089,329 B2 7/2015 Hoarau et al.
9,089,634 B2 7/2015 Schumacher et al.
9,089,635 B2 7/2015 Reichenbach et al.
9,089,670 B2 7/2015 Scheckel
9,095,428 B2 8/2015 Kabir et al.
9,096,703 B2 8/2015 Li et al.
9,101,302 B2 8/2015 Mace et al.
9,125,977 B2 9/2015 Nishimura et al.
9,127,680 B2 9/2015 Yanal et al.
9,138,516 B2 9/2015 Vischer et al.
9,138,518 B2 9/2015 Campbell et al.
9,144,638 B2 9/2015 Zimmermann et al.
9,162,017 B2 10/2015 Evans et al.
9,168,361 B2 10/2015 Ehrenreich et al.
9,180,227 B2 11/2015 Ludwig et al.
9,180,235 B2 11/2015 Forsell
9,192,705 B2 11/2015 Yanal et al.
9,199,020 B2 12/2015 Siess
9,217,442 B2 12/2015 Wiessler et al.
D746,975 S 1/2016 Schenck et al.
9,227,002 B1 1/2016 Giridharan et al.
9,239,049 B2 1/2016 Jamagin et al.
9,265,870 B2 2/2016 Reichenbach et al.
9,278,189 B2 3/2016 Corbett
9,283,314 B2 3/2016 Prasad et al.
9,291,591 B2 3/2016 Simmons et al.
9,295,550 B2 3/2016 Nguyen et al.
9,295,767 B2 3/2016 Schmid et al.
9,308,302 B2 4/2016 Zeng
9,308,304 B2 4/2016 Peters et al.
9,314,558 B2 4/2016 Er
9,314,559 B2 4/2016 Smith et al.
9,328,741 B2 5/2016 Liebing
9,333,284 B2 5/2016 Thompson et al.
9,339,596 B2 5/2016 Roehn
9,345,824 B2 5/2016 Mohl et al.
9,358,329 B2 6/2016 Fitzgerald et al.
9,358,330 B2 6/2016 Schumacher
9,364,255 B2 6/2016 Weber
9,364,592 B2 6/2016 McBride et al.
9,370,613 B2 6/2016 Hsu et al.
9,375,445 B2 6/2016 Hossainy et al.
9,381,285 B2 7/2016 Ozaki et al.
9,387,284 B2 7/2016 Heilman et al.
9,409,012 B2 8/2016 Eldenschink et al.
9,416,783 B2 8/2016 Schumacher et al.
9,416,791 B2 8/2016 Toellner
9,421,311 B2 8/2016 Tanner et al.
9,433,713 B2 9/2016 Corbett et al.
9,435,450 B2 9/2016 Muennich
9,446,179 B2 9/2016 Keenan et al.
9,452,249 B2 9/2016 Kearsley et al.
9,474,840 B2 10/2016 Siess
9,486,565 B2 11/2016 Göllner et al.
9,492,601 B2 11/2016 Casas et al.
9,504,491 B2 11/2016 Callas et al.
9,511,179 B2 12/2016 Casas et al.
9,512,839 B2 12/2016 Liebing
9,522,257 B2 12/2016 Webler
9,526,818 B2 12/2016 Kearsley et al.
9,533,084 B2 1/2017 Siess et al.
9,533,085 B2 1/2017 Hanna
9,539,378 B2 1/2017 Tuseth
9,550,017 B2 1/2017 Spanier et al.
9,555,173 B2 1/2017 Spanier
9,555,175 B2 1/2017 Bulent et al.
9,555,177 B2 1/2017 Curtis et al.
9,556,873 B2 1/2017 Yanai et al.
9,561,309 B2 2/2017 Glauser et al.
9,561,313 B2 2/2017 Taskin
9,592,328 B2 3/2017 Jeevanandam et al.
9,603,983 B2 3/2017 Roehn et al.
9,603,984 B2 3/2017 Romero et al.
9,611,743 B2 4/2017 Toellner et al.
9,612,182 B2 4/2017 Olde et al.
9,616,157 B2 4/2017 Akdis
9,616,159 B2 4/2017 Anderson et al.
9,623,163 B1 4/2017 Fischi
9,631,754 B2 4/2017 Richardson et al.
9,642,984 B2 5/2017 Schumacher et al.
9,656,010 B2 5/2017 Burke
9,656,030 B1 5/2017 Webler et al.
9,662,211 B2 5/2017 Hodson et al.
9,669,141 B2 6/2017 Parker et al.
9,669,142 B2 6/2017 Spanier et al.
9,669,143 B2 6/2017 Guerrero
9,675,450 B2 6/2017 Straka et al.
9,675,738 B2 6/2017 Tanner et al.
9,675,739 B2 6/2017 Tanner et al.
9,675,742 B2 6/2017 Casas et al.
9,687,596 B2 6/2017 Poirier

(56) References Cited

U.S. PATENT DOCUMENTS 9,687,630 B2 6/2017 Basu et al.
9,700,659 B2 7/2017 Kantrowitz et al.
9,713,662 B2 7/2017 Rosenberg et al.
9,713,663 B2 7/2017 Medvedev et al.
9,715,839 B2 7/2017 Pybus et al.
9,717,615 B2 8/2017 Grandt
9,717,832 B2 8/2017 Taskin et al.
9,717,839 B2 8/2017 Hashimoto
9,726,195 B2 8/2017 Cecere et al.
9,731,058 B2 8/2017 Siebenhaar et al.
9,731,101 B2 8/2017 Bertrand et al.
9,737,361 B2 8/2017 Magana et al.
9,737,651 B2 8/2017 Wampler
9,744,280 B2 8/2017 Schade et al.
9,744,287 B2 8/2017 Bulent et al.
9,750,859 B2 9/2017 Bulent et al.
9,757,502 B2 9/2017 Burke et al.
9,770,202 B2 9/2017 Ralston et al.
9,770,543 B2 9/2017 Tanner et al.
9,771,801 B2 9/2017 Schumacher et al.
9,775,930 B2 10/2017 Michal et al.
9,782,279 B2 10/2017 Kassab
9,782,527 B2 10/2017 Thomas et al.
9,795,780 B2 10/2017 Sema et al.
9,801,987 B2 10/2017 Farnan et al.
9,801,992 B2 10/2017 Giordano et al.
9,821,098 B2 11/2017 Horvath et al.
9,821,146 B2 11/2017 Tao et al.
9,827,356 B2 11/2017 Muller et al.
9,833,314 B2 12/2017 Corbett
9,833,550 B2 12/2017 Siess
9,833,551 B2 12/2017 Criscione et al.
9,839,734 B1 12/2017 Menon et al.
9,844,618 B2 12/2017 Muller-Spanka et al.
9,850,906 B2 12/2017 Ozaki et al.
9,855,437 B2 1/2018 Nguyen et al.
9,861,504 B2 1/2018 Abunassar et al.
9,861,731 B2 1/2018 Tamburino
9,872,948 B2 1/2018 Siess
9,878,087 B2 1/2018 Richardson et al.
9,878,169 B2 1/2018 Hossainy
9,889,242 B2 2/2018 Pfeffer et al.
9,895,244 B2 2/2018 Papp et al.
9,895,475 B2 2/2018 Toellner et al.
9,907,890 B2 3/2018 Muller
9,907,892 B2 3/2018 Broen et al.
9,913,937 B2 3/2018 Schwammenthal et al.
9,918,822 B2 3/2018 Abunassar et al.
9,919,085 B2 3/2018 Throckmorton et al.
9,919,088 B2 3/2018 Bonde et al.
9,919,089 B2 3/2018 Garrigue
9,950,101 B2 4/2018 Smith et al.
9,956,410 B2 5/2018 Deem et al.
9,962,258 B2 5/2018 Seguin et al.
9,974,893 B2 5/2018 Toellner
9,974,894 B2 5/2018 Morello
9,981,078 B2 5/2018 Jin et al.
9,985,374 B2 5/2018 Hodges
9,987,407 B2 6/2018 Grant et al.
10,010,273 B2 7/2018 Sloan et al.
10,022,499 B2 7/2018 Galasso
10,028,835 B2 7/2018 Kermode et al.
10,029,037 B2 7/2018 Muller et al.
10,029,038 B2 7/2018 Hodges
10,029,039 B2 7/2018 Dague et al.
10,031,124 B2 7/2018 Galasso
10,034,972 B2 7/2018 Wampler et al.
10,039,873 B2 8/2018 Siegenthaler
10,046,146 B2 8/2018 Manderfeld et al.
10,052,419 B2 8/2018 Er
10,058,349 B2 8/2018 Gunderson et al.
10,058,641 B2 8/2018 Mollison et al.
10,058,652 B2 8/2018 Tsoukalis
10,058,653 B2 8/2018 Wang et al.
10,077,777 B2 9/2018 Horvath et al.
10,080,828 B2 9/2018 Wiesener et al.
10,080,834 B2 9/2018 Federspiel et al.
10,080,871 B2 9/2018 Schumacher et al.
10,208,763 B2 2/2019 Schumacher et al.
10,357,598 B2 7/2019 Aboul-Hosn et al.
10,569,005 B2 2/2020 Solem et al.
10,722,631 B2 7/2020 Salahieh et al.
10,881,770 B2 1/2021 Tuval et al.
10,894,115 B2 1/2021 Pfeffer et al.
11,123,538 B2 9/2021 Epple et al.
11,185,677 B2 11/2021 Salahieh et al.
11,229,784 B2 1/2022 Salahieh et al.
11,268,521 B2 3/2022 Toellner
11,280,345 B2 3/2022 Bredenbreuker et al.
11,850,413 B2 12/2023 Zeng et al.
12,017,056 B2 6/2024 Guo et al.
2001/0003802 A1 6/2001 Vitale
2001/0023369 A1 9/2001 Chobotov
2001/0046380 A1 11/2001 LeFebvre
2001/0053928 A1 12/2001 Edelman et al.
2002/0057989 A1 5/2002 Afzal et al.
2002/0058971 A1 5/2002 Zarinetchi et al.
2002/0068848 A1 6/2002 Zadini et al.
2002/0072679 A1 6/2002 Schock et al.
2002/0072779 A1 6/2002 Loeb
2002/0128709 A1 9/2002 Pless
2002/0147495 A1 10/2002 Petroff
2003/0069465 A1 4/2003 Benkowski et al.
2003/0088151 A1 5/2003 Kung et al.
2003/0131995 A1 7/2003 de Rouffignac et al.
2003/0155111 A1 8/2003 Vinegar et al.
2003/0173081 A1 9/2003 Vinegar et al.
2003/0173082 A1 9/2003 Vinegar et al.
2003/0173085 A1 9/2003 Vinegar et al.
2003/0178191 A1 9/2003 Maher et al.
2003/0209348 A1 11/2003 Ward et al.
2003/0217957 A1 11/2003 Bowman et al.
2004/0024285 A1 2/2004 Muckter
2004/0040715 A1 3/2004 Wellington et al.
2004/0097782 A1 5/2004 Korakianitis et al.
2004/0097783 A1 5/2004 Peters et al.
2004/0228724 A1 11/2004 Capone et al.
2004/0249363 A1 12/2004 Burke et al.
2005/0010077 A1 1/2005 Calderon
2005/0043805 A1 2/2005 Chudik
2005/0049696 A1 3/2005 Siess et al.
2005/0060036 A1 3/2005 Schultz et al.
2005/0113632 A1 5/2005 Ortiz et al.
2005/0119599 A1 6/2005 Kanz et al.
2005/0187616 A1 8/2005 Realyvasquez
2005/0209617 A1 9/2005 Koven et al.
2005/0220636 A1 10/2005 Henein et al.
2005/0246010 A1 11/2005 Alexander et al.
2005/0254976 A1 11/2005 Carrier et al.
2005/0256540 A1 11/2005 Silver et al.
2005/0277803 A1 12/2005 Pecor
2006/0111641 A1 5/2006 Manera et al.
2006/0116700 A1 6/2006 Crow
2006/0129082 A1 6/2006 Rozga
2006/0155158 A1 7/2006 Hosn
2006/0177343 A1 8/2006 Brian et al.
2006/0195098 A1 8/2006 Schumacher
2006/0257355 A1 11/2006 Stewart et al.
2006/0293664 A1 12/2006 Schumacher
2007/0106274 A1 5/2007 Ayre et al.
2007/0167091 A1 7/2007 Schumacher
2007/0203453 A1 8/2007 Mori et al.
2007/0213690 A1 9/2007 Phillips et al.
2007/0250148 A1 10/2007 Perry et al.
2007/0253842 A1 11/2007 Horvath et al.
2007/0265673 A1 11/2007 Ransbury et al.
2007/0270633 A1 11/2007 Cook et al.
2007/0299314 A1 12/2007 Bertolero et al.
2008/0045779 A1 2/2008 Rinaldi et al.
2008/0065014 A1 3/2008 Von Oepen et al.
2008/0076101 A1 3/2008 Hyde et al.
2008/0097273 A1 4/2008 Levin et al.
2008/0097562 A1 4/2008 Tan
2008/0119421 A1 5/2008 Tuszynski et al.

(56) References Cited

U.S. PATENT DOCUMENTS

2008/0132748 A1 6/2008 Shifflette
2008/0132749 A1 6/2008 Hegde et al.
2008/0167679 A1 7/2008 Papp
2008/0167711 A1 7/2008 Roorda
2008/0188923 A1 8/2008 Chu
2008/0200750 A1 8/2008 James
2008/0208329 A1 8/2008 Bishop et al.
2008/0228026 A1 9/2008 Manera et al.
2008/0240947 A1 10/2008 Allaire et al.
2008/0243030 A1 10/2008 Seibel et al.
2008/0275295 A1 11/2008 Gertner
2008/0275354 A1 11/2008 Thuramalla et al.
2008/0296433 A1 12/2008 Brenner et al.
2008/0300677 A1 12/2008 Schrayer
2009/0012460 A1 1/2009 Steck et al.
2009/0061072 A1 3/2009 Isch et al.
2009/0063402 A1 3/2009 Hayter
2009/0082723 A1 3/2009 Krogh et al.
2009/0143635 A1 6/2009 Benkowski et al.
2009/0171448 A1 7/2009 Eli
2009/0177028 A1 7/2009 White
2009/0182307 A1 7/2009 Yap et al.
2009/0188964 A1 7/2009 Ortov
2009/0259089 A1 10/2009 Gelbart et al.
2010/0016703 A1 1/2010 Batkin et al.
2010/0022943 A1 1/2010 Mauch et al.
2010/0042037 A1 2/2010 Felt et al.
2010/0076380 A1 3/2010 Huj
2010/0084326 A1 4/2010 Takesawa
2010/0087742 A1 4/2010 Bishop et al.
2010/0105978 A1 4/2010 Matsui et al.
2010/0152523 A1 6/2010 MacDonald et al.
2010/0152525 A1 6/2010 Weizman et al.
2010/0152526 A1 6/2010 Pacella et al.
2010/0160751 A1 6/2010 Hete et al.
2010/0184318 A1 7/2010 Bogart et al.
2010/0185220 A1 7/2010 Naghavi et al.
2010/0222635 A1 9/2010 Poirier
2010/0222878 A1 9/2010 Poirier
2010/0249489 A1 9/2010 Jarvik
2011/0004046 A1* 1/2011 Campbell .......... A61M 60/422 600/16
2011/0098548 A1 4/2011 Budiman et al.
2011/0106115 A1 5/2011 Haselby et al.
2011/0106120 A1 5/2011 Haselby et al.
2011/0178596 A1 7/2011 Hauck et al.
2011/0224655 A1 9/2011 Asirvatham et al.
2011/0297599 A1 12/2011 Lo et al.
2011/0301625 A1 12/2011 Mauch et al.
2011/0304240 A1 12/2011 Meitay et al.
2012/0022316 A1 1/2012 Aboul-Hosn et al.
2012/0028908 A1 2/2012 Viswanath et al.
2012/0039711 A1 2/2012 Roehn
2012/0109060 A1 5/2012 Kick et al.
2012/0165641 A1 6/2012 Burnett et al.
2012/0179184 A1 7/2012 Orlov
2012/0184803 A1 7/2012 Simon et al.
2012/0190918 A1 7/2012 Oepen et al.
2012/0239139 A1 9/2012 Wnendt et al.
2012/0252709 A1 10/2012 Felts et al.
2012/0289928 A1 11/2012 Wright et al.
2012/0302458 A1 11/2012 Adamczyk et al.
2012/0330683 A1 12/2012 Ledwidge et al.
2013/0023373 A1 1/2013 Janek
2013/0040407 A1 2/2013 Brophy et al.
2013/0053693 A1 2/2013 Breznock et al.
2013/0085318 A1* 4/2013 Toellner ............... A61M 60/13 600/16
2013/0144144 A1 6/2013 Laster et al.
2013/0211489 A1 8/2013 Makower et al.
2013/0233798 A1 9/2013 Wiktor et al.
2013/0245360 A1 9/2013 Schumacher
2013/0267892 A1 10/2013 Woolford
2013/0281761 A1 10/2013 Kapur
2013/0289696 A1 10/2013 Maggard et al.
2013/0303831 A1* 11/2013 Evans ................ A61M 60/865 600/16
2013/0310845 A1 11/2013 Thor et al.
2013/0317604 A1 11/2013 Min et al.
2013/0344047 A1 12/2013 Pacetti et al.
2014/0017200 A1 1/2014 Michal et al.
2014/0039465 A1 2/2014 Schulz et al.
2014/0039603 A1 2/2014 Wang
2014/0051908 A1 2/2014 Khanal et al.
2014/0058190 A1 2/2014 Gohean et al.
2014/0066693 A1 3/2014 Goldfarb et al.
2014/0128659 A1 5/2014 Heuring et al.
2014/0128795 A1 5/2014 Keren et al.
2014/0142617 A1 5/2014 Larsen et al.
2014/0148638 A1 5/2014 LaRose et al.
2014/0163664 A1 6/2014 Goldsmith
2014/0190523 A1 7/2014 Garvey et al.
2014/0194678 A1 7/2014 Wildhirt et al.
2014/0194717 A1 7/2014 Wildhirt et al.
2014/0199377 A1 7/2014 Stankus et al.
2014/0200655 A1 7/2014 Webler et al.
2014/0207232 A1 7/2014 Garrigue
2014/0228741 A1 8/2014 Frankowski et al.
2014/0243970 A1 8/2014 Yanal
2014/0255176 A1 9/2014 Bredenbreuker et al.
2014/0260551 A1 9/2014 Gray et al.
2014/0275721 A1 9/2014 Yanal et al.
2014/0275725 A1 9/2014 Schenck et al.
2014/0288354 A1 9/2014 Timms et al.
2014/0309481 A1 10/2014 Medvedev et al.
2014/0336444 A1 11/2014 Bonde
2014/0336486 A1 11/2014 Ouyang et al.
2014/0336747 A1 11/2014 Rapoza et al.
2014/0341726 A1 11/2014 Wu et al.
2014/0350328 A1 11/2014 Mohl
2014/0357938 A1 12/2014 Pilla et al.
2014/0370073 A1 12/2014 Tang et al.
2015/0005571 A1 1/2015 Jeffery et al.
2015/0018747 A1 1/2015 Michal et al.
2015/0031938 A1 1/2015 Crosby et al.
2015/0051437 A1 2/2015 Miyakoshi et al.
2015/0068069 A1 3/2015 Tran et al.
2015/0080639 A1 3/2015 Radziemski et al.
2015/0080743 A1 3/2015 Siess
2015/0087890 A1 3/2015 Spanier et al.
2015/0101645 A1 4/2015 Neville et al.
2015/0112210 A1 4/2015 Webler
2015/0119859 A1 4/2015 Cajamarca et al.
2015/0120323 A1 4/2015 Galasso et al.
2015/0134048 A1 5/2015 Ding
2015/0152878 A1 6/2015 McBride et al.
2015/0159643 A1 6/2015 Koob
2015/0174060 A1 6/2015 Heit et al.
2015/0191607 A1 7/2015 McDaniel
2015/0207331 A1 7/2015 Petersen
2015/0216685 A1 8/2015 Spence et al.
2015/0222128 A1 8/2015 Hansen
2015/0222139 A1 8/2015 Petersen et al.
2015/0226691 A1 8/2015 Wang et al.
2015/0230709 A1 8/2015 Milner et al.
2015/0231317 A1 8/2015 Schima et al.
2015/0238671 A1 8/2015 Mesallum
2015/0265757 A1 9/2015 Dowling et al.
2015/0283027 A1 10/2015 Lampe et al.
2015/0285258 A1 10/2015 Foster
2015/0290370 A1 10/2015 Crunkleton et al.
2015/0290377 A1 10/2015 Kearsley et al.
2015/0306291 A1 10/2015 Bonde et al.
2015/0320926 A1 11/2015 Fitzpatrick et al.
2015/0328382 A1 11/2015 Corbett et al.
2015/0335803 A1 11/2015 Yamane
2015/0364861 A1 12/2015 Lucke et al.
2015/0366495 A1 12/2015 Gable, III et al.
2015/0367050 A1 12/2015 Bulent et al.
2015/0368335 A1 12/2015 Banerjee et al.
2015/0374892 A1 12/2015 Yanal et al.
2016/0022887 A1 1/2016 Wampler
2016/0022890 A1 1/2016 Schwammenthal et al.
2016/0030649 A1 2/2016 Zeng

(56) References Cited

U.S. PATENT DOCUMENTS

2016/0038315 A1 2/2016 Consigny et al.
2016/0045098 A1 2/2016 Tsubouchi
2016/0045652 A1 2/2016 Comen
2016/0045654 A1 2/2016 Connor
2016/0053763 A1 2/2016 Toellner
2016/0058434 A1 3/2016 Delaloye et al.
2016/0067395 A1 3/2016 Jimenez et al.
2016/0085714 A1 3/2016 Goodnow et al.
2016/0175044 A1 6/2016 Abunassar et al.
2016/0182158 A1 6/2016 Lee et al.
2016/0184499 A1 6/2016 Ricci et al.
2016/0199543 A1 7/2016 Venkateswara-Rao
2016/0199556 A1 7/2016 Ayre et al.
2016/0199557 A1 7/2016 Bluvshtein et al.
2016/0203275 A1 7/2016 Benjamin et al.
2016/0206798 A1 7/2016 Williams et al.
2016/0220269 A1 8/2016 Labropoulos et al.
2016/0220785 A1 8/2016 Fabro
2016/0222969 A1 8/2016 Heide et al.
2016/0250399 A1 9/2016 Tiller et al.
2016/0250400 A1 9/2016 Schumacher
2016/0251720 A1 9/2016 Schulze et al.
2016/0256620 A1 9/2016 Scheckel et al.
2016/0263299 A1 9/2016 Xu et al.
2016/0271161 A1 9/2016 Dobson
2016/0271309 A1 9/2016 Throckmorton et al.
2016/0279310 A1 9/2016 Scheckel et al.
2016/0303301 A1 10/2016 Bluvshtein et al.
2016/0308403 A1 10/2016 Bluvshtein et al.
2016/0317291 A1 11/2016 Bishop et al.
2016/0317333 A1 11/2016 Ainsworth et al.
2016/0325034 A1 11/2016 Wiktor et al.
2016/0348688 A1 12/2016 Schumacher et al.
2016/0354526 A1 12/2016 Whisenant et al.
2016/0375187 A1 12/2016 Lee et al.
2017/0000361 A1 1/2017 Meyering et al.
2017/0000935 A1 1/2017 Vasilyev et al.
2017/0007552 A1 1/2017 Slepian
2017/0007762 A1 1/2017 Hayter et al.
2017/0014401 A1 1/2017 Dalton et al.
2017/0014562 A1 1/2017 Liebing
2017/0021074 A1 1/2017 Opfermann et al.
2017/0028114 A1 2/2017 Göllner et al.
2017/0028115 A1 2/2017 Muller
2017/0035952 A1 2/2017 Muller
2017/0035954 A1 2/2017 Muller et al.
2017/0037860 A1 2/2017 Toellner
2017/0043076 A1 2/2017 Wampler et al.
2017/0063143 A1 3/2017 Hoarau et al.
2017/0080136 A1 3/2017 Janeczek et al.
2017/0100527 A1 4/2017 Schwammenthal et al.
2017/0112984 A1 4/2017 Vargas Fonseca
2017/0119945 A1 5/2017 Neumann
2017/0119946 A1 5/2017 McChrystal et al.
2017/0136165 A1 5/2017 Hansen et al.
2017/0136225 A1 5/2017 Siess et al.
2017/0143883 A1 5/2017 Spence
2017/0143952 A1 5/2017 Siess et al.
2017/0157309 A1 6/2017 Begg et al.
2017/0173242 A1 6/2017 Anderson et al.
2017/0193184 A1 7/2017 Hayter et al.
2017/0196638 A1 7/2017 Serna et al.
2017/0202575 A1 7/2017 Stanfield et al.
2017/0215918 A1 8/2017 Tao et al.
2017/0224896 A1 8/2017 Graham et al.
2017/0232168 A1 8/2017 Reichenbach et al.
2017/0232169 A1 8/2017 Muller
2017/0232172 A1 8/2017 Mesallum
2017/0239407 A1 8/2017 Hayward
2017/0250575 A1 8/2017 Wong et al.
2017/0265994 A1 9/2017 Krone
2017/0274128 A1 9/2017 Tamburino et al.
2017/0281025 A9 10/2017 Glover et al.
2017/0281841 A1 10/2017 Larose et al.
2017/0281842 A1 10/2017 Larose et al.
2017/0290964 A1 10/2017 Barry
2017/0296227 A1 10/2017 Osypka
2017/0296725 A1 10/2017 Peters et al.
2017/0312106 A1 11/2017 Gomez et al.
2017/0312416 A1 11/2017 Strueber
2017/0312492 A1 11/2017 Fantuzzi et al.
2017/0319113 A1 11/2017 Hurd et al.
2017/0323713 A1 11/2017 Moeller et al.
2017/0325943 A1 11/2017 Robin et al.
2017/0333607 A1 11/2017 Zarins
2017/0333673 A1 11/2017 Tuval et al.
2017/0340788 A1 11/2017 Korakianitis et al.
2017/0340789 A1 11/2017 Bonde et al.
2017/0340790 A1 11/2017 Wiesener et al.
2017/0348470 A1 12/2017 D'Ambrosio et al.
2017/0360309 A1 12/2017 Moore et al.
2017/0361001 A1 12/2017 Canatella et al.
2017/0361011 A1 12/2017 Muennich et al.
2017/0363103 A1 12/2017 Canatella et al.
2017/0363210 A1 12/2017 Durst et al.
2017/0363620 A1 12/2017 Beshiri et al.
2017/0368246 A1 12/2017 Criscione et al.
2017/0370365 A1 12/2017 Fritz et al.
2018/0001003 A1 1/2018 Moran et al.
2018/0001007 A1 1/2018 Stratton
2018/0001012 A1 1/2018 Ardehali
2018/0001062 A1 1/2018 O'Carrol et al.
2018/0015214 A1 1/2018 Lynch
2018/0021494 A1 1/2018 Muller et al.
2018/0021495 A1 1/2018 Muller et al.
2018/0021497 A1 1/2018 Nunez et al.
2018/0028736 A1 2/2018 Wong et al.
2018/0035926 A1 2/2018 Stafford
2018/0040418 A1 2/2018 Hansen et al.
2018/0047282 A1 2/2018 He et al.
2018/0050139 A1 2/2018 Siess et al.
2018/0050140 A1 2/2018 Siess et al.
2018/0050142 A1 2/2018 Siess et al.
2018/0055383 A1 3/2018 Manera
2018/0055983 A1 3/2018 Bourque
2018/0058437 A1 3/2018 Ellers et al.
2018/0064862 A1 3/2018 Keenan et al.
2018/0071020 A1 3/2018 Laufer et al.
2018/0078159 A1 3/2018 Edelman et al.
2018/0080326 A1 3/2018 Schumacher et al.
2018/0085505 A1 3/2018 Casas
2018/0085507 A1 3/2018 Casas et al.
2018/0085509 A1 3/2018 Petersen
2018/0093026 A1 4/2018 Angwin et al.
2018/0097368 A1 4/2018 Hansen
2018/0099076 A1 4/2018 Larose
2018/0099078 A1 4/2018 Tuseth et al.
2018/0100507 A1 4/2018 Wu et al.
2018/0103611 A1 4/2018 Mainini et al.
2018/0103870 A1 4/2018 Limaye et al.
2018/0108275 A1 4/2018 Newberry et al.
2018/0110514 A1 4/2018 Hoarau et al.
2018/0114426 A1 4/2018 Lee
2018/0133380 A1 5/2018 Liebing
2018/0140759 A1 5/2018 Kaiser et al.
2018/0140801 A1 5/2018 Voss et al.
2018/0146968 A1 5/2018 Nitzan et al.
2018/0149164 A1 5/2018 Siess
2018/0149165 A1 5/2018 Siess et al.
2018/0154051 A1 6/2018 Hossainy et al.
2018/0154128 A1 6/2018 Woo et al.
2018/0161540 A1 6/2018 Fantuzzi et al.
2018/0161555 A1 6/2018 Zhadkevich
2018/0168469 A1 6/2018 Granegger
2018/0169312 A1 6/2018 Barry
2018/0169313 A1 6/2018 Schwammenthal et al.
2018/0193543 A1 7/2018 Sun
2018/0193614 A1 7/2018 Nitzan et al.
2018/0193616 A1 7/2018 Nitzan et al.
2018/0200420 A1 7/2018 Di Paola et al.
2018/0200422 A1 7/2018 Nguyen et al.
2018/0202962 A1 7/2018 Simmons et al.
2018/0207334 A1 7/2018 Siess
2018/0207337 A1 7/2018 Spence et al.

(56) References Cited

U.S. PATENT DOCUMENTS

2018/0207338 A1 7/2018 Bluvshtein et al.
2018/0226997 A1 8/2018 Jia
2018/0228953 A1 8/2018 Siess et al.
2018/0228957 A1 8/2018 Colella
2018/0242891 A1 8/2018 Bernstein et al.
2018/0242976 A1 8/2018 Kizuka
2018/0243086 A1 8/2018 Barbarino et al.
2018/0243488 A1 8/2018 Callaway et al.
2018/0243489 A1 8/2018 Haddadi
2018/0243490 A1 8/2018 Kallenbach et al.
2018/0243492 A1 8/2018 Salys
2018/0250457 A1 9/2018 Morello et al.
2018/0250458 A1 9/2018 Petersen et al.
2018/0256242 A1 9/2018 Bluvshtein et al.
2018/0256794 A1 9/2018 Rodefeld
2018/0256795 A1 9/2018 Schade et al.
2018/0256797 A1 9/2018 Schenck et al.
2018/0256798 A1 9/2018 Botterbusch et al.
2018/0256859 A1 9/2018 Korkuch
2018/0264183 A1 9/2018 Jahangir
2018/0264184 A1 9/2018 Jeffries et al.
2018/0269692 A1 9/2018 Petersen et al.
2018/0280598 A1 10/2018 Curran et al.
2018/0280599 A1 10/2018 Harjes et al.
2018/0280600 A1 10/2018 Harjes et al.
2018/0280601 A1 10/2018 Harjes et al.
2018/0280604 A1 10/2018 Hobro et al.
2018/0289295 A1 10/2018 Hoss et al.
2018/0289876 A1 10/2018 Nguyen et al.
2018/0289877 A1 10/2018 Schumacher et al.
2018/0296572 A1 10/2018 Deisher
2018/0303990 A1 10/2018 Siess et al.
2019/0030231 A1 1/2019 Aboul-Hosn et al.
2019/0070345 A1 3/2019 McBride et al.
2019/0076167 A1 3/2019 Fantuzzi et al.
2019/0083690 A1 3/2019 Siess et al.
2019/0143018 A1 5/2019 Salahleh et al.
2019/0167873 A1 6/2019 Koike et al.
2019/0209751 A1 7/2019 Tuval et al.
2019/0290822 A1 9/2019 Igarashi
2019/0321531 A1 10/2019 Cambronne et al.
2020/0029951 A1 1/2020 Bessler et al.
2020/0030510 A1 1/2020 Higgins
2020/0038568 A1 2/2020 Higgins et al.
2020/0121835 A1 4/2020 Farago et al.
2020/0237981 A1 7/2020 Tuval et al.
2020/0246527 A1 8/2020 Hildebrand et al.
2020/0316268 A1 10/2020 Antoni et al.
2020/0391014 A1 12/2020 Walters et al.
2021/0008261 A1 1/2021 Calomeni et al.
2021/0023285 A1 1/2021 Brandt
2021/0038786 A1 2/2021 Calomeni et al.
2021/0052794 A1 2/2021 Tuval et al.
2021/0113212 A1 4/2021 Lashinski et al.
2021/0121679 A1 4/2021 Mohl et al.
2021/0236797 A1 8/2021 D'Ambrosio et al.
2021/0244937 A1 8/2021 Calomeni et al.
2021/0252271 A1 8/2021 Wallin et al.
2021/0252274 A1 8/2021 Dhaliwal et al.
2021/0308444 A1 10/2021 Saul et al.
2022/0080178 A1 3/2022 Salahieh et al.
2022/0105337 A1 4/2022 Salahleh et al.
2022/0203084 A1 6/2022 Zarins et al.
2023/0109991 A1 4/2023 Hildebrand et al.
2023/0218886 A1 7/2023 Robinson et al.
2023/0264012 A1 8/2023 Brandt
2023/0390544 A1 12/2023 Hildebrand et al.
2023/0405298 A1 12/2023 Hildebrand et al.
2023/0414920 A1 12/2023 Salahleh et al.
2024/0001101 A1 1/2024 Wallin et al.
2024/0115849 A1 4/2024 Dhaliwal et al.
2024/0139499 A1 5/2024 Salahleh et al.
2024/0149046 A1 5/2024 Calomeni et al.
2024/0157117 A1 5/2024 Ryan et al.
2024/0173540 A1 5/2024 Wallin et al.
2024/0181238 A1 6/2024 Ryan et al.

FOREIGN PATENT DOCUMENTS

CA 3014105 A1 8/2017
CN 1040073 A 2/1990
CN 1008307 B 6/1990
CN 1053108 A 7/1991
CN 1105103 A 7/1995
CN 1146329 A 4/1997
CN 1179708 A 4/1998
CN 2326258 Y 6/1999
CN 1222862 A 7/1999
CN 1045058 C 9/1999
CN 1235849 A 11/1999
CN 2361290 Y 2/2000
CN 1254598 A 5/2000
CN 2386827 Y 7/2000
CN 2412579 Y 1/2001
CN 2417173 Y 1/2001
CN 1310647 A 8/2001
CN 1342497 A 4/2002
CN 1088795 C 8/2002
CN 2504815 Y 8/2002
CN 1376523 A 10/2002
CN 1097138 C 12/2002
CN 1105581 C 4/2003
CN 1421248 A 6/2003
CN 2558386 Y 7/2003
CN 1118304 C 8/2003
CN 1436048 A 8/2003
CN 1120729 C 9/2003
CN 2574609 Y 9/2003
CN 1140228 C 3/2004
CN 1161581 C 8/2004
CN 1167472 C 9/2004
CN 1527906 A 9/2004
CN 1559361 A 1/2005
CN 1559626 A 1/2005
CN 1572331 A 2/2005
CN 1202871 C 5/2005
CN 1679974 A 10/2005
CN 1694338 A 11/2005
CN 1705462 A 12/2005
CN 1239133 C 2/2006
CN 1239209 C 2/2006
CN 2754637 Y 2/2006
CN 1244381 C 3/2006
CN 1249339 C 4/2006
CN 2776418 Y 5/2006
CN 2787222 Y 6/2006
CN 1799652 A 7/2006
CN 1806774 A 7/2006
CN 1826463 A 8/2006
CN 1833735 A 9/2006
CN 1833736 A 9/2006
CN 2831716 Y 10/2006
CN 1874805 A 12/2006
CN 1301583 C 2/2007
CN 1921947 A 2/2007
CN 2880096 Y 3/2007
CN 2899800 Y 5/2007
CN 101001765 A 7/2007
CN 1329666 C 8/2007
CN 101024098 A 8/2007
CN 101031302 A 9/2007
CN 101112628 A 1/2008
CN 101121045 A 2/2008
CN 101124002 A 2/2008
CN 101132830 A 2/2008
CN 100382855 C 4/2008
CN 101256992 A 9/2008
CN 100429406 C 10/2008
CN 100439717 C 12/2008
CN 100472042 C 3/2009
CN 201208423 Y 3/2009
CN 100488577 C 5/2009

(56) References Cited

FOREIGN PATENT DOCUMENTS

| | | | |
|---|---|---|---|
| CN | 201230980 | Y | 5/2009 |
| CN | 201239369 | Y | 5/2009 |
| CN | 201246310 | Y | 5/2009 |
| CN | 101448535 | A | 6/2009 |
| CN | 101522115 | A | 9/2009 |
| CN | 101534883 | A | 9/2009 |
| CN | 201308666 | Y | 9/2009 |
| CN | 101563605 | A | 10/2009 |
| CN | 100558416 | C | 11/2009 |
| CN | 100566765 | C | 12/2009 |
| CN | 101595276 | A | 12/2009 |
| CN | 101631578 | A | 1/2010 |
| CN | 101652069 | A | 2/2010 |
| CN | 101678025 | A | 3/2010 |
| CN | 101687791 | A | 3/2010 |
| CN | 101244296 | B | 6/2010 |
| CN | 101730552 | A | 6/2010 |
| CN | 101208058 | B | 8/2010 |
| CN | 101808515 | A | 8/2010 |
| CN | 101401981 | B | 9/2010 |
| CN | 101843528 | A | 9/2010 |
| CN | 101232952 | B | 11/2010 |
| CN | 101361994 | B | 11/2010 |
| CN | 201618200 | U | 11/2010 |
| CN | 201710717 | U | 1/2011 |
| CN | 101417155 | B | 2/2011 |
| CN | 101581307 | B | 4/2011 |
| CN | 102065923 | A | 5/2011 |
| CN | 101269245 | B | 7/2011 |
| CN | 101618240 | B | 8/2011 |
| CN | 102166379 | A | 8/2011 |
| CN | 101484093 | B | 9/2011 |
| CN | 102292053 | A | 12/2011 |
| CN | 102422018 | A | 4/2012 |
| CN | 102438673 | A | 5/2012 |
| CN | 102475923 | A | 5/2012 |
| CN | 202218993 | U | 5/2012 |
| CN | 101983732 | B | 7/2012 |
| CN | 102553005 | A | 7/2012 |
| CN | 101590295 | B | 8/2012 |
| CN | 101822854 | B | 9/2012 |
| CN | 101822855 | B | 9/2012 |
| CN | 101189431 | B | 10/2012 |
| CN | 101810891 | B | 10/2012 |
| CN | 102711862 | A | 10/2012 |
| CN | 102711894 | A | 10/2012 |
| CN | 102869318 | A | 1/2013 |
| CN | 102917748 | A | 2/2013 |
| CN | 102088920 | B | 4/2013 |
| CN | 103026234 | A | 4/2013 |
| CN | 103068417 | A | 4/2013 |
| CN | 103172739 | A | 6/2013 |
| CN | 101420993 | B | 7/2013 |
| CN | 103206402 | A | 7/2013 |
| CN | 103228300 | A | 7/2013 |
| CN | 103356306 | A | 10/2013 |
| CN | 103381277 | A | 11/2013 |
| CN | 103432637 | A | 12/2013 |
| CN | 103437951 | A | 12/2013 |
| CN | 103446635 | A | 12/2013 |
| CN | 103458832 | A | 12/2013 |
| CN | 102319457 | B | 1/2014 |
| CN | 103509116 | A | 1/2014 |
| CN | 103541857 | A | 1/2014 |
| CN | 103635212 | A | 3/2014 |
| CN | 203507200 | U | 4/2014 |
| CN | 203539803 | U | 4/2014 |
| CN | 203591299 | U | 5/2014 |
| CN | 102317629 | B | 8/2014 |
| CN | 203756589 | U | 8/2014 |
| CN | 104043153 | A | 9/2014 |
| CN | 203829160 | U | 9/2014 |
| CN | 104105511 | A | 10/2014 |
| CN | 203935281 | U | 11/2014 |
| CN | 104185456 | A | 12/2014 |
| CN | 104208763 | A | 12/2014 |
| CN | 203971002 | U | 12/2014 |
| CN | 204050452 | U | 12/2014 |
| CN | 102271728 | B | 1/2015 |
| CN | 102294057 | B | 1/2015 |
| CN | 104271075 | A | 1/2015 |
| CN | 102588255 | B | 3/2015 |
| CN | 104470454 | A | 3/2015 |
| CN | 102300501 | B | 4/2015 |
| CN | 103055363 | B | 4/2015 |
| CN | 104473676 | A | 4/2015 |
| CN | 104524663 | A | 4/2015 |
| CN | 204293210 | U | 4/2015 |
| CN | 102686316 | B | 5/2015 |
| CN | 104586469 | A | 5/2015 |
| CN | 104602987 | A | 5/2015 |
| CN | 102458275 | B | 6/2015 |
| CN | 102458498 | B | 6/2015 |
| CN | 104684607 | A | 6/2015 |
| CN | 104721899 | A | 6/2015 |
| CN | 204419151 | U | 6/2015 |
| CN | 102397598 | B | 7/2015 |
| CN | 103446634 | B | 7/2015 |
| CN | 104758029 | A | 7/2015 |
| CN | 104771797 | A | 7/2015 |
| CN | 101868628 | B | 8/2015 |
| CN | 103706018 | B | 9/2015 |
| CN | 104955420 | A | 9/2015 |
| CN | 104984425 | A | 10/2015 |
| CN | 104997550 | A | 10/2015 |
| CN | 105007960 | A | 10/2015 |
| CN | 105142719 | A | 12/2015 |
| CN | 105208927 | A | 12/2015 |
| CN | 102176933 | B | 1/2016 |
| CN | 102947092 | B | 1/2016 |
| CN | 103717837 | B | 1/2016 |
| CN | 105228688 | A | 1/2016 |
| CN | 105283149 | A | 1/2016 |
| CN | 204972635 | U | 1/2016 |
| CN | 103228232 | B | 2/2016 |
| CN | 103355925 | B | 2/2016 |
| CN | 105311692 | A | 2/2016 |
| CN | 102257279 | B | 3/2016 |
| CN | 102472719 | B | 3/2016 |
| CN | 103154738 | B | 3/2016 |
| CN | 105451787 | A | 3/2016 |
| CN | 205083494 | U | 3/2016 |
| CN | 103850979 | B | 4/2016 |
| CN | 105477706 | A | 4/2016 |
| CN | 105517589 | A | 4/2016 |
| CN | 205163763 | U | 4/2016 |
| CN | 103002833 | B | 5/2016 |
| CN | 103861163 | B | 5/2016 |
| CN | 105555204 | A | 5/2016 |
| CN | 205215814 | U | 5/2016 |
| CN | 102940911 | B | 6/2016 |
| CN | 105641762 | A | 6/2016 |
| CN | 105641763 | A | 6/2016 |
| CN | 105662439 | A | 6/2016 |
| CN | 105709287 | A | 6/2016 |
| CN | 105722477 | A | 6/2016 |
| CN | 205322884 | U | 6/2016 |
| CN | 104069555 | B | 7/2016 |
| CN | 105744915 | A | 7/2016 |
| CN | 105790453 | A | 7/2016 |
| CN | 105792780 | A | 7/2016 |
| CN | 105792864 | A | 7/2016 |
| CN | 103260666 | B | 8/2016 |
| CN | 103732171 | B | 8/2016 |
| CN | 103928971 | B | 8/2016 |
| CN | 105833370 | A | 8/2016 |
| CN | 205411785 | U | 8/2016 |
| CN | 205460099 | U | 8/2016 |
| CN | 205528886 | U | 8/2016 |
| CN | 103889369 | B | 9/2016 |
| CN | 104849482 | B | 9/2016 |
| CN | 105980660 | A | 9/2016 |
| CN | 106075621 | A | 11/2016 |
| CN | 106102657 | A | 11/2016 |

(56) References Cited

FOREIGN PATENT DOCUMENTS

| | | | |
|---|---|---|---|
| CN | 205681272 | U | 11/2016 |
| CN | 205698666 | U | 11/2016 |
| CN | 205698725 | U | 11/2016 |
| CN | 205753678 | U | 11/2016 |
| CN | 106214288 | A | 12/2016 |
| CN | 106256321 | A | 12/2016 |
| CN | 205779766 | U | 12/2016 |
| CN | 106334224 | A | 1/2017 |
| CN | 205867186 | U | 1/2017 |
| CN | 205876589 | U | 1/2017 |
| CN | 103281971 | B | 2/2017 |
| CN | 106390218 | A | 2/2017 |
| CN | 103533970 | B | 3/2017 |
| CN | 104826183 | B | 3/2017 |
| CN | 106512117 | A | 3/2017 |
| CN | 106581840 | A | 4/2017 |
| CN | 104068947 | B | 5/2017 |
| CN | 106620912 | A | 5/2017 |
| CN | 106691363 | A | 5/2017 |
| CN | 106716137 | A | 5/2017 |
| CN | 106794293 | A | 5/2017 |
| CN | 104225696 | B | 6/2017 |
| CN | 104918578 | B | 6/2017 |
| CN | 105915005 | B | 6/2017 |
| CN | 106902404 | A | 6/2017 |
| CN | 106955140 | A | 7/2017 |
| CN | 206325049 | U | 7/2017 |
| CN | 206355093 | U | 7/2017 |
| CN | 105377321 | B | 8/2017 |
| CN | 107050543 | A | 8/2017 |
| CN | 107050544 | A | 8/2017 |
| CN | 107080870 | A | 8/2017 |
| CN | 107080871 | A | 8/2017 |
| CN | 107110875 | A | 8/2017 |
| CN | 206414547 | U | 8/2017 |
| CN | 206443963 | U | 8/2017 |
| CN | 103930214 | B | 9/2017 |
| CN | 104619361 | B | 9/2017 |
| CN | 104936550 | B | 9/2017 |
| CN | 105188618 | B | 9/2017 |
| CN | 107115162 | A | 9/2017 |
| CN | 107126299 | A | 9/2017 |
| CN | 107126588 | A | 9/2017 |
| CN | 107134208 | A | 9/2017 |
| CN | 107157623 | A | 9/2017 |
| CN | 103857363 | B | 10/2017 |
| CN | 104768500 | B | 10/2017 |
| CN | 105008841 | B | 10/2017 |
| CN | 105492036 | B | 10/2017 |
| CN | 107252339 | A | 10/2017 |
| CN | 107281567 | A | 10/2017 |
| CN | 206592332 | U | 10/2017 |
| CN | 107349484 | A | 11/2017 |
| CN | 206660203 | U | 11/2017 |
| CN | 105287050 | B | 12/2017 |
| CN | 105597172 | B | 12/2017 |
| CN | 105854097 | B | 12/2017 |
| CN | 107412892 | A | 12/2017 |
| CN | 107440681 | A | 12/2017 |
| CN | 107496054 | A | 12/2017 |
| CN | 104602647 | B | 1/2018 |
| CN | 106061523 | B | 1/2018 |
| CN | 107551341 | A | 1/2018 |
| CN | 206934393 | U | 1/2018 |
| CN | 107693868 | A | 2/2018 |
| CN | 107693869 | A | 2/2018 |
| CN | 107708765 | A | 2/2018 |
| CN | 207018256 | U | 2/2018 |
| CN | 106029120 | B | 3/2018 |
| CN | 107753153 | A | 3/2018 |
| CN | 107754071 | A | 3/2018 |
| CN | 107798980 | A | 3/2018 |
| CN | 107835826 | A | 3/2018 |
| CN | 107837430 | A | 3/2018 |
| CN | 107862963 | A | 3/2018 |
| CN | 207125933 | U | 3/2018 |
| CN | 207136890 | U | 3/2018 |
| CN | 105120796 | B | 4/2018 |
| CN | 105214153 | B | 4/2018 |
| CN | 107865988 | A | 4/2018 |
| CN | 107886825 | A | 4/2018 |
| CN | 107913442 | A | 4/2018 |
| CN | 107921195 | A | 4/2018 |
| CN | 107923311 | A | 4/2018 |
| CN | 108025120 | A | 5/2018 |
| CN | 108025123 | A | 5/2018 |
| CN | 108066834 | A | 5/2018 |
| CN | 207410652 | U | 5/2018 |
| CN | 104470579 | B | 6/2018 |
| CN | 105188604 | B | 6/2018 |
| CN | 105492909 | B | 6/2018 |
| CN | 105498002 | B | 6/2018 |
| CN | 106535824 | B | 6/2018 |
| CN | 108136110 | A | 6/2018 |
| CN | 108144146 | A | 6/2018 |
| CN | 108175884 | A | 6/2018 |
| CN | 106028807 | B | 7/2018 |
| CN | 106310410 | B | 7/2018 |
| CN | 108273148 | A | 7/2018 |
| CN | 108310486 | A | 7/2018 |
| CN | 108348667 | A | 7/2018 |
| CN | 207614108 | U | 7/2018 |
| CN | 105640635 | B | 8/2018 |
| CN | 105923112 | B | 8/2018 |
| CN | 108367106 | A | 8/2018 |
| CN | 108430533 | A | 8/2018 |
| CN | 108457844 | A | 8/2018 |
| CN | 108472138 | A | 8/2018 |
| CN | 108472395 | A | 8/2018 |
| CN | 108472424 | A | 8/2018 |
| CN | 207708246 | U | 8/2018 |
| CN | 207708250 | U | 8/2018 |
| CN | 105407937 | B | 9/2018 |
| CN | 105902298 | B | 9/2018 |
| CN | 106420113 | B | 9/2018 |
| CN | 106510902 | B | 9/2018 |
| CN | 108525039 | A | 9/2018 |
| CN | 108525040 | A | 9/2018 |
| CN | 108601653 | A | 9/2018 |
| CN | 108601872 | A | 9/2018 |
| CN | 108601874 | A | 9/2018 |
| CN | 108601875 | A | 9/2018 |
| CN | 207924984 | U | 9/2018 |
| CN | 106377810 | B | 10/2018 |
| EP | 96495 | B1 | 9/1986 |
| EP | 79373 | B1 | 12/1986 |
| EP | 54049 | B1 | 1/1988 |
| EP | 292510 | A4 | 8/1989 |
| EP | 167562 | B1 | 4/1990 |
| EP | 230532 | B1 | 9/1990 |
| EP | 241950 | B1 | 12/1990 |
| EP | 12977981 | | 4/1991 |
| EP | 202649 | B1 | 8/1991 |
| EP | 445782 | A1 | 9/1991 |
| EP | 464714 | A1 | 1/1992 |
| EP | 293592 | B1 | 11/1992 |
| EP | 297723 | B1 | 8/1993 |
| EP | 397668 | B1 | 3/1994 |
| EP | 39657581 | | 3/1994 |
| EP | 593574 | A1 | 4/1994 |
| EP | 378251 | B1 | 6/1994 |
| EP | 605621 | A1 | 7/1994 |
| EP | 467999 | B1 | 8/1994 |
| EP | 35028281 | | 11/1994 |
| EP | 478635 | B1 | 12/1994 |
| EP | 39772081 | | 3/1995 |
| EP | 421558 | B1 | 4/1995 |
| EP | 364799 | B1 | 5/1995 |
| EP | 660726 | A1 | 7/1995 |
| EP | 672386 | A1 | 9/1995 |
| EP | 464973 | B1 | 1/1996 |
| EP | 505270 | B1 | 1/1996 |
| EP | 34958181 | | 1/1996 |
| EP | 48010181 | | 5/1996 |

(56) References Cited

FOREIGN PATENT DOCUMENTS

| | | | |
|---|---|---|---|
| EP | 58378181 | | 5/1996 |
| EP | 583012 | B1 | 7/1996 |
| EP | 756500 | A1 | 2/1997 |
| EP | 0764448 | A2 | 3/1997 |
| EP | 767318 | A2 | 4/1997 |
| EP | 788808 | A2 | 8/1997 |
| EP | 799060 | A1 | 10/1997 |
| EP | 823567 | A1 | 2/1998 |
| EP | 832357 | A1 | 4/1998 |
| EP | 841917 | A1 | 5/1998 |
| EP | 560000 | B1 | 9/1998 |
| EP | 879012 | A1 | 11/1998 |
| EP | 925078 | A1 | 6/1999 |
| EP | 807141 | B1 | 7/1999 |
| EP | 681654 | B1 | 9/1999 |
| EP | 958066 | A1 | 11/1999 |
| EP | 964718 | A1 | 12/1999 |
| EP | 725657 | B1 | 2/2000 |
| EP | 986409 | A1 | 3/2000 |
| EP | 1007140 | A1 | 6/2000 |
| EP | 1009466 | A1 | 6/2000 |
| EP | 1027898 | A1 | 8/2000 |
| EP | 1032437 | A1 | 9/2000 |
| EP | 1045708 | A1 | 10/2000 |
| EP | 1059885 | A2 | 12/2000 |
| EP | 746712 | B1 | 10/2001 |
| EP | 1139862 | A1 | 10/2001 |
| EP | 1147317 | A1 | 10/2001 |
| EP | 1148900 | A1 | 10/2001 |
| EP | 699447 | B1 | 11/2001 |
| EP | 591896 | B1 | 2/2002 |
| EP | 731664 | B1 | 2/2002 |
| EP | 79773481 | | 2/2002 |
| EP | 1217954 | A1 | 7/2002 |
| EP | 1231981 | A1 | 8/2002 |
| EP | 950057 | B1 | 11/2002 |
| EP | 1278461 | A1 | 1/2003 |
| EP | 75176981 | | 1/2003 |
| EP | 86004681 | | 2/2003 |
| EP | 597881 | B2 | 3/2003 |
| EP | 73294981 | | 3/2003 |
| EP | 814701 | B1 | 4/2003 |
| EP | 898479 | B1 | 5/2003 |
| EP | 905379 | B1 | 5/2003 |
| EP | 655625 | B1 | 7/2003 |
| EP | 764448 | B1 | 7/2003 |
| EP | 768091 | B1 | 7/2003 |
| EP | 825888 | B1 | 12/2003 |
| EP | 1379197 | A1 | 1/2004 |
| EP | 1382366 | A1 | 1/2004 |
| EP | 868145 | B1 | 2/2004 |
| EP | 895480 | B1 | 5/2004 |
| EP | 1441777 | A2 | 8/2004 |
| EP | 91635981 | | 9/2004 |
| EP | 1481698 | A2 | 12/2004 |
| EP | 1482999 | A1 | 12/2004 |
| EP | 1291027 | B1 | 3/2005 |
| EP | 877633 | B1 | 7/2005 |
| EP | 611228 | B2 | 8/2005 |
| EP | 1212516 | B1 | 10/2005 |
| EP | 1597457 | A2 | 11/2005 |
| EP | 1261385 | B1 | 2/2006 |
| EP | 1648309 | A1 | 4/2006 |
| EP | 1354606 | B1 | 6/2006 |
| EP | 1663081 | A1 | 6/2006 |
| EP | 1321166 | B1 | 7/2006 |
| EP | 1191956 | B1 | 9/2006 |
| EP | 1722767 | A2 | 11/2006 |
| EP | 1070510 | B1 | 1/2007 |
| EP | 1317295 | B1 | 1/2007 |
| EP | 1327455 | B1 | 1/2007 |
| EP | 1776095 | A1 | 4/2007 |
| EP | 1141670 | B1 | 7/2007 |
| EP | 1807148 | A2 | 7/2007 |
| EP | 1827448 | A1 | 9/2007 |
| EP | 1374928 | B1 | 12/2007 |
| EP | 1877133 | A2 | 1/2008 |
| EP | 1379294 | B1 | 5/2008 |
| EP | 1930034 | A1 | 6/2008 |
| EP | 131884881 | | 7/2008 |
| EP | 1955725 | A2 | 8/2008 |
| EP | 135685981 | | 8/2008 |
| EP | 2058017 | A2 | 5/2009 |
| EP | 1731957 | B1 | 8/2009 |
| EP | 1173238 | B1 | 10/2009 |
| EP | 2043553 | B1 | 3/2010 |
| EP | 2158491 | A2 | 3/2010 |
| EP | 2178580 | A2 | 4/2010 |
| EP | 2182844 | A1 | 5/2010 |
| EP | 2194278 | A1 | 6/2010 |
| EP | 1471952 | B1 | 7/2010 |
| EP | 2207578 | A1 | 7/2010 |
| EP | 2216059 | A1 | 8/2010 |
| EP | 2218469 | A1 | 8/2010 |
| EP | 2219699 | A1 | 8/2010 |
| EP | 2222635 | A2 | 9/2010 |
| EP | 2222788 | A1 | 9/2010 |
| EP | 2229965 | A1 | 9/2010 |
| EP | 2235204 | A1 | 10/2010 |
| EP | 1280581 | B1 | 11/2010 |
| EP | 2246078 | A1 | 11/2010 |
| EP | 2248544 | A1 | 11/2010 |
| EP | 2252337 | A1 | 11/2010 |
| EP | 2266640 | A1 | 12/2010 |
| EP | 2269670 | A1 | 1/2011 |
| EP | 2297583 | A2 | 3/2011 |
| EP | 2298371 | A1 | 3/2011 |
| EP | 2298372 | A1 | 3/2011 |
| EP | 2298373 | A1 | 3/2011 |
| EP | 2299119 | A1 | 3/2011 |
| EP | 1464348 | B1 | 4/2011 |
| EP | 2314330 | A1 | 4/2011 |
| EP | 2314331 | A1 | 4/2011 |
| EP | 2338539 | A1 | 6/2011 |
| EP | 2338540 | A1 | 6/2011 |
| EP | 2338541 | A1 | 6/2011 |
| EP | 1654027 | B1 | 7/2011 |
| EP | 2343091 | A1 | 7/2011 |
| EP | 2347778 | A1 | 7/2011 |
| EP | 1812094 | B1 | 8/2011 |
| EP | 2349385 | A1 | 8/2011 |
| EP | 2353626 | A1 | 8/2011 |
| EP | 2356458 | A1 | 8/2011 |
| EP | 2363157 | A1 | 9/2011 |
| EP | 2366412 | A2 | 9/2011 |
| EP | 1907049 | B1 | 11/2011 |
| EP | 2388027 | A1 | 11/2011 |
| EP | 2388029 | A1 | 11/2011 |
| EP | 2399639 | A1 | 12/2011 |
| EP | 1514571 | B1 | 1/2012 |
| EP | 2407185 | A1 | 1/2012 |
| EP | 2407186 | A1 | 1/2012 |
| EP | 2407187 | A1 | 1/2012 |
| EP | 2422735 | A1 | 2/2012 |
| EP | 2322600 | B1 | 3/2012 |
| EP | 2429603 | A2 | 3/2012 |
| EP | 2459269 | A1 | 6/2012 |
| EP | 2497521 | A1 | 9/2012 |
| EP | 2140892 | B1 | 10/2012 |
| EP | 2505228 | A1 | 10/2012 |
| EP | 2150811 | B1 | 1/2013 |
| EP | 1833529 | B1 | 2/2013 |
| EP | 2554191 | A1 | 2/2013 |
| EP | 2277463 | B1 | 3/2013 |
| EP | 2564771 | A1 | 3/2013 |
| EP | 2151257 | B1 | 4/2013 |
| EP | 2575922 | A2 | 4/2013 |
| EP | 1623730 | B1 | 5/2013 |
| EP | 2606919 | A1 | 6/2013 |
| EP | 2606920 | A1 | 6/2013 |
| EP | 2607712 | A1 | 6/2013 |
| EP | 1919550 | B1 | 7/2013 |
| EP | 2620173 | A1 | 7/2013 |
| EP | 1331017 | B1 | 8/2013 |

(56) References Cited

FOREIGN PATENT DOCUMENTS

| | | | |
|---|---|---|---|
| EP | 2101840 | B1 | 9/2013 |
| EP | 2401003 | B1 | 10/2013 |
| EP | 2654878 | A2 | 10/2013 |
| EP | 2654883 | A2 | 10/2013 |
| EP | 2671083 | A1 | 12/2013 |
| EP | 1412001 | B1 | 1/2014 |
| EP | 194296581 | | 1/2014 |
| EP | 2231222 | B1 | 2/2014 |
| EP | 2697890 | A2 | 2/2014 |
| EP | 101743381 | | 3/2014 |
| EP | 1629855 | B1 | 4/2014 |
| EP | 2736581 | A2 | 6/2014 |
| EP | 2744460 | A1 | 6/2014 |
| EP | 2745869 | A1 | 6/2014 |
| EP | 1485613 | B1 | 7/2014 |
| EP | 1605988 | B1 | 8/2014 |
| EP | 2792696 | A2 | 10/2014 |
| EP | 2195043 | B1 | 12/2014 |
| EP | 1962949 | B1 | 2/2015 |
| EP | 2030641 | B1 | 2/2015 |
| EP | 2643927 | B1 | 4/2015 |
| EP | 2868331 | A2 | 5/2015 |
| EP | 2152783 | B1 | 6/2015 |
| EP | 2345439 | B1 | 6/2015 |
| EP | 146097281 | | 6/2015 |
| EP | 215056981 | | 6/2015 |
| EP | 2895215 | A2 | 7/2015 |
| EP | 1761306 | B1 | 8/2015 |
| EP | 2663347 | B1 | 8/2015 |
| EP | 2209508 | B1 | 9/2015 |
| EP | 2915129 | A1 | 9/2015 |
| EP | 2920421 | A2 | 9/2015 |
| EP | 2533732 | B1 | 11/2015 |
| EP | 1317305 | B1 | 12/2015 |
| EP | 1339443 | B1 | 1/2016 |
| EP | 2967284 | A1 | 1/2016 |
| EP | 2967547 | A1 | 1/2016 |
| EP | 2984731 | A1 | 2/2016 |
| EP | 2167158 | B1 | 3/2016 |
| EP | 2061531 | B1 | 4/2016 |
| EP | 251927481 | | 4/2016 |
| EP | 2464395 | B1 | 5/2016 |
| EP | 199625281 | | 5/2016 |
| EP | 3047873 | A1 | 7/2016 |
| EP | 3047911 | A1 | 7/2016 |
| EP | 2643053 | B1 | 8/2016 |
| EP | 2734251 | B1 | 8/2016 |
| EP | 3050537 | A1 | 8/2016 |
| EP | 1942128 | B1 | 9/2016 |
| EP | 2099509 | B1 | 9/2016 |
| EP | 2719403 | B1 | 9/2016 |
| EP | 3072210 | A1 | 9/2016 |
| EP | 3072211 | A1 | 9/2016 |
| EP | 240514081 | | 10/2016 |
| EP | 2197507 | B1 | 11/2016 |
| EP | 2538086 | B1 | 11/2016 |
| EP | 3086834 | A1 | 11/2016 |
| EP | 2806911 | B1 | 12/2016 |
| EP | 3110468 | A1 | 1/2017 |
| EP | 3113808 | A1 | 1/2017 |
| EP | 3119452 | A1 | 1/2017 |
| EP | 3120811 | A2 | 1/2017 |
| EP | 3131595 | A1 | 2/2017 |
| EP | 3131596 | A1 | 2/2017 |
| EP | 3131599 | A1 | 2/2017 |
| EP | 3131600 | A1 | 2/2017 |
| EP | 3131615 | A1 | 2/2017 |
| EP | 2594799 | B1 | 3/2017 |
| EP | 3146987 | A1 | 3/2017 |
| EP | 258512981 | | 3/2017 |
| EP | 3153190 | A1 | 4/2017 |
| EP | 3157597 | A1 | 4/2017 |
| EP | 3173110 | A1 | 5/2017 |
| EP | 2825107 | B1 | 7/2017 |
| EP | 3185924 | A1 | 7/2017 |
| EP | 3185925 | A1 | 7/2017 |
| EP | 3189526 | A1 | 7/2017 |
| EP | 3191164 | A1 | 7/2017 |
| EP | 2618001 | B1 | 8/2017 |
| EP | 3197602 | A1 | 8/2017 |
| EP | 3198677 | A1 | 8/2017 |
| EP | 3204989 | A1 | 8/2017 |
| EP | 3212250 | A1 | 9/2017 |
| EP | 3219339 | A1 | 9/2017 |
| EP | 3223880 | A1 | 10/2017 |
| EP | 3232948 | A1 | 10/2017 |
| EP | 2292282 | B1 | 11/2017 |
| EP | 2945661 | B1 | 11/2017 |
| EP | 3238764 | A1 | 11/2017 |
| EP | 3244814 | A1 | 11/2017 |
| EP | 3247420 | A1 | 11/2017 |
| EP | 3247421 | A2 | 11/2017 |
| EP | 3248628 | A1 | 11/2017 |
| EP | 188540981 | | 11/2017 |
| EP | 2136861 | B1 | 12/2017 |
| EP | 3256183 | A1 | 12/2017 |
| EP | 3256184 | A1 | 12/2017 |
| EP | 3256185 | A1 | 12/2017 |
| EP | 3256186 | A1 | 12/2017 |
| EP | 300774281 | | 1/2018 |
| EP | 3277200 | A1 | 2/2018 |
| EP | 3287155 | A1 | 2/2018 |
| EP | 2482916 | B1 | 3/2018 |
| EP | 3294367 | A1 | 3/2018 |
| EP | 294820281 | | 3/2018 |
| EP | 2945662 | B1 | 4/2018 |
| EP | 3310409 | A1 | 4/2018 |
| EP | 3222301 | B1 | 5/2018 |
| EP | 3222302 | B1 | 5/2018 |
| EP | 3313471 | A1 | 5/2018 |
| EP | 3324840 | A1 | 5/2018 |
| EP | 3325035 | A1 | 5/2018 |
| EP | 3326487 | A1 | 5/2018 |
| EP | 1990358 | B1 | 6/2018 |
| EP | 3329953 | A1 | 6/2018 |
| EP | 3335647 | A2 | 6/2018 |
| EP | 178912981 | | 6/2018 |
| EP | 3341069 | A1 | 7/2018 |
| EP | 3349839 | A1 | 7/2018 |
| EP | 2219698 | B1 | 8/2018 |
| EP | 2890420 | B1 | 8/2018 |
| EP | 3352808 | A1 | 8/2018 |
| EP | 3352835 | A1 | 8/2018 |
| EP | 3360233 | A1 | 8/2018 |
| EP | 3360515 | A1 | 8/2018 |
| EP | 3377001 | A1 | 9/2018 |
| EP | 3377002 | A1 | 9/2018 |
| EP | 3377134 | A1 | 9/2018 |
| EP | 3377135 | A1 | 9/2018 |
| EP | 3377136 | A1 | 9/2018 |
| EP | 153438181 | | 9/2018 |
| EP | 310890981 | | 9/2018 |
| EP | 2249746 | B1 | 10/2018 |
| EP | 3383300 | A1 | 10/2018 |
| EP | 3383448 | A1 | 10/2018 |
| EP | 3388005 | A1 | 10/2018 |
| EP | 298879581 | | 10/2018 |
| EP | 3542835 | A1 | 9/2019 |
| FR | 2331995 | A2 | 6/1977 |
| JP | 64-52472 | A | 2/1989 |
| JP | 02289241 | A | 11/1990 |
| JP | 04176471 | A | 6/1992 |
| JP | 04224760 | A | 8/1992 |
| JP | H05-078996 | U | 10/1993 |
| JP | H11-062856 | A | 3/1999 |
| JP | 02888609 | B2 | 5/1999 |
| JP | 02927460 | B2 | 7/1999 |
| JP | H11-244376 | A | 9/1999 |
| JP | 2000102604 | A | 4/2000 |
| JP | 2000107281 | A | 4/2000 |
| JP | 2000283062 | A | 10/2000 |
| JP | 03131696 | B2 | 2/2001 |
| JP | 2001061957 | A | 3/2001 |
| JP | 2001090687 | A | 4/2001 |

(56) References Cited

FOREIGN PATENT DOCUMENTS

| | | | |
|---|---|---|---|
| JP | 03174338 | B2 | 6/2001 |
| JP | 2001173402 | A | 6/2001 |
| JP | 2001523983 | A | 11/2001 |
| JP | 03278160 | B2 | 4/2002 |
| JP | 2002191123 | A | 7/2002 |
| JP | 03313061 | B2 | 8/2002 |
| JP | 2003047656 | A | 2/2003 |
| JP | 2003070906 | A | 3/2003 |
| JP | 2003205030 | A | 7/2003 |
| JP | 2004011525 | A | 1/2004 |
| JP | 2004016426 | A | 1/2004 |
| JP | 2004028102 | A | 1/2004 |
| JP | 2004073400 | A | 3/2004 |
| JP | 2004209240 | A | 7/2004 |
| JP | 2004278375 | A | 10/2004 |
| JP | 03612581 | B2 | 1/2005 |
| JP | 2005058617 | A | 3/2005 |
| JP | 2005192687 | A | 7/2005 |
| JP | 2005199076 | A | 7/2005 |
| JP | 2005348996 | A | 12/2005 |
| JP | 2006000631 | A | 1/2006 |
| JP | 03786289 | B2 | 6/2006 |
| JP | 03803417 | B2 | 8/2006 |
| JP | 2006280571 | A | 10/2006 |
| JP | 03854972 | B2 | 12/2006 |
| JP | 2007044302 | A | 2/2007 |
| JP | 2007075541 | A | 3/2007 |
| JP | 2007089607 | A | 4/2007 |
| JP | 2007089973 | A | 4/2007 |
| JP | 2007222670 | A | 9/2007 |
| JP | 2007236564 | A | 9/2007 |
| JP | 04016441 | B2 | 12/2007 |
| JP | 04022372 | B2 | 12/2007 |
| JP | 2008018242 | A | 1/2008 |
| JP | 04051812 | B2 | 2/2008 |
| JP | 04072721 | B2 | 4/2008 |
| JP | 04077902 | B2 | 4/2008 |
| JP | 04078245 | B2 | 4/2008 |
| JP | 04084060 | B2 | 4/2008 |
| JP | 04086185 | B2 | 5/2008 |
| JP | 04108054 | B2 | 6/2008 |
| JP | 04121709 | B2 | 7/2008 |
| JP | 04163384 | B2 | 10/2008 |
| JP | 04179634 | B2 | 11/2008 |
| JP | 2008264586 | A | 11/2008 |
| JP | 04198986 | B2 | 12/2008 |
| JP | 04209412 | B2 | 1/2009 |
| JP | 2009090882 | A | 4/2009 |
| JP | 04279494 | B2 | 6/2009 |
| JP | 04308723 | B2 | 8/2009 |
| JP | 2009178570 | A | 8/2009 |
| JP | 2009254436 | A | 11/2009 |
| JP | 2009273214 | A | 11/2009 |
| JP | 04387106 | B2 | 12/2009 |
| JP | 04391680 | B2 | 12/2009 |
| JP | 04414925 | B2 | 2/2010 |
| JP | 04440499 | B2 | 3/2010 |
| JP | 04467187 | B2 | 5/2010 |
| JP | 04468965 | B2 | 5/2010 |
| JP | 04484320 | B2 | 6/2010 |
| JP | 04512150 | B2 | 7/2010 |
| JP | 2010158532 | A | 7/2010 |
| JP | 04523961 | B2 | 8/2010 |
| JP | 04523962 | B2 | 8/2010 |
| JP | 04548450 | B2 | 9/2010 |
| JP | 04549407 | B2 | 9/2010 |
| JP | 2010246941 | A | 11/2010 |
| JP | 04611364 | B2 | 1/2011 |
| JP | 04611365 | B2 | 1/2011 |
| JP | 04646393 | B2 | 3/2011 |
| JP | 04655231 | B2 | 3/2011 |
| JP | 04656332 | B2 | 3/2011 |
| JP | 04674978 | B2 | 4/2011 |
| JP | 2011072533 | A | 4/2011 |
| JP | 2011116765 | A | 6/2011 |
| JP | 04728351 | B2 | 7/2011 |
| JP | 04741242 | B2 | 8/2011 |
| JP | 04741489 | B2 | 8/2011 |
| JP | 2011161401 | A | 8/2011 |
| JP | 04795536 | B2 | 10/2011 |
| JP | 04851333 | B2 | 1/2012 |
| JP | 04865825 | B2 | 2/2012 |
| JP | 04881154 | B2 | 2/2012 |
| JP | 04897811 | B2 | 3/2012 |
| JP | 04907028 | B2 | 3/2012 |
| JP | 04908737 | B2 | 4/2012 |
| JP | 04964854 | B2 | 7/2012 |
| JP | 04987999 | B2 | 8/2012 |
| JP | 05047447 | B2 | 10/2012 |
| JP | 05048749 | B2 | 10/2012 |
| JP | 05093869 | B2 | 12/2012 |
| JP | 05102033 | B2 | 12/2012 |
| JP | 05164558 | B2 | 3/2013 |
| JP | 05185629 | B2 | 4/2013 |
| JP | 05193059 | B2 | 5/2013 |
| JP | 05197636 | B2 | 5/2013 |
| JP | 2013078564 | A | 5/2013 |
| JP | 05215580 | B2 | 6/2013 |
| JP | 05267227 | B2 | 8/2013 |
| JP | 05286268 | B2 | 9/2013 |
| JP | 2013192711 | A | 9/2013 |
| JP | 2014004303 | A | 1/2014 |
| JP | 05427620 | B2 | 2/2014 |
| JP | 05429714 | B2 | 2/2014 |
| JP | 05440528 | B2 | 3/2014 |
| JP | 05440529 | B2 | 3/2014 |
| JP | 05461710 | B2 | 4/2014 |
| JP | 05500348 | B2 | 5/2014 |
| JP | 2014091049 | A | 5/2014 |
| JP | 2014114784 | A | 6/2014 |
| JP | 05539484 | B2 | 7/2014 |
| JP | 05557175 | B2 | 7/2014 |
| JP | 05590213 | B2 | 9/2014 |
| JP | 05596974 | B2 | 10/2014 |
| JP | 05611948 | B2 | 10/2014 |
| JP | 05633512 | B2 | 12/2014 |
| JP | 05656835 | B2 | 1/2015 |
| JP | 05673795 | B2 | 2/2015 |
| JP | 05675786 | B2 | 2/2015 |
| JP | 05676118 | B2 | 2/2015 |
| JP | 05701848 | B2 | 4/2015 |
| JP | 05711245 | B2 | 4/2015 |
| JP | 05750492 | B2 | 7/2015 |
| JP | 05781597 | B2 | 9/2015 |
| JP | 2015159947 | A | 9/2015 |
| JP | 05837162 | B2 | 12/2015 |
| JP | 05868180 | B2 | 2/2016 |
| JP | 05894116 | B2 | 3/2016 |
| JP | 05894678 | B2 | 3/2016 |
| JP | 2016028764 | A | 3/2016 |
| JP | 2016182342 | A | 10/2016 |
| JP | 06034858 | B2 | 11/2016 |
| JP | 06038018 | B2 | 12/2016 |
| JP | 06054106 | B2 | 12/2016 |
| JP | 2016202553 | A | 12/2016 |
| JP | 06083929 | B2 | 2/2017 |
| JP | 2017035323 | A | 2/2017 |
| JP | 2017517306 | A | 6/2017 |
| JP | 2017127675 | A | 7/2017 |
| JP | 06178666 | B2 | 8/2017 |
| JP | 2017159083 | A | 9/2017 |
| JP | 06220867 | B2 | 10/2017 |
| JP | 06236451 | B2 | 11/2017 |
| JP | 06267625 | B2 | 1/2018 |
| JP | 2018020199 | A | 2/2018 |
| JP | 06295204 | B2 | 3/2018 |
| JP | 06329358 | B2 | 5/2018 |
| JP | 06339371 | B2 | 6/2018 |
| JP | 06345112 | B2 | 6/2018 |
| JP | 06353787 | B2 | 7/2018 |
| JP | 06382285 | B2 | 8/2018 |
| JP | 2018122146 | A | 8/2018 |
| JP | 2018523541 | A | 8/2018 |
| WO | WO87/002894 | A2 | 5/1987 |

(56) References Cited

FOREIGN PATENT DOCUMENTS

| | | | |
|---|---|---|---|
| WO | WO88/009874 | A1 | 12/1988 |
| WO | WO92/002263 | A1 | 2/1992 |
| WO | WO92/003181 | A1 | 3/1992 |
| WO | WO96/14027 | A1 | 5/1995 |
| WO | WO95/031196 | A1 | 11/1995 |
| WO | WO96/016684 | A1 | 6/1996 |
| WO | WO98/042984 | A1 | 10/1998 |
| WO | WO00/019097 | A1 | 4/2000 |
| WO | WO00/027446 | A1 | 5/2000 |
| WO | WO00/035515 | A1 | 6/2000 |
| WO | WO01/017581 | A2 | 3/2001 |
| WO | WO01/019444 | A1 | 3/2001 |
| WO | WO01/041070 | A1 | 6/2001 |
| WO | WO01/074419 | A1 | 10/2001 |
| WO | WO01/087176 | A1 | 11/2001 |
| WO | WO01/095813 | A1 | 12/2001 |
| WO | WO02/47751 | A2 | 6/2002 |
| WO | WO02/053226 | A2 | 7/2002 |
| WO | WO02/070039 | A2 | 9/2002 |
| WO | WO02/072000 | A1 | 9/2002 |
| WO | WO02/081021 | A1 | 10/2002 |
| WO | WO03/024501 | A2 | 3/2003 |
| WO | WO03/061727 | A2 | 7/2003 |
| WO | WO03/094716 | A1 | 11/2003 |
| WO | WO03/103745 | A2 | 12/2003 |
| WO | WO2004/026394 | A1 | 4/2004 |
| WO | WO2004/034034 | A1 | 4/2004 |
| WO | WO2004/088480 | A2 | 10/2004 |
| WO | WO2004/098677 | A1 | 11/2004 |
| WO | WO2005/020848 | A2 | 3/2005 |
| WO | WO2005/033671 | A1 | 4/2005 |
| WO | WO2005/037348 | A1 | 4/2005 |
| WO | WO2005/054680 | A1 | 6/2005 |
| WO | WO2005/108796 | A1 | 11/2005 |
| WO | WO2006/040252 | A1 | 4/2006 |
| WO | WO2006/053384 | A1 | 5/2006 |
| WO | WO2006/081255 | A2 | 8/2006 |
| WO | WO2006/121698 | A2 | 11/2006 |
| WO | WO2007/008907 | A2 | 1/2007 |
| WO | WO2007/033933 | A1 | 3/2007 |
| WO | WO2007/053881 | A1 | 5/2007 |
| WO | WO2007/065408 | A2 | 6/2007 |
| WO | WO2007/092494 | A2 | 8/2007 |
| WO | WO2007/105842 | A1 | 9/2007 |
| WO | WO2007/146231 | A2 | 12/2007 |
| WO | WO2008/008427 | A2 | 1/2008 |
| WO | WVO2008/005747 | A2 | 1/2008 |
| WO | WO2008/088874 | A2 | 7/2008 |
| WO | WO2008/102015 | A1 | 8/2008 |
| WO | WO2008/121143 | A1 | 10/2008 |
| WO | WO2008/121145 | A1 | 10/2008 |
| WO | WO2008/137237 | A2 | 11/2008 |
| WO | WO2008/140034 | A1 | 11/2008 |
| WO | WO2009/017549 | A1 | 2/2009 |
| WO | WO2009035581 | A1 | 3/2009 |
| WO | WO2009/046789 | A1 | 4/2009 |
| WO | WO2009/075668 | A2 | 6/2009 |
| WO | WO2009/096991 | A1 | 8/2009 |
| WO | WO2010/025411 | A2 | 3/2010 |
| WO | WO2010/119110 | A1 | 10/2010 |
| WO | WO2011/003043 | A1 | 1/2011 |
| WO | WO2011/024928 | A1 | 3/2011 |
| WO | WO2011/035925 | A1 | 3/2011 |
| WO | WO2011/039091 | A1 | 4/2011 |
| WO | WO2011/081629 | A1 | 7/2011 |
| WO | WO2011/082212 | A1 | 7/2011 |
| WO | WO2011/085040 | A1 | 7/2011 |
| WO | WO2011/117566 | A1 | 9/2011 |
| WO | WO2011/119060 | A2 | 9/2011 |
| WO | WO2012/037506 | A2 | 3/2012 |
| WO | WO2012/051454 | A2 | 4/2012 |
| WO | WO2012/064674 | A1 | 5/2012 |
| WO | WO2012/075152 | A1 | 6/2012 |
| WO | WO2012/075262 | A1 | 6/2012 |
| WO | WO2012/087811 | A2 | 6/2012 |
| WO | WO2012/094535 | A2 | 7/2012 |
| WO | WO2012/094641 | A2 | 7/2012 |
| WO | WO2012/096716 | A2 | 7/2012 |
| WO | WO2012/112129 | A1 | 8/2012 |
| WO | WO2013/034547 | A1 | 3/2013 |
| WO | WO2013/093058 | A1 | 6/2013 |
| WO | WO2013/127182 | A1 | 9/2013 |
| WO | WO2013/134319 | A1 | 9/2013 |
| WO | WO2013/148560 | A1 | 10/2013 |
| WO | WO2013/148697 | A1 | 10/2013 |
| WO | WO2014/070458 | A1 | 5/2014 |
| WO | WO2014/096408 | A1 | 6/2014 |
| WO | WO2014/106635 | A1 | 7/2014 |
| WO | WO2014/116639 | A1 | 7/2014 |
| WO | WO2014/142754 | A1 | 9/2014 |
| WO | WO2014/143593 | A1 | 9/2014 |
| WO | WO2014/164136 | A1 | 10/2014 |
| WO | WO2014/164292 | A1 | 10/2014 |
| WO | WO2014/166128 | A1 | 10/2014 |
| WO | WO2014/169023 | A2 | 10/2014 |
| WO | WO2015/119705 | A1 | 8/2015 |
| WO | WO2015/160943 | A1 | 10/2015 |
| WO | WO2015/160979 | A1 | 10/2015 |
| WO | WO2015/171156 | A1 | 11/2015 |
| WO | WO2015/175711 | A1 | 11/2015 |
| WO | WO2015/175718 | A1 | 11/2015 |
| WO | WO2015/177793 | A2 | 11/2015 |
| WO | WO2015/187659 | A2 | 12/2015 |
| WO | WO2016/100600 | A2 | 6/2016 |
| WO | WO2016/113266 | A1 | 7/2016 |
| WO | WO2016/116630 | A2 | 7/2016 |
| WO | WO2017/001358 | A1 | 1/2017 |
| WO | WO2017/011257 | A1 | 1/2017 |
| WO | WO2017/032751 | A1 | 3/2017 |
| WO | WO2017/048733 | A1 | 3/2017 |
| WO | WO2017/060254 | A1 | 4/2017 |
| WO | WO2017/060257 | A1 | 4/2017 |
| WO | WO2017/075322 | A1 | 5/2017 |
| WO | WO2017/087380 | A1 | 5/2017 |
| WO | WO2017/120453 | A1 | 7/2017 |
| WO | WO2017/133425 | A1 | 8/2017 |
| WO | WO2017/134657 | A1 | 8/2017 |
| WO | WO2017/139113 | A1 | 8/2017 |
| WO | WO2017/139246 | A1 | 8/2017 |
| WO | WO2017/147082 | A1 | 8/2017 |
| WO | WO2017/147103 | A1 | 8/2017 |
| WO | WO2017/147291 | A1 | 8/2017 |
| WO | WO2017/151987 | A1 | 9/2017 |
| WO | WO2017/156386 | A1 | 9/2017 |
| WO | WO2017/159849 | A1 | 9/2017 |
| WO | WO2017/165372 | A1 | 9/2017 |
| WO | WO2017/178904 | A1 | 10/2017 |
| WO | WO2017/183124 | A1 | 10/2017 |
| WO | WO2017/190155 | A2 | 11/2017 |
| WO | WO2017/192119 | A1 | 11/2017 |
| WO | WO2017/196271 | A1 | 11/2017 |
| WO | WO2017/205909 | A1 | 12/2017 |
| WO | WO2017/210318 | A2 | 12/2017 |
| WO | WO2017/214118 | A1 | 12/2017 |
| WO | WO2017/214183 | A1 | 12/2017 |
| WO | WO2017/217946 | A1 | 12/2017 |
| WO | WO2018/007120 | A1 | 1/2018 |
| WO | WO2018/007471 | A1 | 1/2018 |
| WO | WO2018/017678 | A1 | 1/2018 |
| WO | WO2018/017683 | A1 | 1/2018 |
| WO | WO2018/017716 | A1 | 1/2018 |
| WO | WO2018/026764 | A1 | 2/2018 |
| WO | WO2018/026769 | A1 | 2/2018 |
| WO | WO2018/031741 | A1 | 2/2018 |
| WO | WO2018/035069 | A1 | 2/2018 |
| WO | WO2018/039124 | A1 | 3/2018 |
| WO | WO2018/039326 | A1 | 3/2018 |
| WO | WO2018/041963 | A1 | 3/2018 |
| WO | WO2018/045299 | A1 | 3/2018 |
| WO | WO2018/051091 | A1 | 3/2018 |
| WO | WO2018/052482 | A1 | 3/2018 |

(56) References Cited

FOREIGN PATENT DOCUMENTS

| | | |
|---|---|---|
| WO | WO2018/057482 A1 | 3/2018 |
| WO | WO2018/057563 A1 | 3/2018 |
| WO | WO2018/061002 A1 | 4/2018 |
| WO | WO2018/064437 A1 | 4/2018 |
| WO | WO2018/067410 A1 | 4/2018 |
| WO | WO2018/073150 A1 | 4/2018 |
| WO | WO2018/078370 A1 | 5/2018 |
| WO | WO2018/078615 A1 | 5/2018 |
| WO | WO2018/082987 A1 | 5/2018 |
| WO | WO2018/088939 A1 | 5/2018 |
| WO | WO2018/089970 A1 | 5/2018 |
| WO | WO2018/093663 A1 | 5/2018 |
| WO | WO2018/096531 A1 | 5/2018 |
| WO | WO2018/118756 A1 | 6/2018 |
| WO | WO2018/132181 A1 | 7/2018 |
| WO | WO2018/132182 A1 | 7/2018 |
| WO | WO2018/135477 A1 | 7/2018 |
| WO | WO2018/135478 A1 | 7/2018 |
| WO | WO2018/136592 A2 | 7/2018 |
| WO | WO2018/139508 A1 | 8/2018 |
| WO | WO2018/145434 A1 | 8/2018 |
| WO | WO2018/146045 A1 | 8/2018 |
| WO | WO2018/146170 A1 | 8/2018 |
| WO | WO2018/146173 A1 | 8/2018 |
| WO | WO2018/146177 A1 | 8/2018 |
| WO | WO2018/148456 A1 | 8/2018 |
| WO | WO2018/156524 A1 | 8/2018 |
| WO | WO2018/158636 A1 | 9/2018 |
| WO | WO2018/177344 A1 | 10/2018 |
| WO | WO2018/178939 A1 | 10/2018 |
| WO | WO2018/183128 A1 | 10/2018 |
| WO | WO2018/187576 A2 | 10/2018 |
| WO | WO2018/226991 A1 | 12/2018 |
| WO | WO2019/094963 A1 | 5/2019 |
| WO | WO2019/138350 A2 | 7/2019 |
| WO | WO2019/158996 A1 | 8/2019 |
| WO | WO2019/191851 A1 | 9/2019 |
| WO | WO2019/194956 A1 | 10/2019 |
| WO | WO2019/229222 A1 | 12/2019 |
| WO | WO2020/028537 A1 | 2/2020 |
| WO | WO2020/0234785 A1 | 11/2020 |
| WO | WO2021/026469 A1 | 2/2021 |
| WO | WO2021/026472 A1 | 2/2021 |
| WO | WO2021/062260 A1 | 4/2021 |
| WO | WO2021/062265 A1 | 4/2021 |
| WO | WO2021/062270 A1 | 4/2021 |
| WO | WO2021/119478 A1 | 6/2021 |
| WO | WO2021/127503 A1 | 6/2021 |
| WO | WO2021/158967 A1 | 8/2021 |
| WO | WO2021/195617 A1 | 9/2021 |
| WO | WO2021/222403 A1 | 11/2021 |
| WO | WO2021/231574 A1 | 11/2021 |
| WO | WO2021/243263 A1 | 12/2021 |

OTHER PUBLICATIONS

Jagani et al.; Dual-propeller cavopulmonary pump for assisting patients with hypoplastic right ventricle; ASAIO Joumal (American Society for Artificial Internal Organs); 10 pages; DOI: 10.1097/MAT.0000000000000907; Jan. 2019.

Park et al.; Biologically Inspired, Open, Helicoid Impeller Design for Mechanical Circulatory Assist; ASAIO Journal (American Society for Artificial Internal Organs); DOI: 10.1097/MAT.0000000000001090; Oct. 23, 2019.

Reitan et al.; First human use of the reitan catheter pump; Asaio Journal; 47(2); p. 124; Mar.-Apr. 2001.

Gupta et al.; U.S. Appl. No. 29/761,852 entitled "Intravascular blood pump external display screen or a portion thereof with graphical user interface," filed Dec. 11, 2020.

Hildebrand et al.; U.S. Appl. No. 17/615,685 entitled "Catheter blood pumps and methods of use and manufacture," filed Dec. 1, 2021.

Hildebrand et al.; U.S. Appl. No. 17/632,550 entitled Catheter blood pumps and impellers,: filed Feb. 3, 2022.

Salahieh et al.; U.S. Appl. No. 18/047,076 entitled "Intravascular fluid movement devices, systems, and methods of use," filed Oct. 17, 2022.

Merchant et al.; U.S. Appl. No. 17/997,489 entitled "Intravascular blood pumps and control thereof," filed Oct. 28, 2022.

Saul et al.; U.S. Appl. No. 17/998,614 entitled "Inflatable medical devices, methods of manufacture and use," filed Nov. 11, 2022.

Ryan et al.; U.S. Appl. No. 17/998,624 entitled "Catheter blood pumps and collapsible pump housings," filed Nov. 11, 2022.

Varghai et al.; U.S. Appl. No. 18/000,265 entitled "Intravascular blood pumps ," filed Nov. 29, 2022.

Ryan et al.; U.S. Appl. No. 17/782,675 entitled "Intravascular blood pumps, motors, and fluid control," filed Jun. 6, 2022.

Robinson et al.; U.S. Appl. No. 17/784,758 Descending aorta and vena cava blood pumps,: filed Jun. 13, 2022.

Calomeni et al.; U.S. Appl. No. 18/614,131 entitled "Intravascular blood pumps and methods of manufacture and use," filed Mar. 22, 2024.

Brandt et al.; U.S. Appl. No. 18/554,756 entitled "Catheter blood pump shrouds and assembly thereof," filed Oct. 10, 2023.

Ryan et al.; U.S. Appl. No. 18/559,231 entitled "Intravascular blood pump outflow flow disruptor," filed Nov. 6, 2023.

Salahieh et al.; U.S. Appl. No. 18/615,896 entitled "Intravascular blood pumps and methods of use and manufacture," filed Mar. 25, 2024.

Varghai et al.; U.S. Appl. No. 18/711,528 entitled "Intravascular blood pumps, motors, and fluid control," filed May 17, 2024.

Hildebrand; U.S. Appl. No. 18/710,551 entitled "Intravascular blood pumps and expandable scaffolds with stiffening members" filed May 15, 2024.

* cited by examiner 1342
1340
1330
1336
1332
1338
1334
DC Motor 1350
1356
1354
1351
1352
1353

1360
1362
1364
different pitch than
1366

1370
1382
1380
1378
1374
1376
1372
DC Motor
DC Motor
1384

154
Axillary Artery
152
blood outflow
ascending aorta
155
151
aortic valve
154
152
left ventricle
150
154
152

$L_P$
$L_{SP}$
340
$L_{SD}$
345
353
341
349
356
347
$D_I$
$D_P$
361
348
343
346
350
344
352
$L_C$ 444
443
446
442
445
440

444
446
443
442
440
445

450
451
452
453
454
455
456
457
458
459
460
461
462
463
469

CATHETER BLOOD PUMP DELIVERY, GUIDING SYSTEMS AND METHODS OF USE

CROSS REFERENCE TO RELATED APPLICATIONS

This application claims priority to U.S. Prov. App. No. 62/883,735, filed Aug. 7, 2019, the disclosure of which is incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

One aspect of the disclosure is a catheter blood pump. The blood pump may include a pump portion including an impeller housing and an impeller, wherein the pump portion includes a distal end. The pump portion may also include a rotatable drive mechanism in operable rotational communication with the impeller to cause the impeller to rotate. The blood pump may further include an axially extendable member with a distal end that is disposed further distally than the distal end of the impeller. The pump portion may also include a guide member extending through the pump portion and axially moveable relative to the pump portion, the guide member in operable axial communication with the extendable member such that axial movement of the guide member causes axial movement of the extendable member relative to the pump portion.

In any embodiment of this aspect, the guide member may be axially secured to the extendable member.

In any embodiment of this aspect, the guide member may be axially secured to an inner member of the extendable member, the extendable member optionally including an outer member, wherein the inner member is adapted to be axially moved relative to the outer member with a limited range of motion, wherein the outer member and the inner member each have one or more surfaces that are configured such that when the one or more surfaces interface, the inner member and the outer member move together distally, but when the one or more surfaces are not interfaced, the inner member can move distally without causing distal movement of the outer member.

In any embodiment of this aspect, the guide member may be adapted to be rotatable relative to the extendable member.

In any embodiment of this aspect, the guide member may not be adapted to be rotatable relative to the extendable member.

In any embodiment of this aspect, the extendable member may include a distally extending flexible tip.

In any embodiment of this aspect, the extendable member may comprise one or more surfaces that are configured and sized to interface with one or more surfaces of the distal end of the pump housing so as to prevent proximal movement of the extendable member when the one or more surfaces of the extendable member interface with the one or more surfaces of the distal end of the pump housing. A distal end of the pump portion may have a tapered configuration, narrowing in the distal direction.

In any embodiment of this aspect, the blood pump may comprise a distal stop configured to limit the distal travel of the guide member and the extendable tip relative to the pump housing. A distal stop may be disposed in an external portion of the blood pump adapted to remain outside of a patient when the impeller is in use.

In any embodiment of this aspect, the extendible member may comprise an inner seal positioned to interface with and seal against an outer surface of the distal end of the pump portion. An inner seal may have an at-rest configuration that extends further radially inward toward the guide member when the extendable member is advanced proximally away from the pump housing.

One aspect of the disclosure is a method of positioning an intravascular blood pump, comprising, while a pump portion of a catheter blood pump is disposed within a subject, advancing a guide member distally relative to the pump portion, the pump portion trackable over the guide member, wherein the guide member is secured to an axially extendable member distal to the pump portion, the axially extendable member preventing the guide member from being withdrawn from the pump portion.

One aspect of the disclosure is a method of introducing a catheter blood pump into a patient, wherein the method includes advancing a pump portion of the blood pump through an access opening in the patient, wherein when the pump portion is advanced through the access opening, an introducer catheter is not disposed in the patient.

DETAILED DESCRIPTION

The present disclosure is related to medical devices, systems, and methods of use and manufacture. Medical devices herein may include a distal pump portion (which may also be referred to herein as a working portion) adapted to be disposed within a physiologic vessel, wherein the distal pump portion includes one or more components that act upon fluid. For example, pump portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein.

Figure 1:
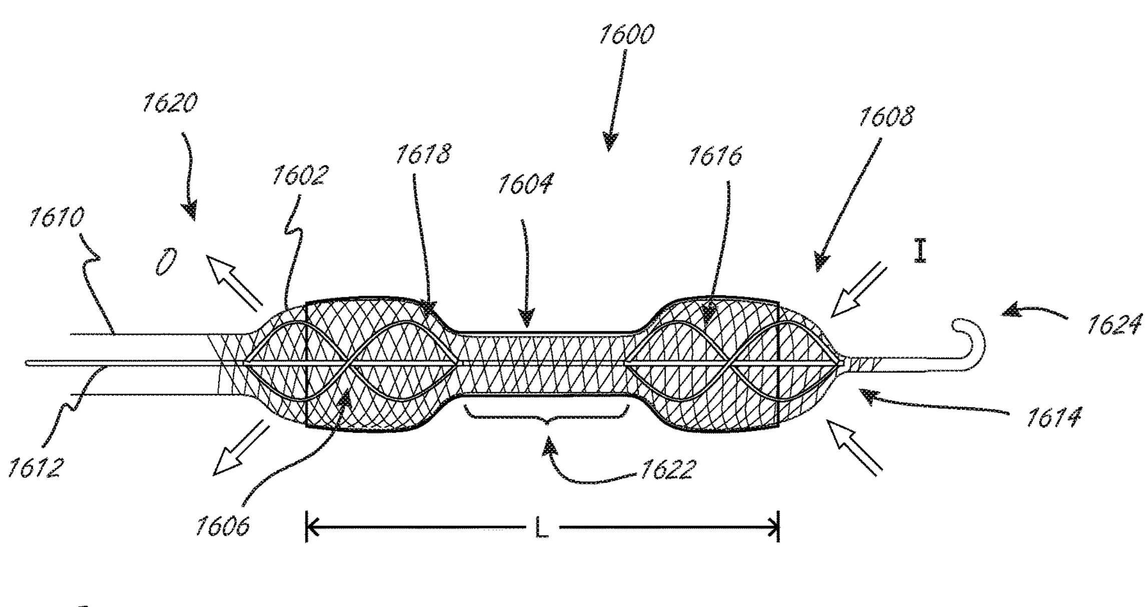
FIG. 1 is a side view of an exemplary expandable pump portion that includes an expandable impeller housing that includes a scaffold and blood conduit, and a plurality of impellers.

FIG. 1 is a side view illustrating a distal portion of an exemplary catheter blood pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can be attached to drive mechanism 1612 (e.g., a drive cable). Drive mechanism 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Pump portion 1600 also includes expandable member or expandable scaffold 1602, which in this embodiment has a proximal end 1620 that extends further proximally than a proximal end of proximal impeller 1606, and a distal end 1608 that extends further distally than a distal end 1614 of distal impeller 1616. Expandable members may also be referred to as expandable scaffolds herein. Expandable scaffold 1602 is disposed radially outside of the impellers along the axial length of the impellers. Expandable scaffold 1602 can be constructed in a manner and made from materials similar to many types of expandable structures that are known in the medical arts to be able to collapsed and expanded, examples of which are provided herein. Examples of suitable materials include, but are not limited to, polyurethane and polyurethane elastomers.

Pump portion 1600 also includes blood conduit 1604, which is coupled to expandable member 1602, has a length L, and extends axially between the impellers. Conduit 1604 creates and provides a fluid lumen between the two impellers. When in use, fluid move through the lumen provided by conduit 1604. The conduits herein are non-permeable, or they can be semipermeable, or even porous as long as they can still define a lumen. The conduits herein are also flexible, unless it is otherwise indicated. The conduits herein extend completely around (i.e., 360 degrees) at least a portion of the pump portion. In pump portion 1600, conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "O." Conduit 1604 improves impeller pumping dynamics, compared to those that working portion 1600 would have without the conduit.

Expandable member 1602 may have a variety of constructions, and made from a variety of materials. For example, expandable member 1602 may be formed similar to expandable stents or stent-like devices, or any other example provided herein. For example without limitation, expandable member 1602 could have an open-braided construction, such as a 24-end braid, although more or fewer braid wires could be used. Exemplary materials for the expandable member as well as the struts herein include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive mechanism 1612 is co-axial with the longitudinal axis in this embodiment. In use, the central region can be placed across a valve, such as an aortic valve. In some embodiments, expandable member 1602 is adapted and constructed to expand to an outermost dimension of 12-24 F (4.0-8.0 mm) where the impellers are axially within the expandable member, and to an outermost dimension of 10-20 F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive mechanism 1612 rotate within the expandable member and conduit assembly. Drive mechanism 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein for all purposes.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or 8,052,749, the disclosures of which are incorporated by reference herein.

Figure 2:
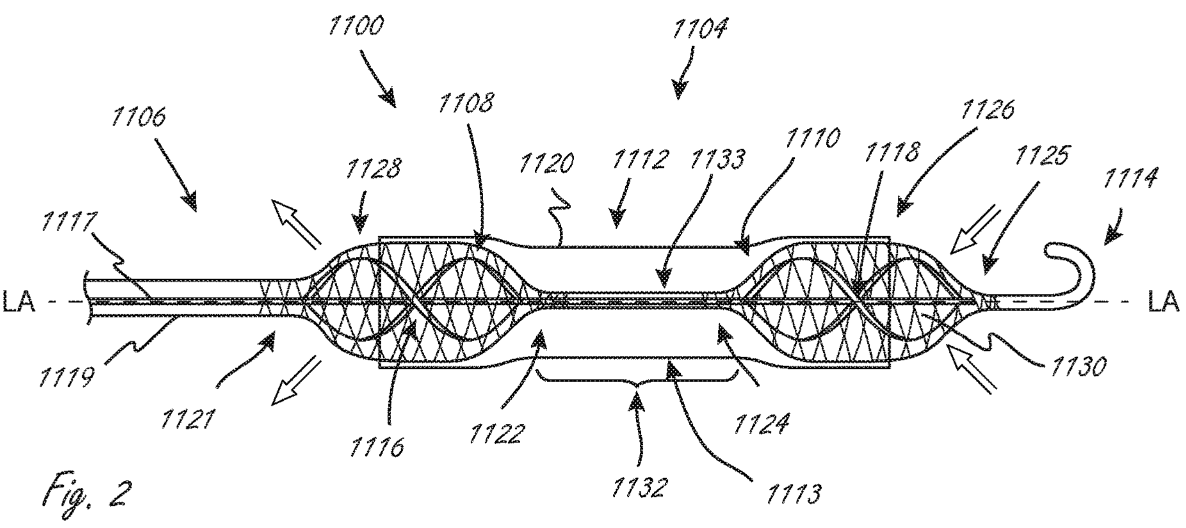
FIG. 2 is a side view of an exemplary expandable pump portion that includes an expandable impeller housing, a blood conduit, a plurality of impellers, and a plurality of expandable scaffolds sections or support members.

FIG. 2 is a side view illustrating a deployed configuration (shown extracorporally) of a distal portion of an exemplary embodiment of a catheter blood pump. Exemplary blood pump 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable scaffold or member 1108 and second expandable scaffold or member 1110, axially spaced apart along a longitudinal axis LA of working portion 1104. First scaffold 1108 and second scaffold 1110 (and any other separate scaffolds herein) may also be referenced as part of a common scaffold and referred to herein as scaffold sections. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes blood conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a blood conduit being coupled to an expandable scaffold or member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the blood conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the blood conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable scaffolds or members help maintain the blood conduit in an open configuration to create the lumen, while each also creates a working environment for an impeller, described below. Each of the expandable scaffolds, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. No. 7,841,976 or 8,052,749, the disclosures of which are incorporated by reference herein for all purposes.

FIGS. 3A-3D show an exemplary pump portion that is similar in some ways to the pump portion shown in FIG. 2.

Figure 3A:
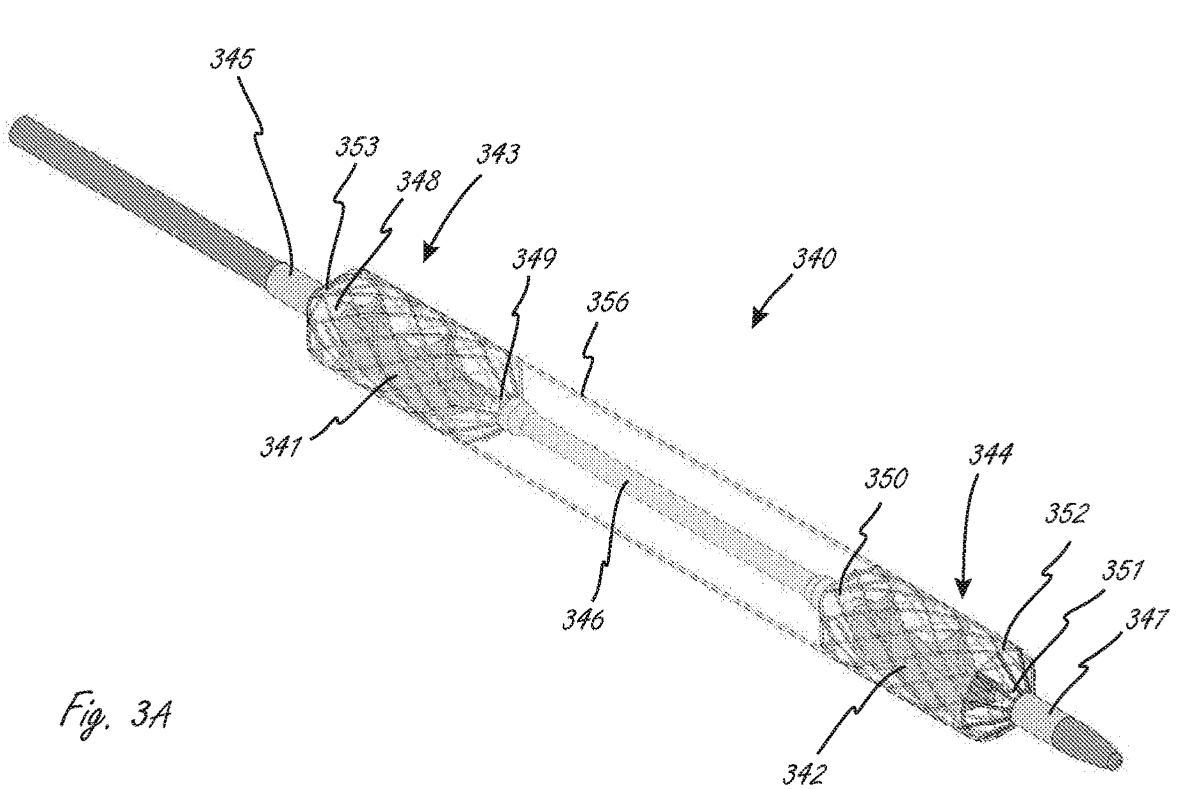
FIGS. 3A, 3B, 3C and 3D illustrate an exemplary expandable pump portion that includes a blood conduit, a plurality of impellers, and a plurality of expandable scaffold sections or support members.
Figure 3B:
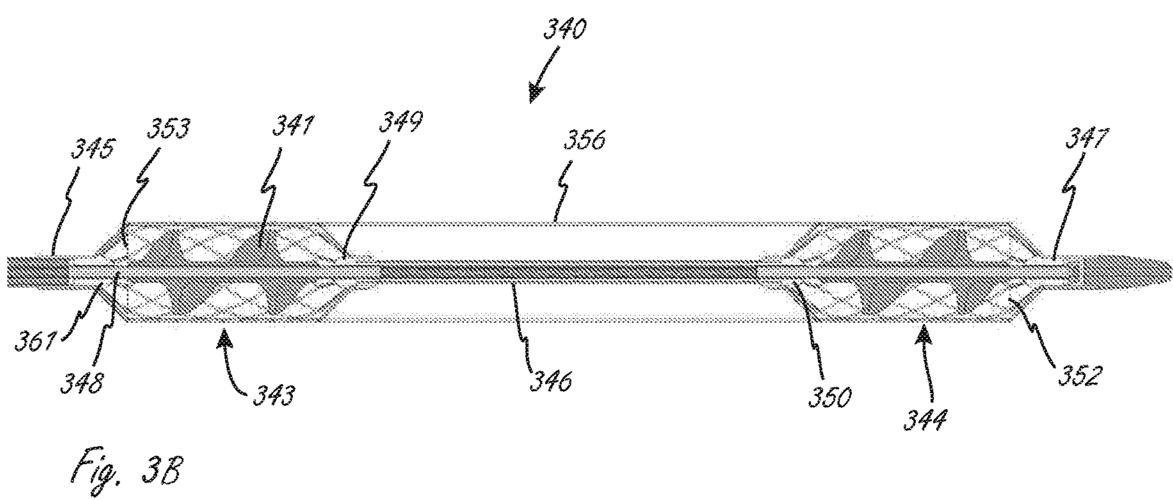
Figure 3C:
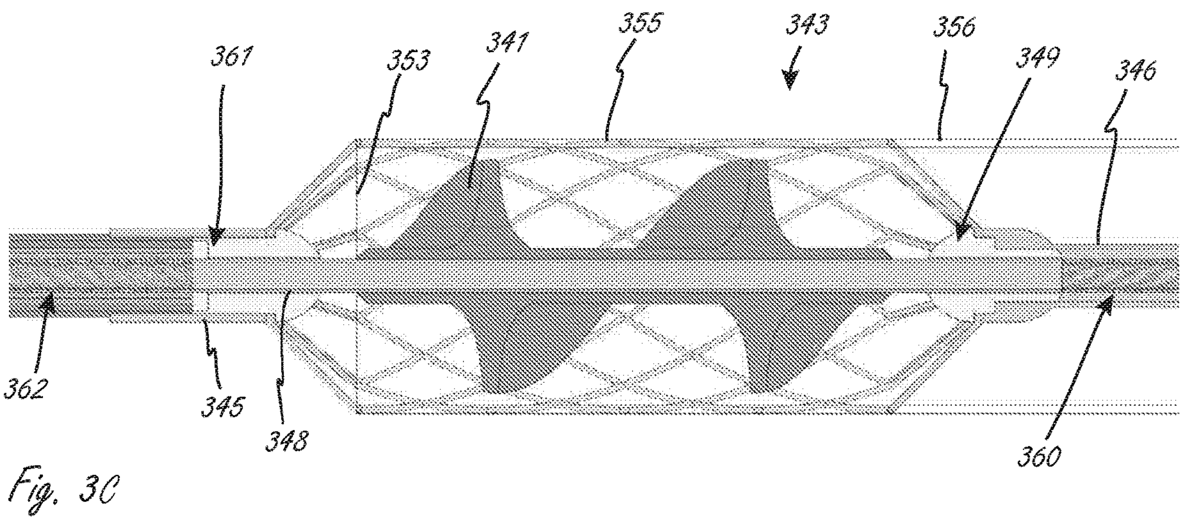
Figure 3D:
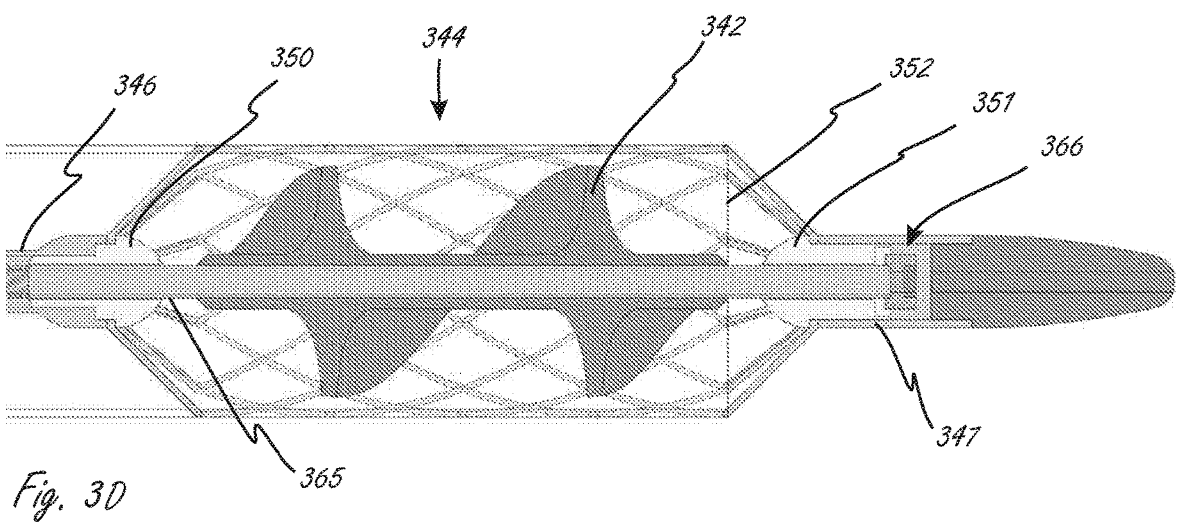

Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Pump portion 340 includes proximal expandable scaffold 343 and distal expandable scaffold 344, each of which extends radially outside of one of the impellers. The expandable scaffolds have distal and proximal ends that also extend axially beyond distal and proximal ends of the impellers, which can be seen in FIGS. 3B-3D. Coupled to the two expandable scaffolds is blood conduit 356, which has a proximal end 353 and a distal end 352. The two expandable scaffolds each include a plurality of proximal struts and a plurality of distal struts. The proximal struts in proximal expandable scaffold 343 extend to and are secured to shaft section 345, which is coupled to bearing 361, through which the drive cable extends and is configured and sized to rotate. The distal struts of proximal expandable scaffold 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts extend axially from distal expandable scaffold 344 to and are secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts extend from the distal expandable scaffold extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
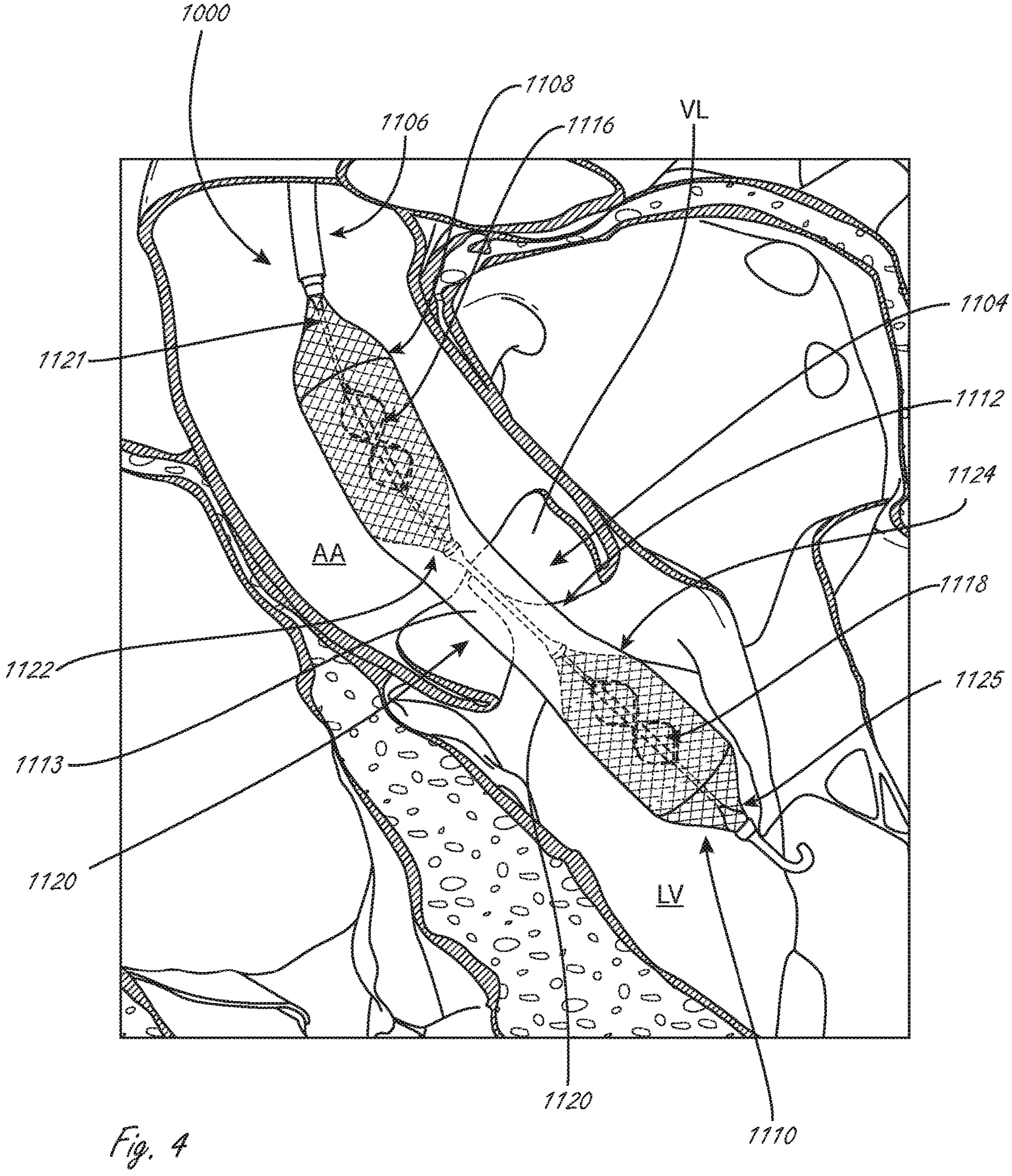
FIG. 4 illustrates an exemplary target location of an expandable pump portion, the pump portion including a blood conduit, a plurality of expandable scaffold sections or support members, and a plurality of impellers.

FIG. 4 illustrates an exemplary placement of pump portion 1104 from catheter blood pump 1000 from FIG. 2. Once difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable scaffold 1110, with continued proximal movement allowing first expandable scaffold 1108 to expand.

In this embodiment, second expandable scaffold 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable scaffolds 1108 and 1110 causes blood conduit 1112 to assume a more open configuration, as shown in FIG. 4. Thus, while in this embodiment conduit 1112 does not have the same self-expanding properties as the expandable scaffolds, the conduit will assume a deployed, more open configuration when the working end is deployed. At least a portion of central region 1113 of conduit 1112 is positioned at an aortic valve coaptation region and engages leaflets. In FIG. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable scaffold 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable scaffold 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9 F sheath and still obtain high enough flow rates when in use, which is not possible with some products currently in development and/or testing. For example, some products are too large to be able to be reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 5:
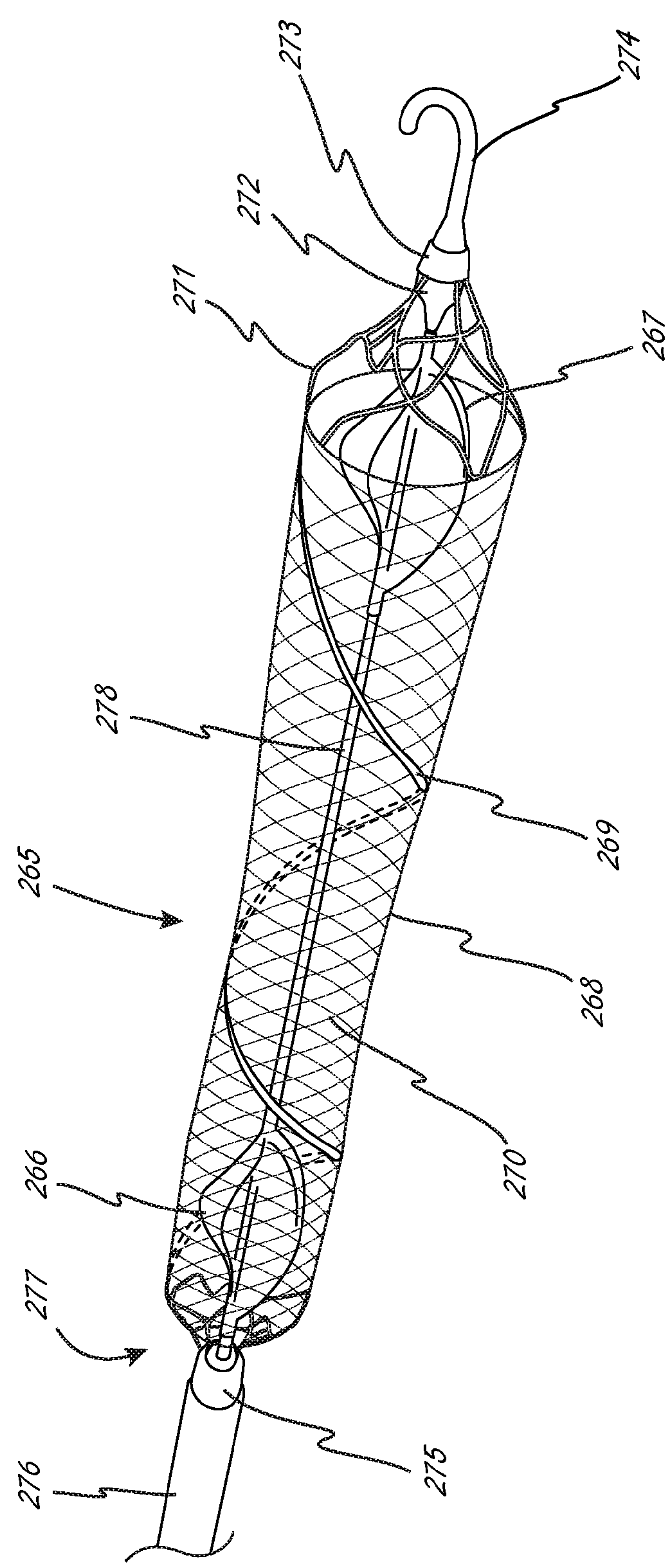
FIG. 5 illustrates an exemplary pump portion including an expandable impeller housing, a blood conduit, and a plurality of impellers.

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable scaffold or member, referred to 270 generally, and blood conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the blood conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "0." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit may extend radially within the expandable member so that inner surface of the conduit is radially within the expandable member where it is secured to the expandable member.

Any of the expandable scaffolds or member(s) herein may be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable scaffold or member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figures 6A, 6B, 6C, 7:
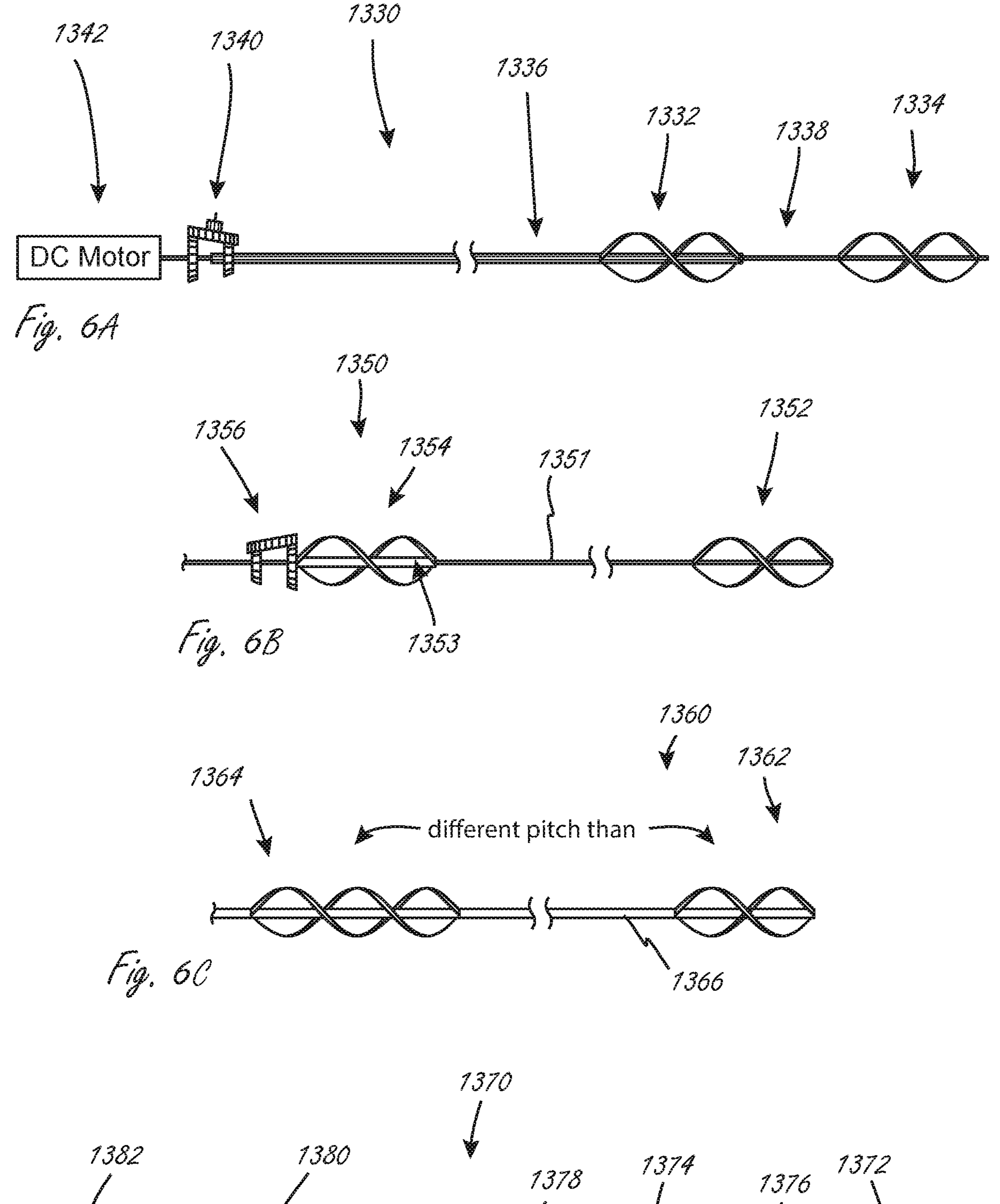
FIG. 6A illustrates at least a portion of an exemplary catheter blood pump that includes a pump portion, wherein at least two different impellers can be rotated at different speeds.
FIG. 6B illustrates at least a portion of an exemplary catheter blood pump that includes a pump portion, where at least two different impellers can be rotated at different speeds.
FIG. 6C illustrates at least a portion of an exemplary catheter blood pump that includes a pump portion with at least two impellers having different pitches.
FIG. 7 illustrates a portion of an exemplary catheter blood pump that includes a pump portion.

In any of the embodiments herein in which the catheter blood pump includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

FIG. 7 illustrates an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

In some embodiments, a common drive mechanism (e.g., cable and/or shaft) can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion may have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figures 8, 9:
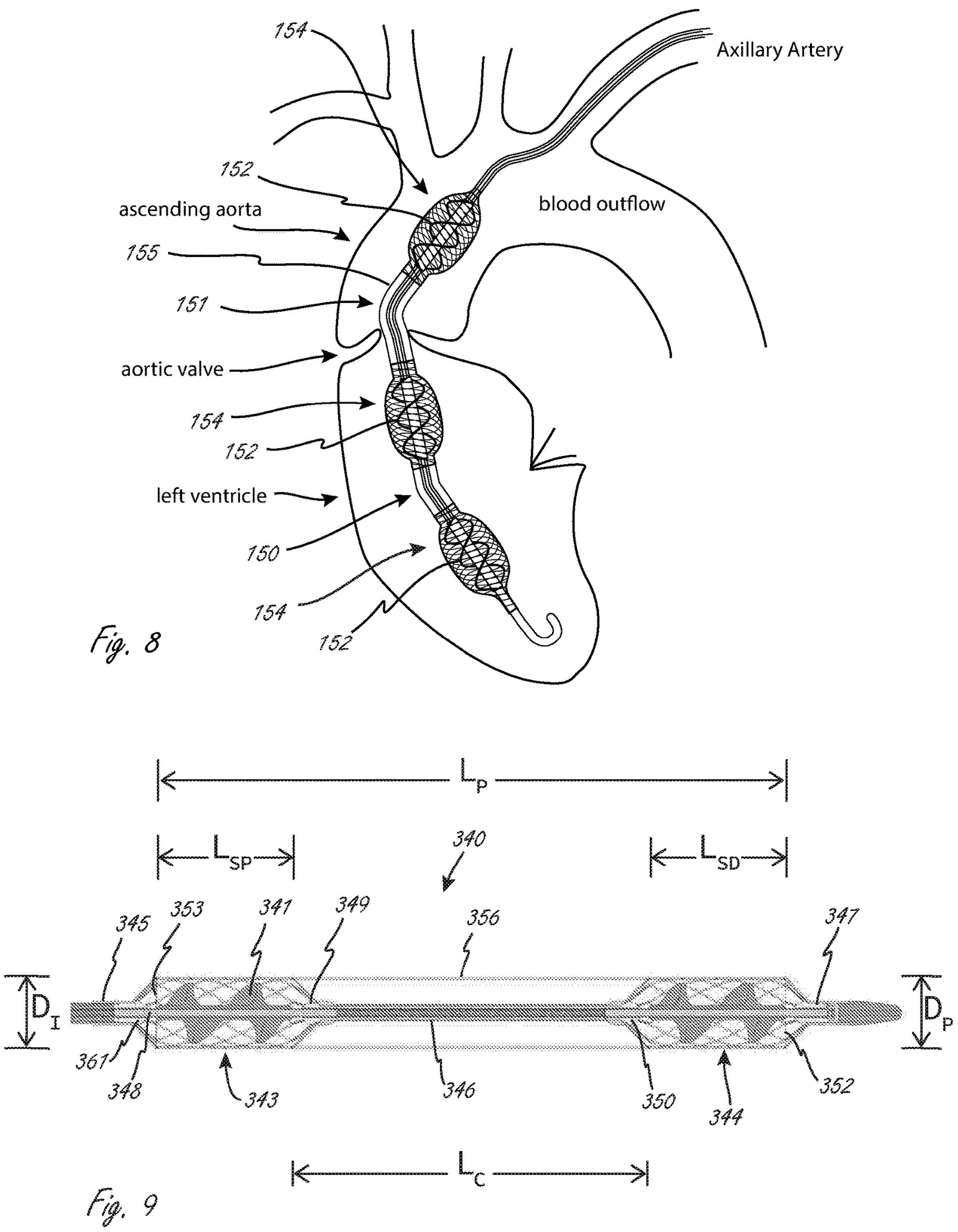
FIG. 8 illustrates an exemplary expandable pump portion including a plurality of expandable impellers, including one or more bends formed therein between adjacent impellers.
FIG. 9 illustrates an exemplary expandable pump portion comprising a plurality of impellers and a blood conduit.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. It will be appreciated from the description herein, however, that the pump may be introduced and tracked into position in various manners including a femoral approach over the aortic arch.

One aspect of the disclosure is a catheter blood pump that includes a distal impeller axially spaced from a proximal impeller. Distal and proximal impellers may be axially spaced from each other. For example, the distal and proximal impellers may be connected solely by their individual attachment to a common drive mechanism. This is different from a single impeller having multiple blade rows or sections. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. It can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

Any of the pump portions herein that include a plurality of impellers may also include more than two impellers, such as three, four, or five impellers (for example).

Figure 10:
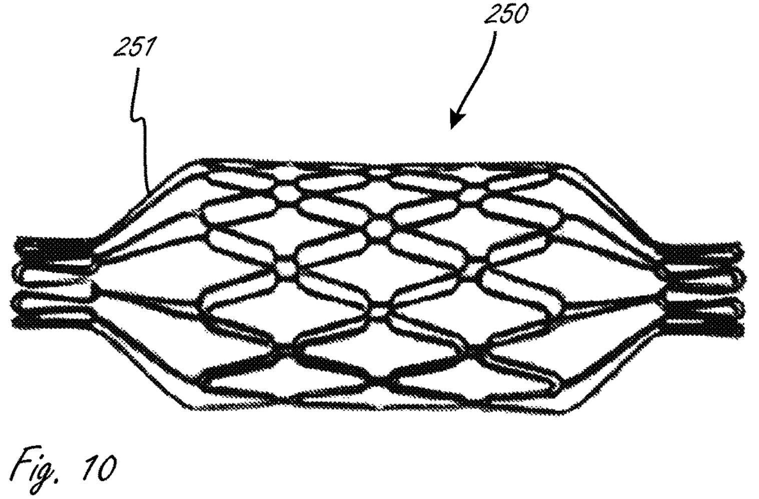
FIG. 10 illustrates an exemplary scaffold design and exemplary struts.

FIG. 10 illustrates an expandable scaffold 250 that may be one of at least two expandable scaffolds of a pump portion, such as the expandable scaffolds in FIGS. 3A-3D, wherein each expandable scaffold at least partially surrounds an impeller. The scaffold design in FIG. 10 has proximal struts 251 (only one labeled) extending axially therefrom. Having a separate expandable scaffold 250 for each impeller provides for the ability to have different geometries for any of the individual impellers. Additionally, this design reduces the amount of scaffold material (e.g., Nitinol) over the length of the expandable blood conduit, which may offer increased tracking when sheathed. A potential challenge with these designs may include creating a continuous membrane between the expandable scaffolds in the absence of an axially extending scaffolding material (see FIG. 3A). Any other aspect of the expandable scaffolds or members herein, such as those described in FIGS. 3A-3D, may be incorporated by reference into this exemplary design. Struts 251 may be disposed at a pump inflow or outflow. Struts 251 may be proximal struts or they may be distal struts.

Figure 11:
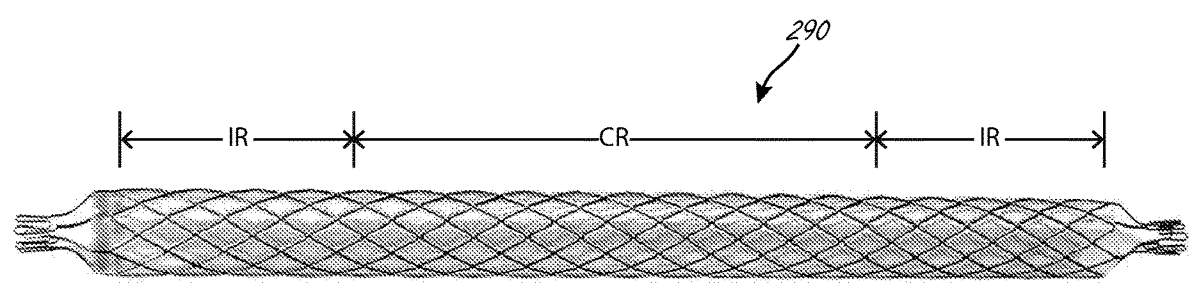
FIG. 11 illustrate an exemplary scaffold design and exemplary struts.

FIG. 11 show an exemplary scaffold along an length of the blood conduit. Central region "CR" may be axially between proximal and distal impellers. Central region "CR" flexibility is increased relative to scaffold impeller regions "IR" due to breaks or discontinuities in the scaffold pattern in the central region. The scaffold has relatively more rigid impeller sections "IR" adjacent the central region where impellers may be disposed (not shown). The relatively increased rigidity in the impeller regions IR may help maintain tip gap and impeller concentricity. This pump scaffold pattern provides for a flexibility distribution, along its length, of a proximal section of relatively less flexibility ("IW"), a central region "CR" of relatively higher flexibility, and a distal section "IR" of relatively less flexibility than the central region. The relatively less flexible sections (i.e., the two IR regions) are where proximal and distal impellers may be disposed (not shown but other embodiments are fully incorporated herein in this regard), with a relatively more flexible region in between. Exemplary benefits of the relative flexibility in these respective sections are described elsewhere herein. FIG. 11 is an example of a scaffold that is continuous from a first end region to a second end region, even though there are breaks or discontinuities in some locations of the scaffold. There is at least one line that can be traced along a continuous structural path from a first end region to a second end region.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different. Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 12A:
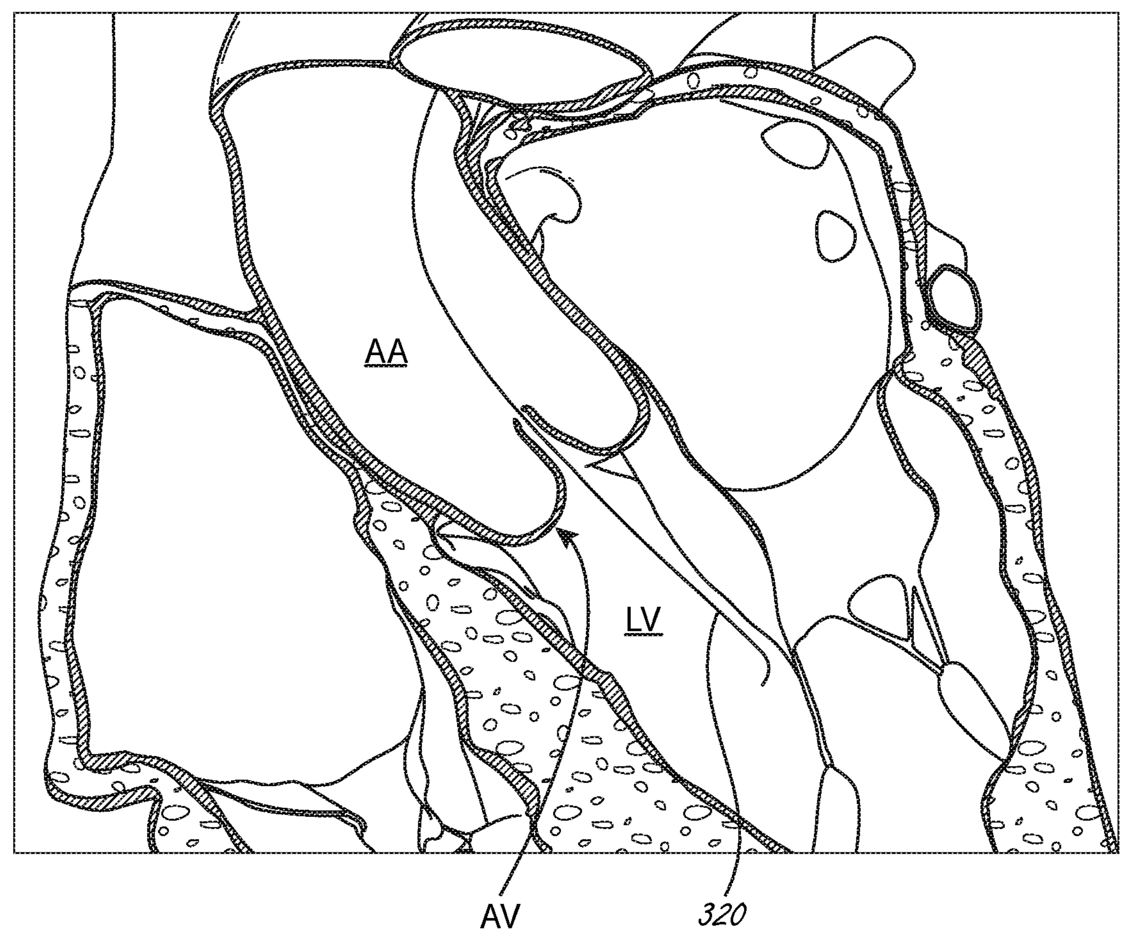
FIGS. 12A-12F illustrate an exemplary sequence of steps that may be performed to deploy an exemplary pump portion of a catheter blood pump.
Figure 12B:
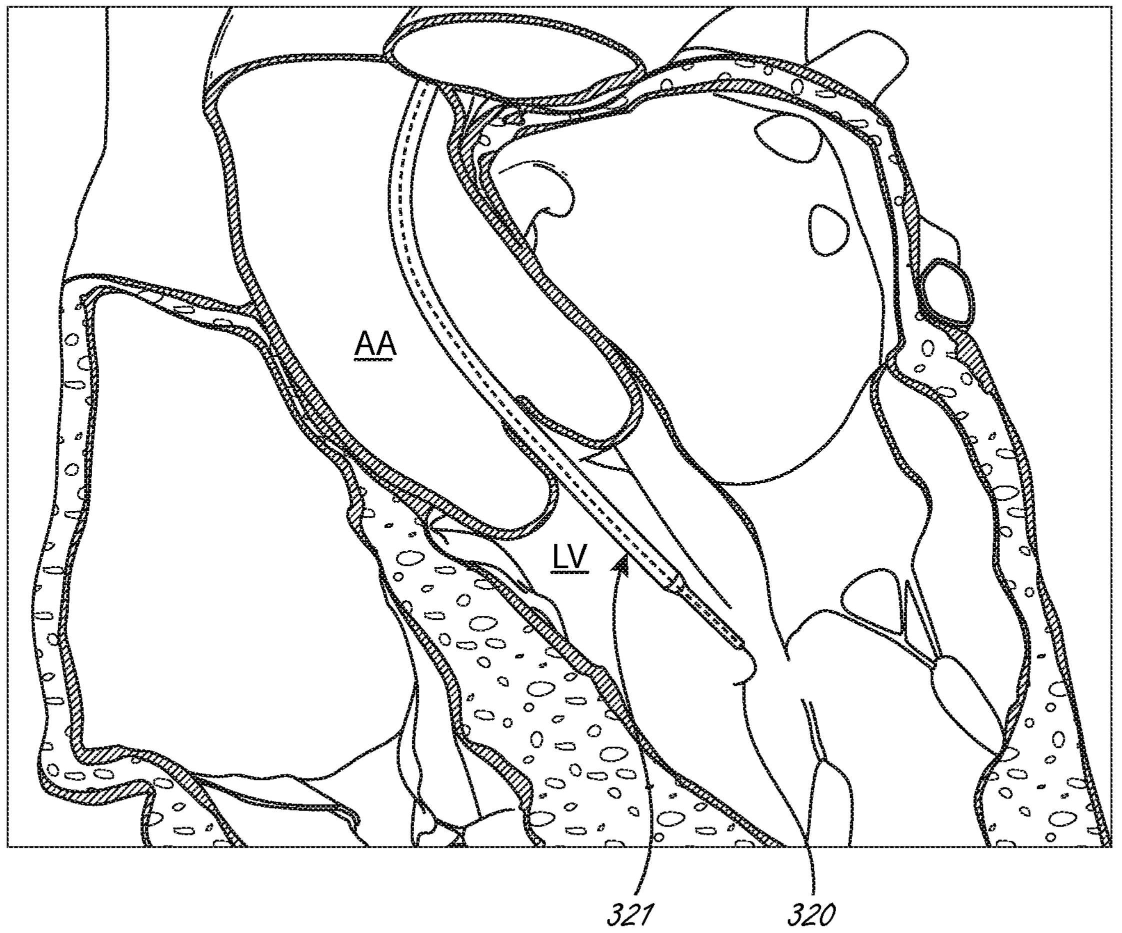

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 12A), and the blood pump 321 (including a catheter, catheter sheath, and pump portion within the sheath; see FIG. 12B) can be advanced over the second wire towards a target location, such as spanning an aortic valve "AV," and into a target location (e.g., left ventricle "LV"), using, for example, one or more radiopaque markers to position the blood pump.

Figure 12C:
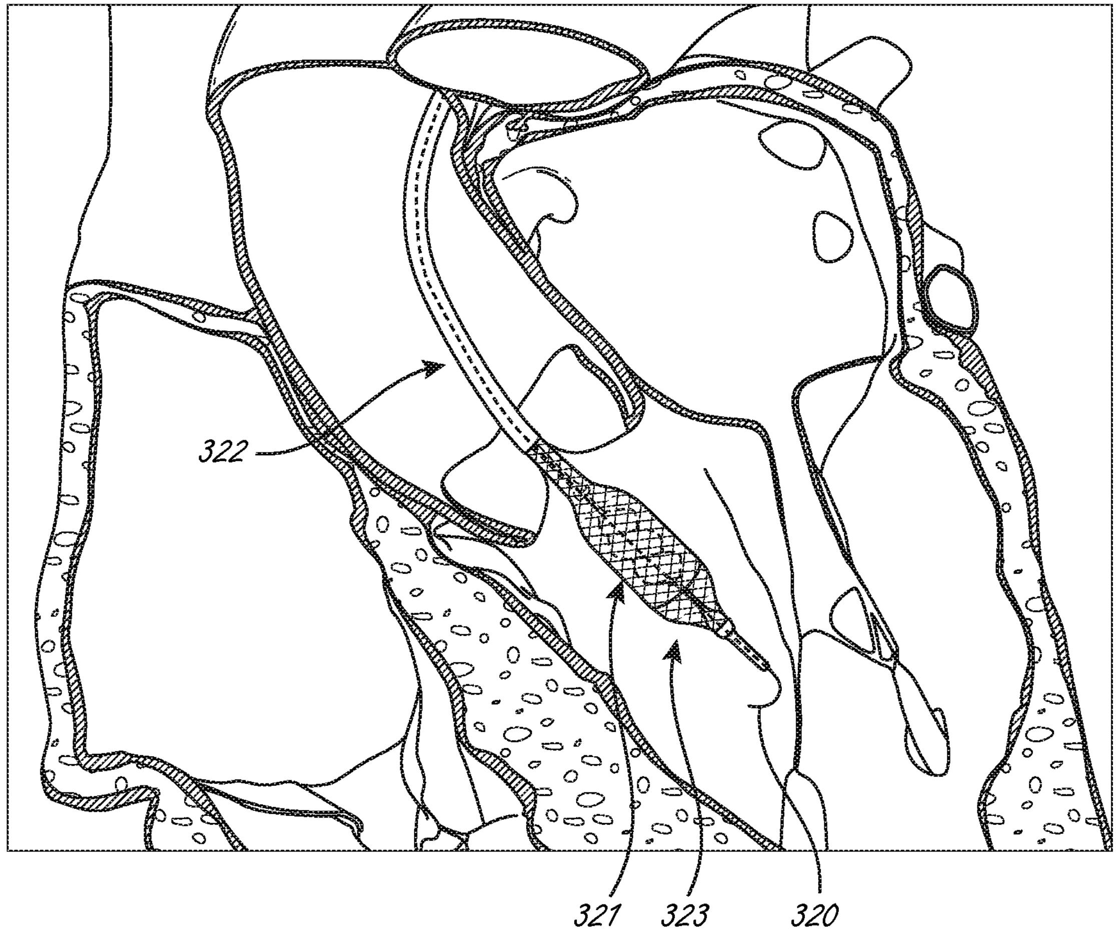
Figure 12D:
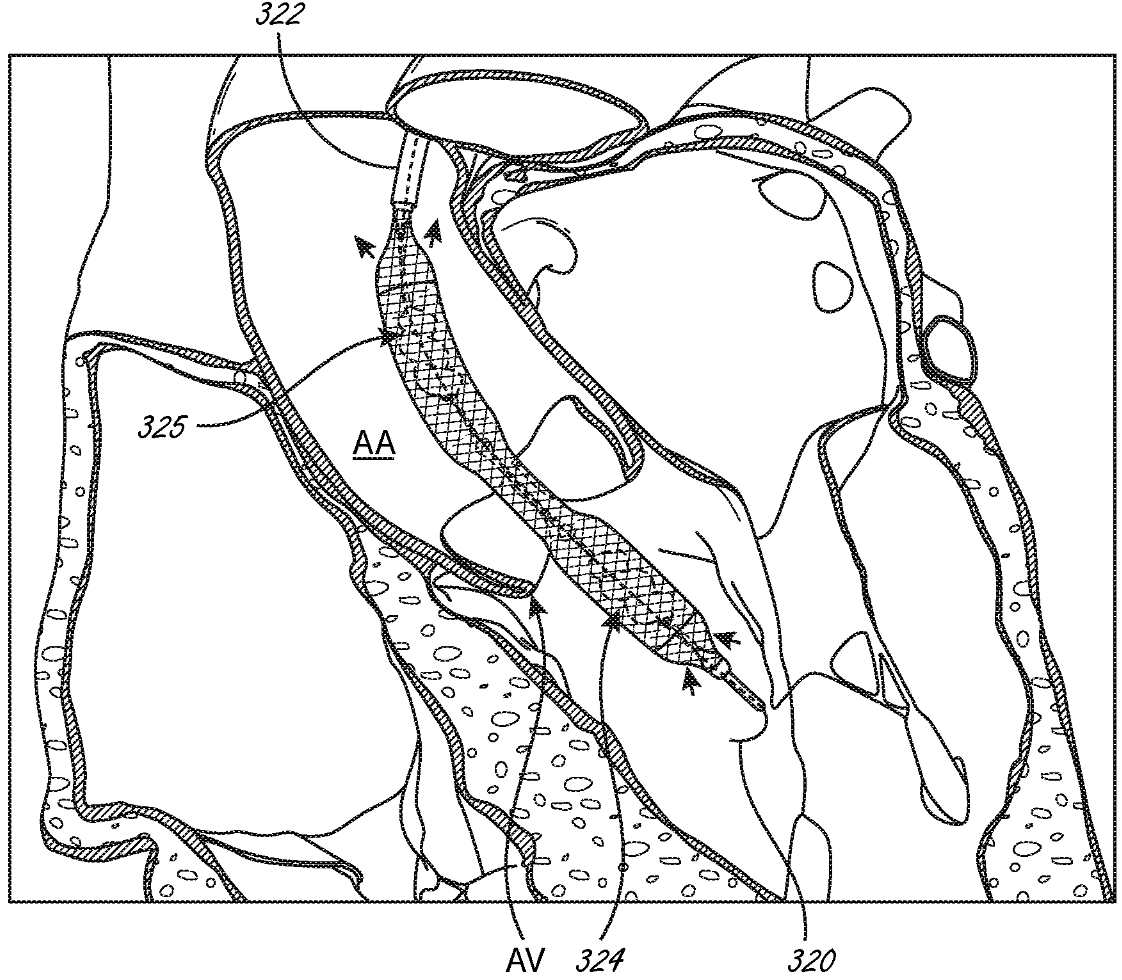

Once proper placement is confirmed, the catheter sheath 322 (see FIG. 12C) can be retracted, exposing first a distal region of the pump portion. In FIG. 12C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 12D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta ("AA").

Figure 12E:
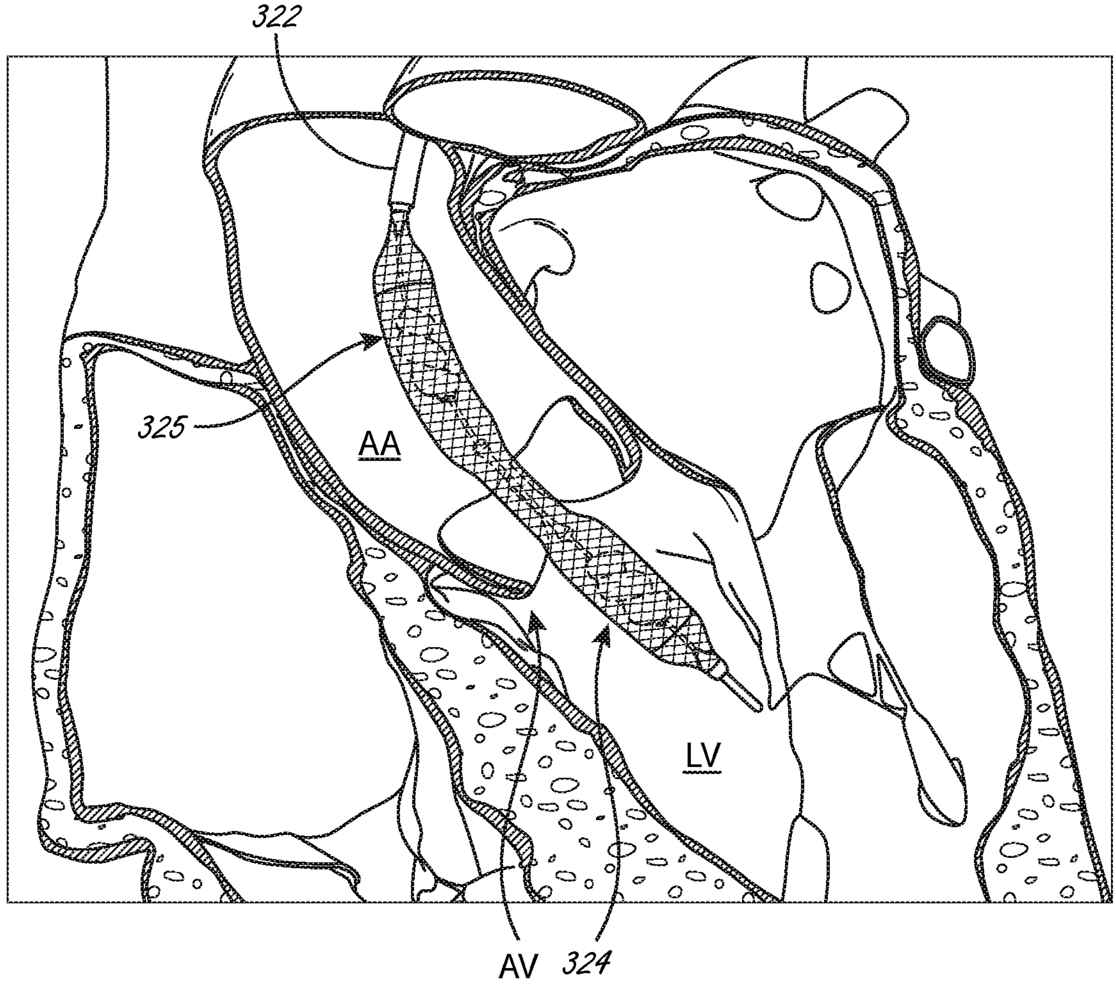
Figure 12F:
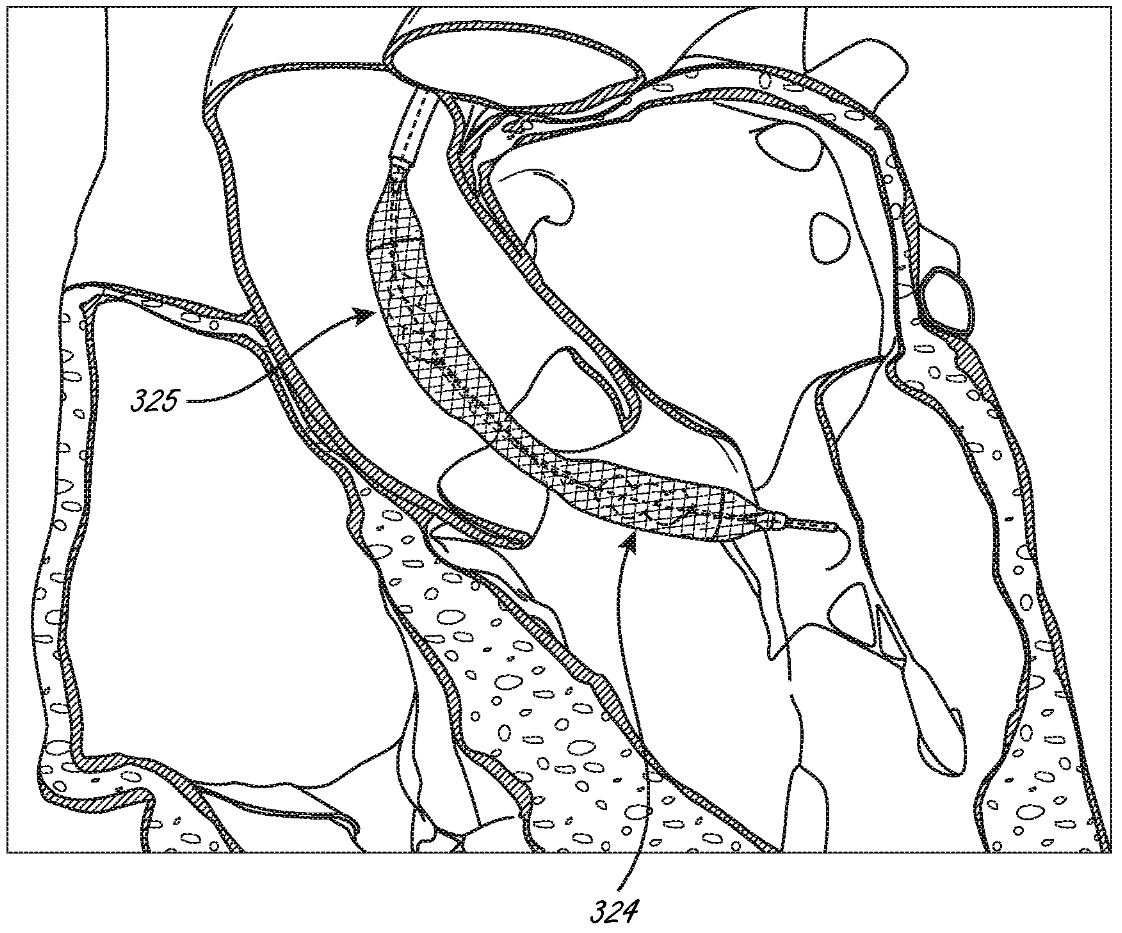

The second wire (e.g., an 0.018" guidewire) may then be moved prior to operation of the pump assembly (see FIG. 12E). If desired or needed, the pump portion can be deflected (active or passively) at one or more locations as described herein, as illustrated in FIG. 12F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. It is understood that in FIG. 12F, the pump portion is not in any way interfering or interacting with the mitral valve, even if it may appear that way from the figure.

The pump portions of the catheter blood pumps herein can be positioned at a target location using a variety of patient access locations and access paths. For example, any of the pump portions herein may be placed across an aortic valve, which may be accessed via a path starting with a femoral artery entry, up the descending aorta, over the aortic arch, and across the valve. The disclosure that follows provides one or more advantages for advancing a blood pump to a target location within the patient. FIGS. 13-16C illustrate distal portions of exemplary blood pumps that include a distal region with an axially extendable member that is adapted to be advanced distally relative to other portions of the blood pump, such as an expandable impeller housing and one or more impellers. The extendable member includes a guide member over which the pump portion can be advanced, which allows the pump portion to track over the axially extendable guide member. The extendable member is axially movable relative to other portions of the blood pump, yet has a limited range of motion and is secured to the pump portion. The exemplary extendable members shown in FIGS. 13-16C are not components that are adapted to be proximally withdrawn out of the patient, unless the entire blood pump is removed from the patient. An exemplary advantage for blood pumps that include an extendable member that includes a guide member is that at any time after the device is introduced into a patient, the extendable member may be advanced distally, and then the remainder of the blood pump (e.g., pump portion) can be distally advanced and tracked over the guide member. For example, there may be instances where the system is being navigated through anatomy that is at least one of difficult to navigate or is delicate. If desired, the extendable member nay be distally advanced (while keeping the rest of the system axially in place) through the difficult to navigate anatomy and/or delicate tissue, and after the extendable member has been advanced to a desired location, the rest of the pump portion may be advanced distally over the guide member, and the extendable member can be re-docked to the rest of the pump portion. An exemplary location where this may be useful is when a pump portion is advanced over the aortic arch. The extendable member may be distally advanced, followed by system tracking over the guide member, as many times as may be desired until the pump portion is safely advanced through the aortic arch and adjacent an aortic valve.

An additional exemplary advantage of blood pumps having extendable members and guide members is that it allows for easy repositioning of the pump portion if desired or needed without having to re-introduce a guidewire that would have been removed prior to pump activation. For example, if after the pump portion is placed at a desired target location, it may migrate during use, such as moving too far proximally out of position. If this happens, the extendable member (including the guide member) can be distally advanced, and then the rest of the system can be tracked over the guide member until it is back in a desired position. This may save a great deal of procedural time and effort by the physician.

The embodiments and figures that follow may illustrate or describe only a portion of an catheter blood pump. It is understood that other suitable components and features of other blood pump systems described herein may be integrated with one or more of the embodiments related to extendable members and guide members.

The extendable members herein are generally described as extendable relative to a pump portion. It is contemplated that the extendable members may be considered part of the pump portion, or even more generally may be considered a distal region of the catheter blood pump that can be extended distally independently from at least one other component in the system, such as the pump portion, one or more impellers, and/or a motor.

Figure 13:
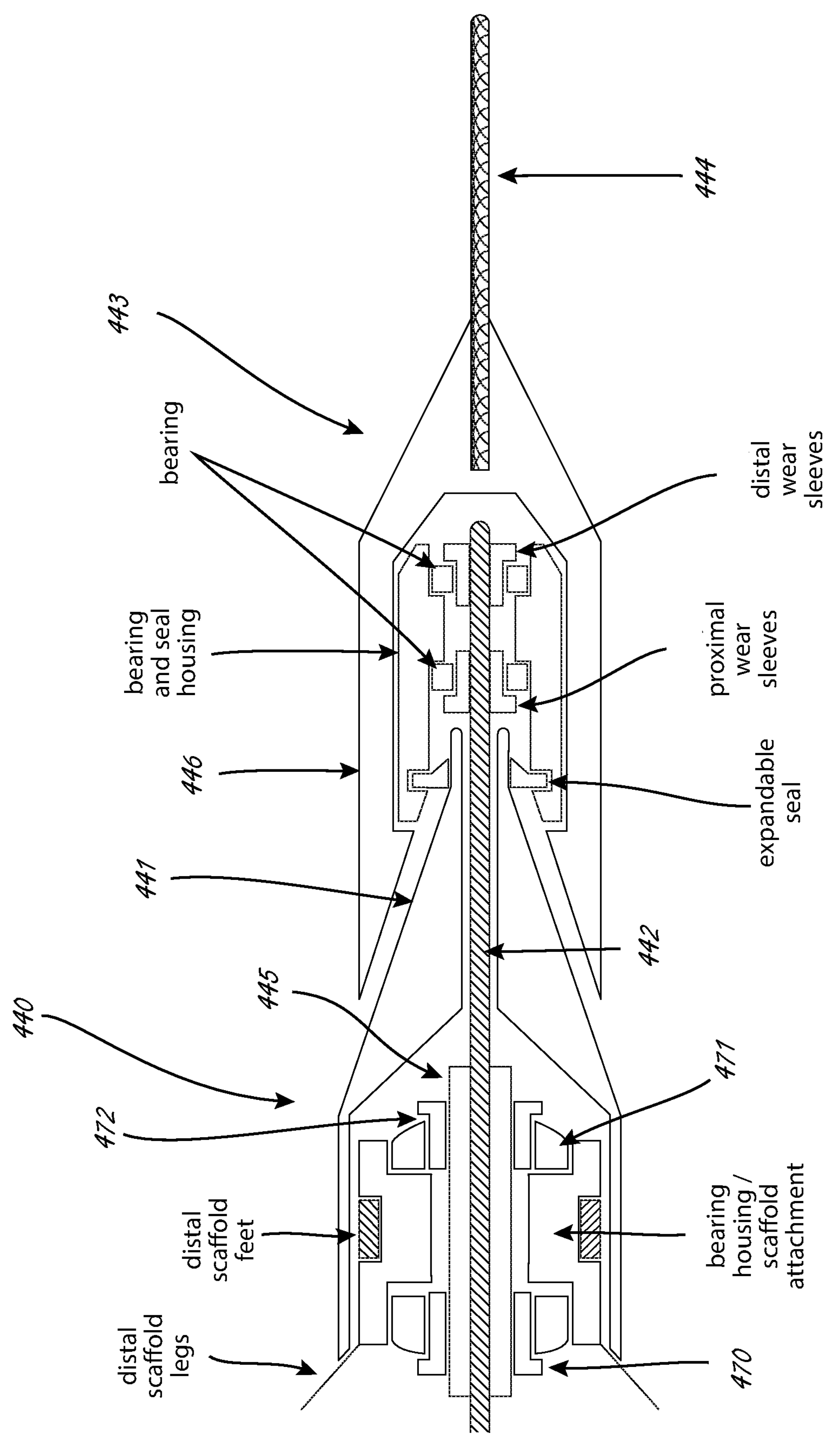
FIG. 13 illustrates a distal portion of a pump portion and an extendible member.
Figure 14A:
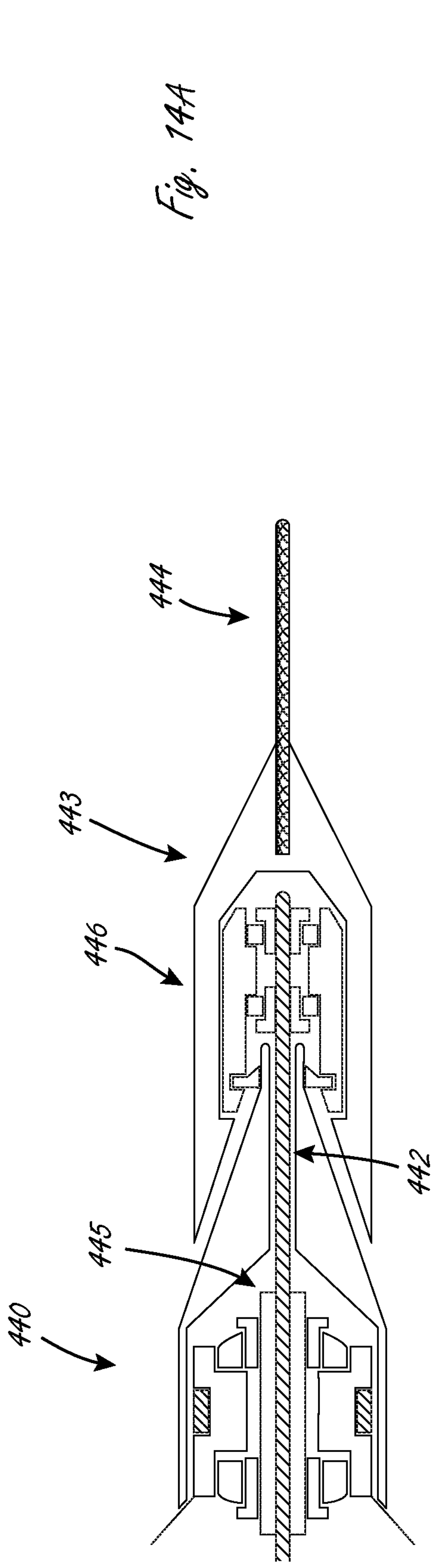
FIGS. 14A and 14B illustrate a non-extended and extended extendible member.
Figure 14B:
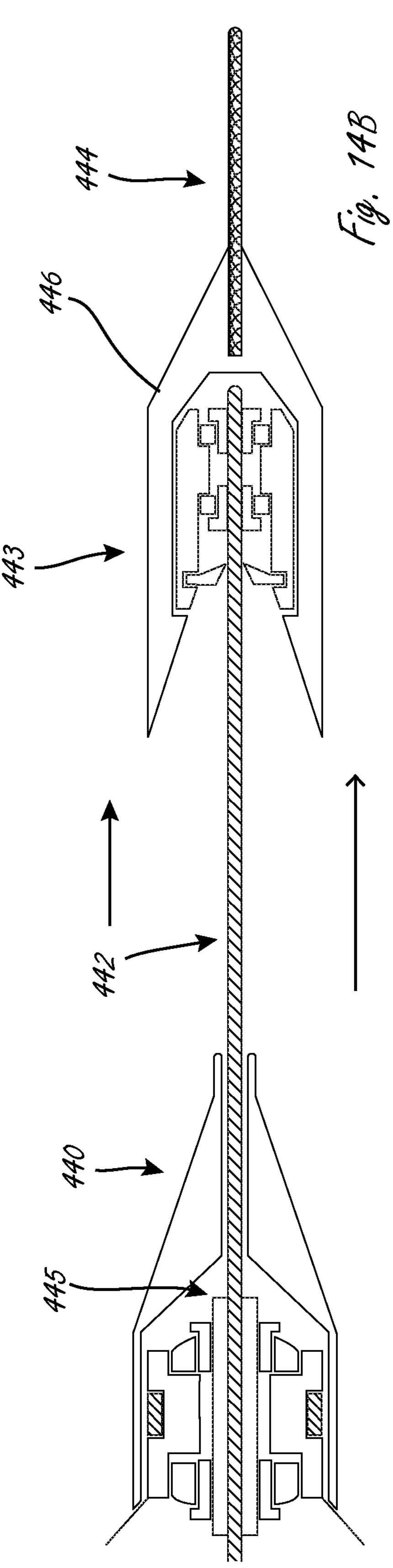
Figure 15:
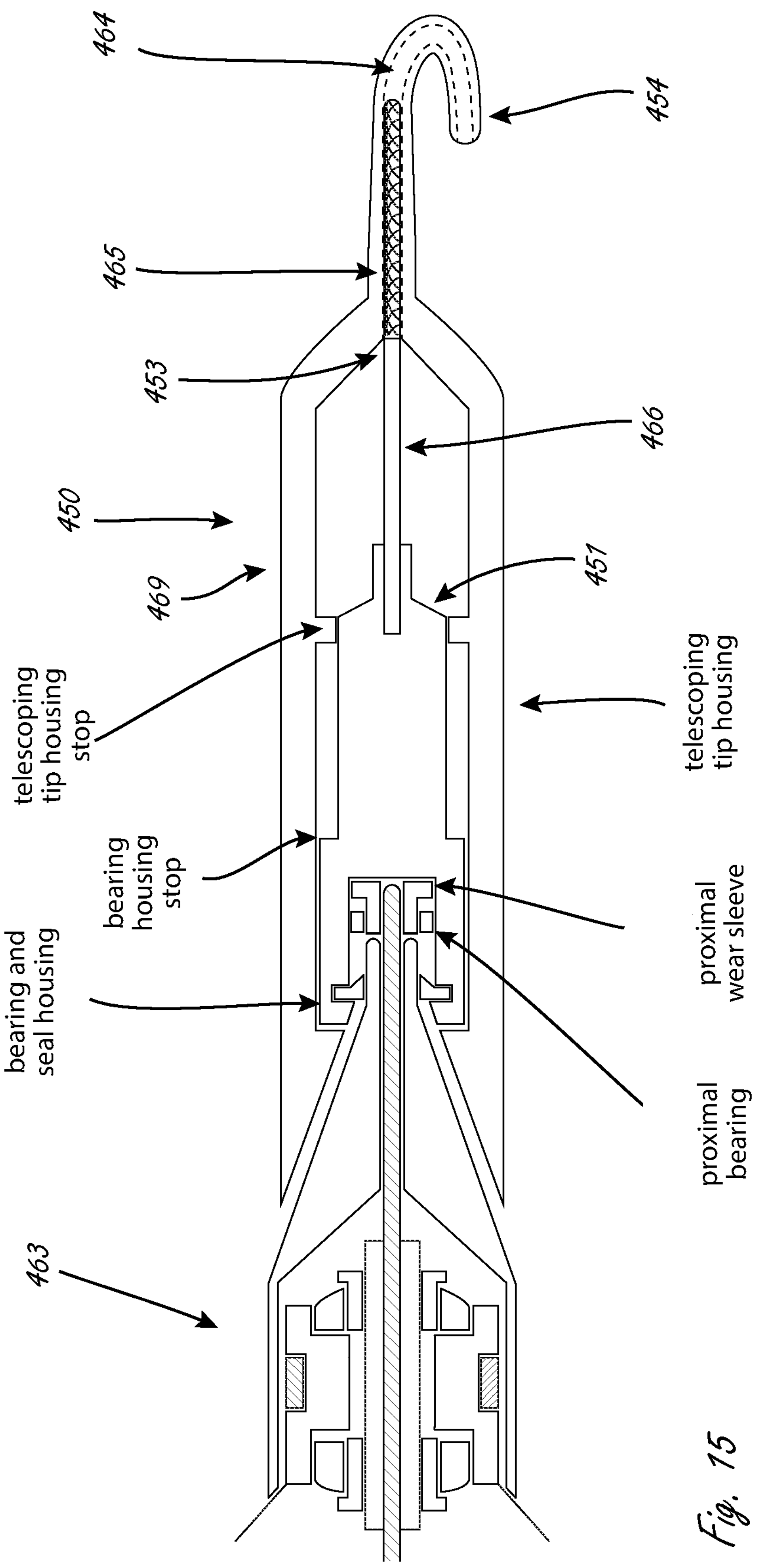
FIG. 15 illustrates a distal portion of a pump portion and an extendible member.

FIGS. 13, 14A and 14B illustrate an exemplary embodiment of a catheter blood pump that includes an axially extendable member disposed distal to one or more impellers. A distal region of an exemplary pump portion 440 is shown (one or more impellers are not shown for clarity). The system also includes axially extendable member 443, which includes body 446 and guide member 442, which is axially fixed to body 446. Guide member 442 can be adapted to be rotatable or non-rotatable relative to body 446, which is described in more detail elsewhere herein.

FIG. 14A illustrates extendable member 443 engaging or immediately adjacent to pump portion 440, which may be referred to herein as a "docked" position of the extendable member. FIG. 14B illustrates the distal end of the system after extendable member 443 (including body 446 and guide member 442) has been advanced distally relative to pump portion 440 (which may include an expandable housing and one or more impellers). This may be referred to herein as an extended position, which can include any number of relative positions in which the extendable member is not docked with the pump portion. After extendable member has been advanced distally as shown in FIG. 14B, the pump portion may be advanced over guide member 442 until the extendable member 443 is again docked with the rest of the system. In this exemplary embodiment, the guide member 442 extends through the rotatable drive mechanism 445, which drives the rotation of the one or more impellers of the pump portion. Guide member 442 also extends through a lumen in a tip of the pump portion 440, as shown in FIG. 14A.

Extendable member 443 (and any other extendable member herein) may also include a flexible tip 444 extending distally from body 446. The flexible tip can be floppy to avoid damaging tissue and to facilitate navigation.

An exemplary advantage of the exemplary blood pump in FIGS. 13, 14A and 14B (as well as the pump in FIGS. 15, 16A and 16B described below) is that the pump can be introduced into a patient without having to have an introducer catheter left in place in the patient as the blood pump is navigated to the desired target location, as is typically done in existing procedures. In procedures in which an introducer catheter is left in place, the outer dimension of the system that is advanced through the introducer catheter cannot be larger than the introducer catheter lumen. This size of the introducer catheter lumen thus limits the maximum outer dimension of the system. Collapsible components such as one or more impellers and/or expandable housings that create a fluid lumen must be collapsible to a configuration such that the overall system, when collapsed, is within the size constraints necessitated by the introducer catheter lumen size. Impellers that are stiffer generally have better performance than impellers that are very flexible. A design consideration for collapsible impellers is thus making sure the impeller will reliably collapse, and yet possess the necessary strength to achieve the desired performance. A blood pump that does not need to be advanced through an introducer catheter can thus have a larger OD than would be required if it were advanced through an introducer catheter. A larger acceptable OD for the system provides for more space in the system, which can free up space for all of the components. This can ease the design constraints on one or more collapsible components (e.g. one or more impellers, expandable housing), which may present more design options to achieve the needed flow performance of the pump.

In embodiments herein, pump portions can be restrained within an outer sheath during delivery. Relative axial movement between the sheath and pump can facilitate the deployment of the pump portion (directly or indirectly). By avoiding the need to use an introducer catheter, the outer sheath can be as large as the introducer catheter that would have been used, which allows for more space in the sheath. For example, if the system was to be introduced through a 9 F introducer catheter, instead of the outer sheath needing to be the same OD as the 9 F dilator OD, the outer sheath can now have an OD equal to a 9 F introducer.

The distal end of the pump portion 440 includes a surface 441 that is configured to function like a dilator, and is preferably semi-rigid and shaped like a standard dilator tip, as shown in the sectional view of FIGS. 14-16C.

An exemplary method of accessing the vasculature and delivering pumps with extendable members herein to a target location follows. A user can gain arterial access using the standard Seldinger technique with a needle and 014 guidewire. Next, they would gain access over the wire with a peel-away 6-8 F introducer (the size depends on the maximum OD of the extendable distal tip section) The dilator would be removed, and then the translascoping extendable member (e.g. 443) of the sheathed system, which is extended all the way out distally away from the pump portion (e.g. as shown in FIG. 14B), would be loaded through the introducer catheter. Once the extendable member and enough of the guide member (e.g., guide member 442) had entered the access channel into the patient, the peel-away introducer would be removed and then peeled away. This would then allow the sheathed system (e.g., including a pump portion in a collapsed configuration within an outer sheath) to track over the guide member, dilate the vessel access open with the exposed dilator-like tip (e.g., tip 441) and outer sheath, and then the system would be able to be advanced to the desired location in the patient, such as adjacent an aortic valve. The process of extending the extendable member distally from the rest of the pump followed by tracking the pump distally over the guide member (de-docking/docking; described elsewhere herein) can be performed as often as desired to navigate the pathway toward the target location. In embodiments in which the extendable member includes a distal floppy tip (e.g., tip 444), a conical or similarly-shaped loading tool with a slit may be needed to be used to aid in loading an extended member with a floppy tip through a hemostasis valve of a peel away introducer catheter.

The extendable members in FIGS. 13-16C may be referred to herein as translascoping members in that the extendable member can be translated axially, and the configuration of the proximal end allows it to be telescoping with the non-extendable end of the pump portion.

In any of the embodiments herein, the catheter blood pump can also be configured so that the extendable member can extend distally but is limited with a stop mechanism to restrict travel distally beyond a certain distance. The distance that the extendable member is adapted to travel may be optimized for particular applications, or for particular regions of the anatomy. It may be beneficial if, for example, the extendable member not be able to extend beyond a certain distance to limit the amount of distal travel without the user having to attempt to manually limit the amount of distal extension.

In some embodiments, the guide member (e.g., guide member 442) is a torqueable central element that is adapted to be distally advanced and proximally pulled, over which a pump assembly and catheter may be advanced and tracked. The translascoping guide member may be a solid core, or it may be hollow. In some embodiments the guide member extends from or near a proximal end of the catheter blood pump through a hollow drive shaft/assembly in the motor, through the lumen of the drive cable, through a pump portion (which includes one or more impellers) and can terminate distal to an impeller and optionally distal to an impeller housing (optionally distal to distal struts that are part of an expandable housing in which at least one impeller at least partially resides in a deployed configuration) in an axially moveable section (e.g., extendible body 446) of the distal tip, as is shown in FIGS. 13-18. This extendable member can be extended away from a fixed section of the distal tip (e.g., dilator-shaped section 441) when the translascoping guide member is pushed at the proximal end of the system, and can re-dock and seal when the guide member is pulled back proximally, as can be seen in FIGS. 13-18.

In some embodiments, the guide member (e.g., guide member 442) is adapted so that it does not rotate when the motor, drive assembly, and one or more impellers are rotated (as shown in the exemplary embodiment in FIG. 5). The guide member may be secured so that it does not rotate when a hollow motor shaft and drive cable rotate around it.

In some embodiments, the guide member is adapted to rotate with the motor/drive assembly/one or more impellers. The guide member can be adapted to rotate from just proximal to the motor shaft (e.g. at the rotating thrust bearing 447 in FIG. 18) all the way to the distal extendable member (e.g., member 443) where a thrust bearing assembly (an example of which is shown in FIG. 13-16B) can prevent the body 446 of the expandable member from rotating. A similar mechanism can be used on the proximal end of the system to prevent the axial displacement control member (e.g., control member 448 shown in FIG. 18) that the user will manipulate to axially control the extendable member from rotating.

In some embodiments the guide member (e.g., guide member 442) may be made of one or more metals or polymers or it may be coated with one or more polymer jacketing(s) or other wear resistant coating(s). In some embodiment the guide member can have a coil construction similar to a drive cable that is either hollow or has a solid core, and may also have a coating over the entire guide member or in one or more discrete sections along its length. In some embodiments the guide member may be a combination of any of the described configurations joined together linearly. In some embodiments it have multiple layers of oppositely wound material, such as coils. In some embodiments, the system may include one or more slightly larger diameter bushings disposed on the guide member, arranged linearly, such that the bushing prevent the drive cable/drive mechanism from contacting the guide member. The one or more bushings, which may contact the rotating drive assembly, may be made of a material that is low friction and will minimize wear from the drive cable/assembly acting upon it.

Figures 16A, 16B, 16C:
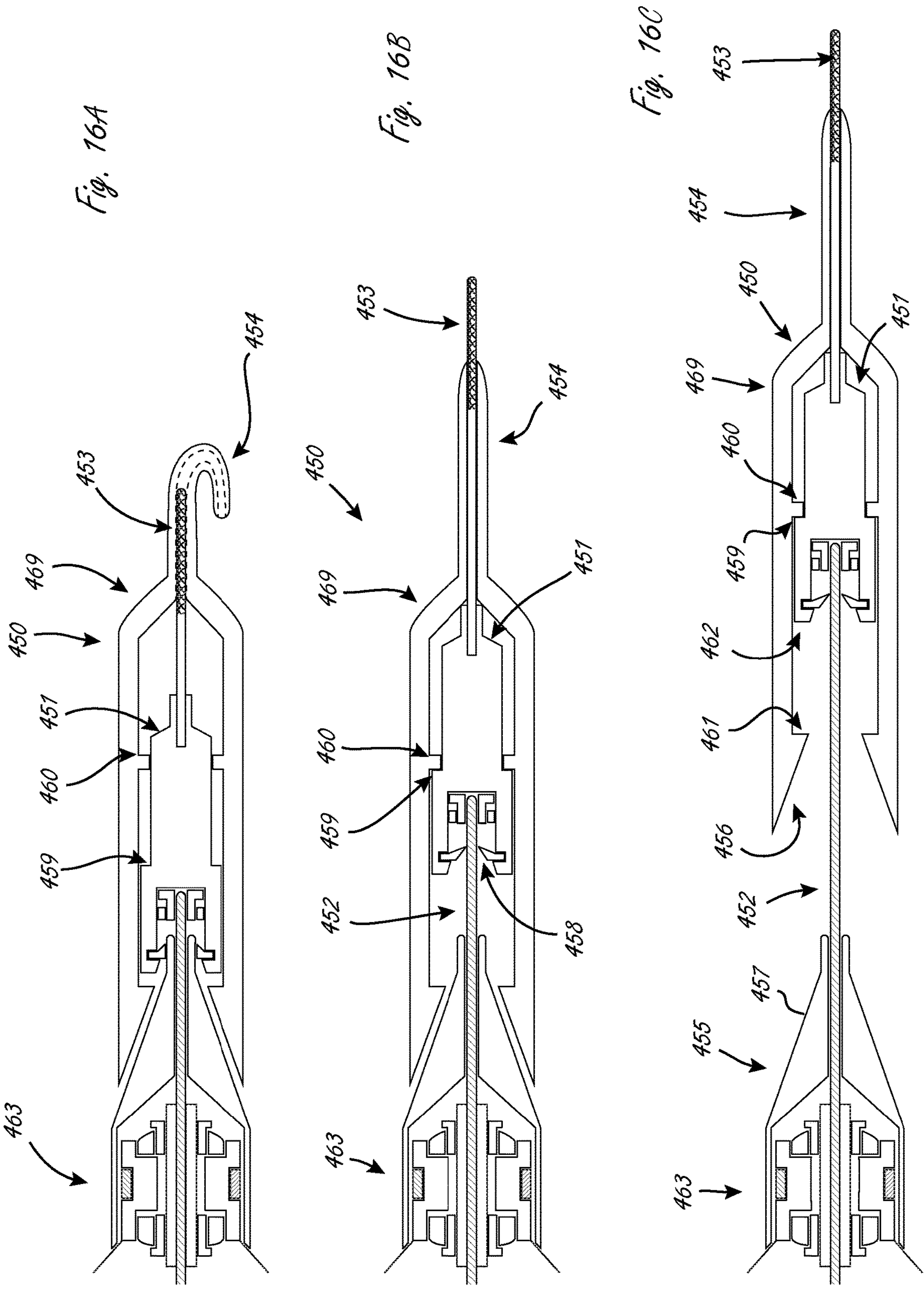
FIGS. 16A-16C illustrate a distal portion of a pump portion and an extendible member.
Figure 17:
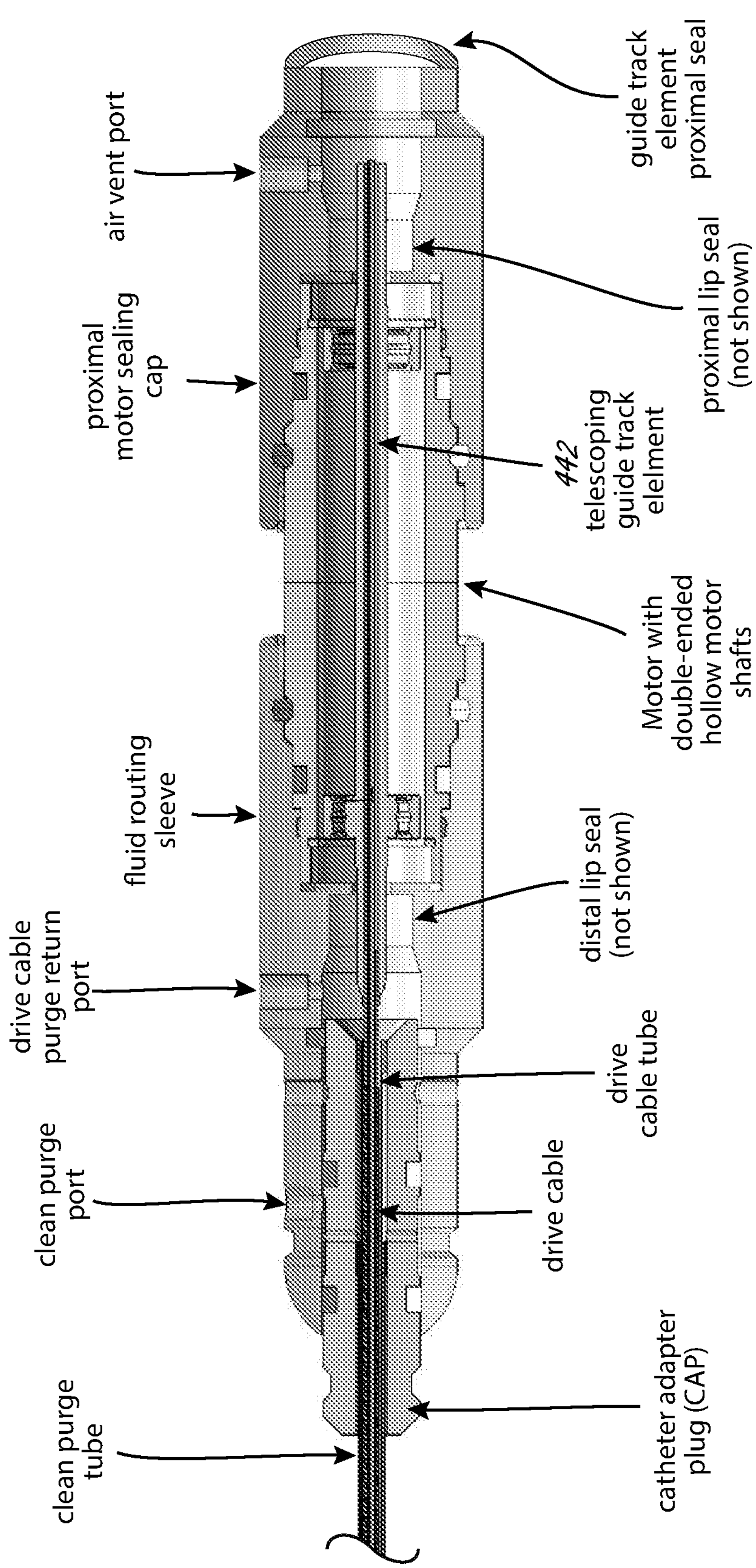
FIG. 17 illustrates a proximal portion of a catheter blood pump.
Figure 18:
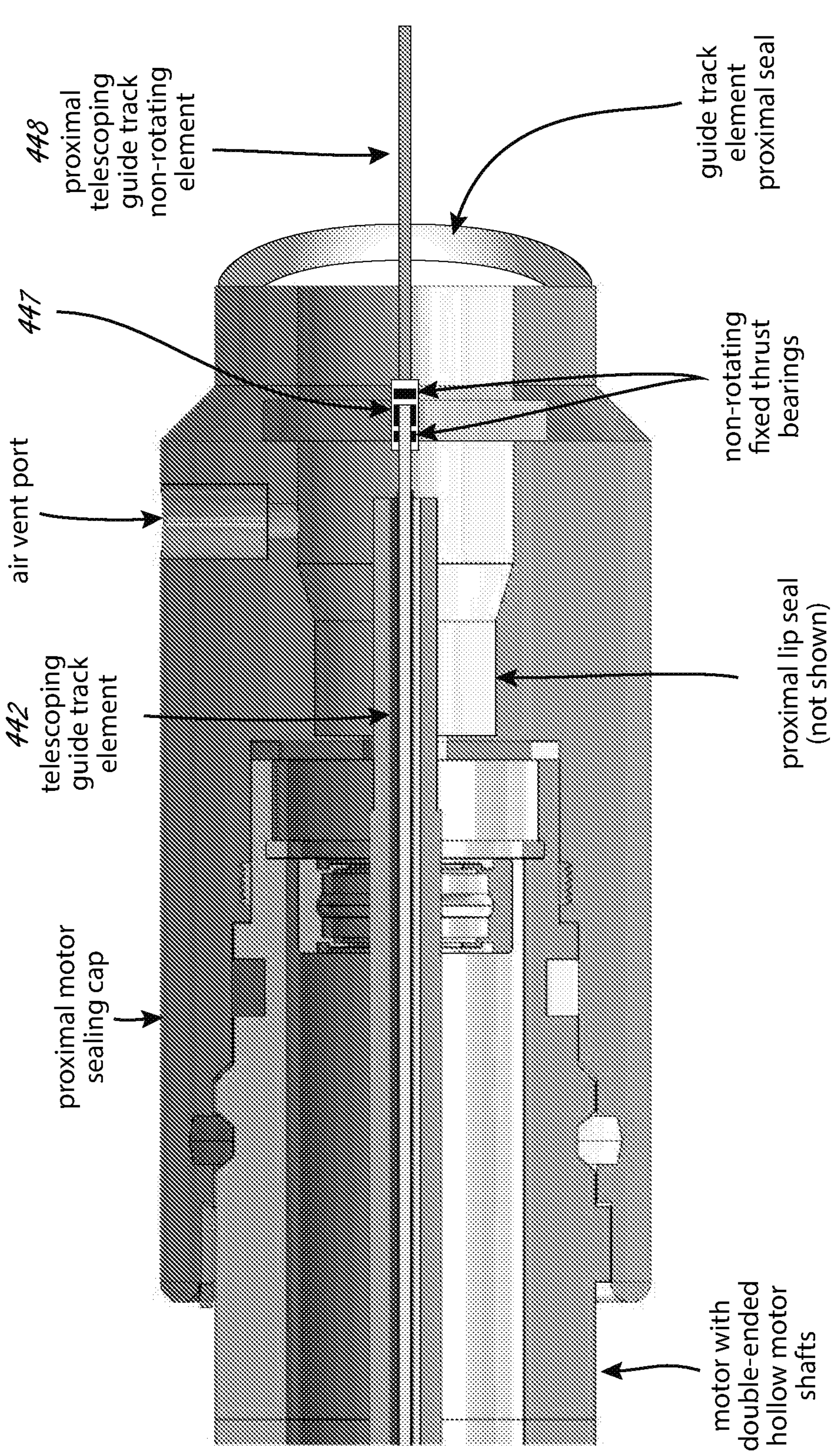
FIG. 18 illustrates a proximal portion of a catheter blood pump.

FIGS. 13 and 14A and 14B illustrate an exemplary extendable member 443, which includes a flexible tip 444 (e.g., a floppy elongate element) extending distally from body portion 446 therefrom. FIGS. 15 and 16A-16C illustrate a portion of a blood pump illustrating an alternative extendable member 450. The proximal end of the system may be as it is illustrated in FIGS. 17 and 18, for example. Extendable member 450 includes an outer body 469 and an inner body 451 that is axially movable with a limited range of motion relative to outer body 469. In some ways, inner body 451 (which is part of extendible member 450) can be considered similar to extendable member 443 in FIG. 13. Guide member 452 is axially fixed to inner body 451 such that axial movement of guide member 452 axially moves inner member 451. Whether outer member 469 also moves or not depends on the relative position of the inner and outer members. A docked position is shown in FIG. 16A. Distally advancing guide member 452 causes guide member 452 and inner member 451 to be advanced distally, as shown in FIG. 16B. When interface element 459 on inner member engages interface member 460 on the outer member 469, continued distal force on guide member 452 causes outer member 469 to also be advanced distally, as shown in the transition between FIGS. 16B and 16C. FIG. 16C shows an exemplary undocked position of extendable member 450.

After extendable member 450 has been advanced distally relative to pump portion 463 (e.g., as shown in FIG. 16C), pump portion 463 can then be advanced distally to track the pump portion over guide element 452, until the extendable member 450 is again engaged with (docked with) pump portion 463 (as in FIG. 16A). As pump portion 463 is advanced distally, seal(s) 458 of the extendible member will interface with surface 457 of the pump portion, which in this embodiment is tapered and shaped like a dilator, which is described in more detail herein. Surface 456 of extendable member 450 may also interface with surface 457, but not necessarily. Surface 462 of inner member 451 may also interface with surface 461 of outer member 469, but not necessarily.

This process of advancing the extendable member and then tracking the pump over the guide member may be performed as often as desired, including after the pump is turned on (e.g., in the event of pump migration).

Inner member 451 includes a distal tip 453 axially fixed thereto and extending distally therefrom. Distal tip 453 includes distal region 465 that is more flexible that proximal region 466, and proximal region 466, which is stiffer than distal region 465. Outer member 469 can include a soft, curved (at least a portion is curved—e.g. having a J-tip configuration) atraumatic tip 454. When inner member tip 453 is advanced distally through channel 464 in curved tip 454, the stiffer inner member tip 453 causes the curved tip 454 to straighten, as shown in FIGS. 16B and 16C, and tip 453 extends distally from a port in the curved tip 454 as shown in FIGS. 16B and 16C. In FIG. 16B the extendable member is still considered docked with the pump portion 463, even though guide member 452 has been advanced distally to some extent relative to the pump portion.

Inner member 451 can be considered another translascoping element inside an outer portion of the extendable member. In the configuration in FIGS. 15 and 16A-16C, where the flexible tip 453 is also translascoping, the atraumatic distal tip 454 can be bent or curled in a natural at rest-state, and the floppy tip 453 can have a stiffer section 466 such that when it is extended out the atraumatic tip 454 will be straightened, as shown in FIGS. 16B and 16C.

The entire disclosure herein related to FIGS. 13 and 14A and 14B can be applied to FIGS. 15 and 16A-16C. For example, the methods of use and access target locations in the patient is incorporated into the disclosure of FIGS. 15 and 16A-16C.

In some alternative embodiments the distal tip is straight in a natural, at-rest, state but when the translascoping guide member is pulled at the proximal end of the system, the distal end of the element which is fixed at the distal tip will cause the tip to deflect and curl back. This allows for having a straight tip for crossing the valve and once the system is in place the tip can be curled back leaving an atraumatic bend at the end in case the system migrates deeper into the Left Ventricle. Furthermore if there is a fixed floppy tip at the distal end that cannot be pulled back into the extendable tip, by curling the tip back towards the system it might keep the floppy tip from irritating the LV walls. This same concept can be applied to a translascoping floppy tip design as well.

In some embodiments, a catheter body (e.g., elongate portion 1106 in FIG. 4) and/or outer sheath can be configured to preferentially bend in one or more axial sections. For example, in use, the translascoping guide member can be pulled/tensioned at a proximal region of the system, which can cause an outer sheath to bend in one or more particular regions, due to, for example, a variable stiffness along the shaft of the sheath. The sheath can be configured to bend in the more flexible regions and not (or less) in relatively stiffer regions. This can be helpful if it is beneficial to have a shaft bend at particular regions when they are near or adjacent certain anatomical locations. For example, it may be beneficial to have a shaft bend along an aortic arch, but not in a region proximal to the arch. If for example the outer sheath is stiffer proximal to the arch and more flexible in the section around the arch, not only could the distal tip be bent (as described above) but the shaft would preferentially bend in the more flexible section. This could be useful when delivering or removing the system as well as it could cause less stress on the arch while the device is seated in the valve during operation. A tensioning force can thus be applied at any time while the pump is in use to change the configuration of the shaft to, for example, reduce stress on certain anatomical locations over extended periods of time. This disclosure thus describes blood pump that may include a tensioning guide element that can be used to track a portion of the pump as well as to tension the system and cause preferential configurational changes in a shaft in the system.

Due to the high rotational speeds and long duration of run time, component wear is a serious issue that may cause failures or decrease device performance. Some of the main areas of component wear are at alignment bearing and thrust bearing contact areas, such as at 470, 471 and 472 in FIG. 13. If the hardness of either the bearing or component rotating inside of it differs greatly, the softer of the materials will wear quickly and fail. If both components have similar hardness but too soft, they will both wear as well. In embodiments in which the drive cable and coupling components are metal, this creates a difficult situation as metal on metal interfaces will wear unacceptably. One approach to address this problem is to incorporate very hard ruby/sapphire components that are polished and extremely low friction. One of the components is a thin walled sleeve (e.g. 470 in FIG. 13) that gets permanently fixed to the rotating drive components, and the other is a slightly larger diameter bushing (e.g., 471 in FIG. 13) fixed so as not to rotate. The thin walled sleeve fits tightly through the bushing and rotates inside of it. Due to the low friction, high hardness and matched hardness, the wear surfaces will last for long periods of time with little to no appreciable wear. The design of the wear sleeves may be simple cylinders, or they may have another larger diameter section that can also act as a thrust bearing face against the face of the bearing/bushing that the wear sleeve is inside of (see 470, 471, and 472 in FIG. 13). This allows for less components as well as minimizing the wear of the position locating thrust faces. The other advantage of having a larger diameter section of the wear sleeve is that it can provide more material and surface area to bond to the rotating component that the wear sleeve is protecting. The sleeves and bearings described in this context may be incorporated into any suitable embodiment herein.

The invention claimed is:

1. A blood pump, comprising:

a pump portion including an impeller housing and an impeller, the pump portion comprising a distal end;

a rotatable drive mechanism in operable rotational communication with the impeller to cause the impeller to rotate;

an axially extendable member with a distal end that is disposed further distally than the distal end of the pump portion, a guide member extending through the pump portion and axially moveable relative to the pump portion, the guide member in operable axial communication with the extendable member such that axial movement of the guide member causes axial movement of the extendable member relative to the pump portion; wherein the guide member is adapted to be rotatable relative to the extendable member.

2. The blood pump of claim 1, wherein the guide member is axially secured to the extendable member.

3. The blood pump of claim 1, wherein the guide member is not adapted to be rotatable relative to the extendable member.

4. The blood pump of claim 1, wherein the extendable member includes a distally extending flexible tip.

5. The blood pump of claim 1, wherein the extendable member comprises one or more surfaces that are configured and sized to interface with one or more surfaces of the distal end of the pump housing so as to prevent proximal movement of the extendable member when the one or more surfaces of the extendable member interface with the one or more surfaces of the distal end of the pump housing.

6. The blood pump of claim 5, wherein the distal end of the pump portion has a tapered configuration, narrowing in the distal direction.

7. The blood pump of claim 1, wherein the extendable member comprises an inner seal positioned to interface with and seal against an outer surface of the distal end of the pump portion.

8. The blood pump of claim 7, where the inner seal has an at-rest configuration that extends further radially inward toward the guide member when the extendable member is advanced proximally away from the pump housing.

9. A blood pump, comprising:

a pump portion including an impeller housing and an impeller, the pump portion comprising a distal end;

a rotatable drive mechanism in operable rotational communication with the impeller to cause the impeller to rotate;

an axially extendable member with a distal end that is disposed further distally than the distal end of the pump portion, a guide member extending through the pump portion and axially moveable relative to the pump portion, the guide member in operable axial communication with the extendable member such that axial movement of the guide member causes axial movement of the extendable member relative to the pump portion; wherein the guide member is axially secured to an inner member of the extendable member, the extendable member further comprising outer member, wherein the inner member is adapted to be axially moved relative to the outer member with a limited range of motion, wherein the outer member and the inner member each have one or more surfaces that are configured such that when the one or more surfaces interface, the inner member and the outer member move together distally, but when the one or more surfaces are not interfaced, the inner member can move distally without causing distal movement of the outer member.

* * * * *